United States Patent [19]

Abad et al.

[11] Patent Number: 6,120,999
[45] Date of Patent: Sep. 19, 2000

US006120999A

[54] **HISTIDINE KINASE TWO-COMPONENT IN *CANDIDA ALBICANS***

[75] Inventors: Antonio Jose C. Abad, Washington, D.C.; Gil H. Choi, Rockville, Md.; Richard A. Calderone, Washington, D.C.

[73] Assignees: Human Genome Sciences, Inc., Rockville, Md.; The Georgetown University, Washington, D.C.

[21] Appl. No.: 09/112,450

[22] Filed: Jul. 9, 1998

Related U.S. Application Data

[60] Provisional application No. 60/052,273, Jul. 10, 1997, and provisional application No. 60/074,308, Feb. 11, 1998.

[51] Int. Cl.[7] .............................. C12Q 1/68; C12P 19/34; C07H 21/04; C12N 15/00
[52] U.S. Cl. ..................... 435/6; 435/69.1; 435/91.2; 435/252.3; 435/320.1; 536/23.2; 536/23.74; 536/24.32; 536/24.33
[58] Field of Search .............................. 435/6, 69.1, 91.2, 435/252.3, 320.1; 536/23.1, 23.2, 23.74, 24.32, 24.33

[56] References Cited

PUBLICATIONS

Schuster, S.C. et al. EMBO Journal 15(15):3880–3889, 1996.
Nagasawa, S. et al. Mol. Microbiol. 6(6):799–807, 1992.
Hrabak, E.M. et al. J. Bacteriol. 174(9):3011–3020, May 1992.
Schuster, S.C. et al, Accession No. S71628, 1996.
Calera, J.A. et al., Yeast, vol. 14:665–674 (1998).
Bassler, B.L., et al., Molecular Microbiology, vol. 13:273–286 (1994).
Hrabak, E.M. et al., J. Bacteriology, vol. 174:3011–3020 (1992).
International Search Report (PCT/US98/14254) (1998).
Nagasawa, S. et al, Accession No. S20550, 1992.
Hrabak, E.M. et al, Accession No. B41863, 1992.

*Primary Examiner*—Carla J. Myers
*Assistant Examiner*—Diana Johannsen
*Attorney, Agent, or Firm*—Kenley K. Hoover

[57] ABSTRACT

The present invention relates to a histidine kinase, two-component gene (CaHK1) from *Candida albicans*. CaHK1 encodes a 2471 amino acid protein with an estimated molecular mass of 281.8 kDa. Also provided are vectors, host cells, antibodies and recombinant methods for producing the same. The invention further relates agonists and antagonists and to screening methods for identifying agonists and antagonists of CaHK1 polypeptide activity. The invention additionally relates to diagnostic methods for detecting CaHK1 nucleic acids, polypeptides, and antibodies in a biological sample. The present invention further relates to novel antagonists and vaccines for the prevention or attenuation of infection by *Candida albicans*.

20 Claims, 21 Drawing Sheets

```
CATATGTTCAGTCTATTTATGAATATTATTTCAGTTGTCATGCTGTATTTTTTGAATCAATTGAAAAAA
TGCTGGATCTTATACATCCAGGTAACGCTAGTTCCCATTGCACAAGACTGTCTTATTATTCATCTTTTC
ATTTGATAGTTAATGTTTCCAAGATTTTCTTTTCATGTATGAATGGAGAAAGTTTCAAAATGTTCTCAA
CATTTCAAGTGTAAATCCTATTTAACAGGGGATCCCCAAATGCCTGAAATGGACAATTTTTTATACGAT
AGTGAAATGTTACTTGCTGGACATTCAGAATTGAATGAATTTATGAGAAAATATCAGTCATTCAACCAA
ACTTCCGTTGGTAAATTTTGCTACTATTTAATTGTACTACTTGTAATGTCACGTGAACACAGATTTGAC
GAGGCTGCCGATTTGGTTTTGAAAGTTTTGGAAGACTTACTGGAAAAATTGCCTGTATCTTTTTTGCAT
CATCAATATTACTTAATATGTGGTAAAGTGTTTGCTTATCACCAGACCAAAACCCCAGAAAGTGAGGAA
CAAGTGGAACGTATTTTGGCTCGTCAATTTGAAAGATATGAATTGTGGGCACTGACGAATAAGCCGACC
CTTCTACCACGGTACTTGTTGTTGAGTACCTACAAACAGATTAGAGAAAACCATGTTGACAAGTTAGAA
ATACTAGATTCATTTGAGGAGGCGTTACAGACGGCCCATAAATTTCATAATGTATATGATATGTGCTGG
ATCAATTTGGAATGTGCAAGATGGTTAATTAGCATAAACCAAAAAGGCACAGAATCTCAAGAATGGTT
AAACAAGGTCTTAAAATTTTGAGAAGCTTGGAATTAAATAATCATTTAAGATTAGCTGAATTTGAATTT
GATGAATACATTGAGGACGAAGATCACAGAAATAAATGGGCAGGGTTAACTAATAATCCAACATTGGAT
ACTGTTACTACCTGGCAACAACAGAACATGCCCGATAAGGTATCTCCATGCAATGACAAGCAGTTGGTC
CACGGAAAACAATTTGGCAAAAAGAGTTTGATAGCCATTTGCTCAGATTGCACTTTGATGGCCAATAT
ACAGGCCTAGATTTGAATTCAGCTATTCGTGAATGTCTAGCAATATCCGAAGCTTTAGACGAAAATTCC
ATTCTCACAAAGTTGATGGCATCTGCCATCAAGTATTCAGGTGCCACATATGGGGTAATTGTCACGAAG
AAAAACCAGGAGACACCTTTTCTTAGAACAATTGGCTCGCAGCACAATATTCACACATTAAACAACATG
CCAATTTCCGACGACATTTGTCCTGCTCAGTTGATTCGTCATGTATTGCATACAGGAGAAACGGTGAAC
AAAGCTCATGATCACATAGGATTTGCTAACAAGTTTGAGAATGAATACTTTCAAACAACAGATAAAAAG
TATTCAGTTGTGTGTTTGCCATTAAAGAGTCTGCTTGGATTATTTGGTGCACTTTATCTAGAAGGTAGT
GATGGTGATTTTGGACATGAAGATTTGTTCAATGAAAGGAAATGTGATTTGTTACAACTTTTTTGCACA
CAAGCAGCTGTGGCTTTGGGTAAGGAGCGTTTGCTTTTGCAAATGGAACTAGCAAAAATGGCAGCAGAA
GACGCCACTGATGAAAAAGCCAGTTTTTTGGCAAACATGTCACATGAAATACGAACCCCATTCAATTCG
TTATTGTCATTTGCTATTTTTTGTTAGATACCAAATTGGATTCTACTCAAAGAGAATATGTCGAGGCA
ATTCAGAGCTCCGCAATGATAACGTTGAATATTATTGATGGGATACTTGCGTTTTCCAAAATTGAGCAT
GGATCCTTTACATTAGAAATGCCCCCTTTTCTTTGAATGATTGTATCGAGACTGCTATTCAAGTAAGT
GGGGAAACAATTTTGAATGACCAGATTGAGTTGGTGTTTTGTAACAATTGTCCAGAGATTGAATTTGTG
GTTGGTGATCTAACGAGGTTCAGACAAATTGTGATCAATTTGGTGGGTAATGCTATTAAGTTTACAACC
AAAGGTCATGTTTTGATTTCTTGTGATAGCCGAAAAATTACGGACGACAGATTTGAGATCAATGTGTCA
GTTGAGGATTCAGGAATTGGAATTTCCAAAAAATCTCAAAATAAAGTGTTTGGAGCATTTTCTCAAGTA
GATGGTTCCGCAAGACGAGAATATGGTGGCTCTGGATTAGGTTTAGCTATATCAAAGAAATTGACTGAA
CTAATGGGTGGCACAATTAGATTTGAAAGTGAGGAAGGGATTGGCACAACGTTTTATGTTAGCGTCATT
ATGGACGCAAAAGAATACTCATCCCCGCCATTTAGTTTAAATAAAAAATGTTTGATTTACAGCCAGCAT
TGTCTTACTGCCAAGTCAATTTCAAATATGCTTAATTATTTTGGATCAACAGTTAAAGTCACTAATCAG
AAGTCTGAGTTTTCAACTTCCGTGCAAGCCAACGACATCATTTTTGTTGATCGCGGAATGGAACCTGAT
GTTAGTTGCAAAACCAAATCATTCCCATCGACCCAAAACCTTTCAAAAGAAACAAACTCATTAGTATT
CTCAAAGAACAACCAAGTTTGCCCACCAAAGTGTTTGGAAACAACAAATCTAATTTATCAAAACAATAC
CCTCTAAGAATATTATTAGCAGAAGACAATCTTTTGAACTATAAAGTATGTTTGAAGCATTTGGATAAA
TTGGGGTACAAGGCAGATCATGCCAAAGATGGAGTAGTAGTTTTGGATAAATGTAAAGAACTACTAGAA
AAAGACGAAAAATATGATGTCATATTGATGGATATTCAAATGCCTCGTAAGGACGGTATTACAGCTACA
AGGGATTTGAAAACATTGTTTCACACACAAAAAAGGAAAGTTGGTTACCCGTGATCGTAGCATTGACA
GCTAATGTTGCTGGAGACGACAAAAAGAGGTGTCTAGAAGAGGGAATGTTTGATTTTATAACCAAACCC
ATTTTACCAGATGAACTTAGACGTATTTTAACAAAAGTAGGGGAAACAGTGAATATGTAAAATGTGTAT
TTAATAATAAGATC
```

FIG. 1A

MEKVSKCSQHFKCKSYLTGDPQMPEMDNFLYDSEMLLAGHSELNEFMRKYQSFNQTSVGKFCYYLIVLL
VMSREHRFDEAADLVLKVLEDLLEKLPVSFLHHQYYLICGKVFAYHQTKTPESEEQVERILARQFERYE
LWALTNKPTLLPRYLLLSTYKQIRENHVDKLEILDSFEEALQTAHKFHNVYDMCWINLECARWLISINQ
KRHRISRMVKQGLKILRSLELNNHLRLAEFEFDEYIEDEDHRNKWAGLTNNPTLDTVTTWQQQNMPDKV
SPCNDKQLVHGKQFGKKEFDSHLLRLHFDGQYTGLDLNSAIRECLAISEALDENSILTKLMASAIKYSG
ATYGVIVTKKNQETPFLRTIGSQHNIHTLNNMPISDDICPAQLIRHVLHTGETVNKAHDHIGFANKFEN
EYFQTTDKKYSVVCLPLKSLLGLFGALYLEGSDGDFGHEDLFNERKCDLLQLFCTQAAVALGKERLLLQ
MELAKMAAEDATDEKASFLANMSHEIRTPFNSLLSFAIFLLDTKLDSTQREYVEAIQSSAMITLNIIDG
ILAFSKIEHGSFTLENAPFSLNDCIETAIQVSGETILNDQIELVFCNNCPEIEFVVGDLTRFRQIVINL
VGNAIKFTTKGHVLISCDSRKITDDRFEINVSVEDSGIGISKKSQNKVFGAFSQVDGSARREYGGSGLG
LAISKKLTELMGGTIRFESEEGIGTTFYVSVIMDAKEYSSPPFSLNKKCLIYSQHCLTAKSISNMLNYF
GSTVKVTNQKSEFSTSVQANDIIFVDRGMEPDVSCKTKIIPIDPKPFKRNKLISILKEQPSLPTKVFGN
NKSNLSKQYPLRILLAEDNLLNYKVCLKHLDKLGYKADHAKDGVVVLDKCKELLEKDEKYDVILMDIQM
PRKDGITATRDLKTLFHTQKKESWLPVIVALTANVAGDDKKRCLEEGMFDFITKPILPDELRRILTKVG
ETVNM

FIG. 1B

```
  1  CATATGTTCAGTCTATTTATGAATATTATTTCAGTTGTCATGCTGTATTTTTTGAATCAA    60

61  TTGAAAAAATGCTGGATCTTATACATCCAGGTAACGCTAGTTCCCATTGCACAAGACTGT   120

121  CTTATTATTCATCTTTTCATTTGATAGTTAATGTTTCCAAGATTTTCTTTTCATGTATGA   180

181  ATGGAGAAAGTTTCAAAATGTTCTCAACATTTCAAGTGTAAATCCTATTTAACAGGGGAT   240
  1  M   E   K   V   S   K   C   S   Q   H   F   K   C   K   S   Y   L   T   G   D    20

241  CCCCAAATGCCTGAAATGGACAATTTTTTATACGATAGTGAAATGTTACTTGCTGGACAT   300
 21  P   Q   M   P   E   M   D   N   F   L   Y   D   S   E   M   L   L   A   G   H    40

301  TCAGAATTGAATGAATTTATGAGAAAATATCAGTCATTCAACCAAACTTCCGTTGGTAAA   360
 41  S   E   L   N   E   F   M   R   K   Y   Q   S   F   N   Q   T   S   V   G   K    60

361  TTTTGCTACTATTTAATTGTACTACTTGTAATGTCACGTGAACACAGATTTGACGAGGCT   420
 61  F   C   Y   Y   L   I   V   L   L   V   M   S   R   E   H   R   F   D   E   A    80

421  GCCGATTTGGTTTTGAAAGTTTTGGAAGACTTACTGGAAAAATTGCCTGTATCTTTTTTG   480
 81  A   D   L   V   L   K   V   L   E   D   L   L   E   K   L   P   V   S   F   L   100

481  CATCATCAATATTACTTAATATGTGGTAAAGTGTTTGCTTATCACCAGACCAAAACCCCA   540
101  H   H   Q   Y   Y   L   I   C   G   K   V   F   A   Y   H   Q   T   K   T   P   120

541  GAAAGTGAGGAACAAGTGGAACGTATTTTGGCTCGTCAATTTGAAAGATATGAATTGTGG   600
121  E   S   E   E   Q   V   E   R   I   L   A   R   Q   F   E   R   Y   E   L   W   140

601  GCACTGACGAATAAGCCGACCCTTCTACCACGGTACTTGTTGTTGAGTACCTACAAACAG   660
141  A   L   T   N   K   P   T   L   L   P   R   Y   L   L   L   S   T   Y   K   Q   160

661  ATTAGAGAAAACCATGTTGACAAGTTAGAAATACTAGATTCATTTGAGGAGGCGTTACAG   720
161  I   R   E   N   H   V   D   K   L   E   I   L   D   S   F   E   E   A   L   Q   180

721  ACGGCCCATAAATTTCATAATGTATATGATATGTGCTGGATCAATTTGGAATGTGCAAGA   780
181  T   A   H   K   F   H   N   V   Y   D   M   C   W   I   N   L   E   C   A   R   200

781  TGGTTAATTAGCATAAACCAAAAAAGGCACAGAATCTCAAGAATGGTTAAACAAGGTCTT   840
201  W   L   I   S   I   N   Q   K   R   H   R   I   S   R   M   V   K   Q   G   L   220

841  AAAATTTTGAGAAGCTTGGAATTAAATAATCATTTAAGATTAGCTGAATTTGAATTTGAT   900
221  K   I   L   R   S   L   E   L   N   N   H   L   R   L   A   E   F   E   F   D   240
```

FIG. 2A

```
901  GAATACATTGAGGACGAAGATCACAGAAATAAATGGGCAGGGTTAACTAATAATCCAACA  960
241   E  Y  I  E  D  E  D  H  R  N  K  W  A  G  L  T  N  N  P  T   260

961  TTGGATACTGTTACTACCTGGCAACAACAGAACATGCCCGATAAGGTATCTCCATGCAAT  1020
261   L  D  T  V  T  T  W  Q  Q  N  M  P  D  K  V  S  P  C  N      280

1021 GACAAGCAGTTGGTCCACGGAAAACAATTTGGCAAAAAAGAGTTTGATAGCCATTTGCTC  1080
281   D  K  Q  L  V  H  G  K  Q  F  G  K  K  E  F  D  S  H  L  L   300

1081 AGATTGCACTTTGATGGCCAATATACAGGCCTAGATTTGAATTCAGCTATTCGTGAATGT  1140
301   R  L  H  F  D  G  Q  Y  T  G  L  D  L  N  S  A  I  R  E  C   320

1141 CTAGCAATATCCGAAGCTTTAGACGAAAATTCCATTCTCACAAAGTTGATGGCATCTGCC  1200
321   L  A  I  S  E  A  L  D  E  N  S  I  L  T  K  L  M  A  S  A   340

1201 ATCAAGTATTCAGGTGCCACATATGGGGTAATTGTCACGAAGAAAAACCAGGAGACACCT  1260
341   I  K  Y  S  G  A  T  Y  G  V  I  V  T  K  K  N  Q  E  T  P   360

1261 TTTCTTAGAACAATTGGCTCGCAGCACAATATTCACACATTAAACAACATGCCAATTTCC  1320
361   F  L  R  T  I  G  S  Q  H  N  I  H  T  L  N  N  M  P  I  S   380

1321 GACGACATTTGTCCTGCTCAGTTGATTCGTCATGTATTGCATACAGGAGAAACGGTGAAC  1380
381   D  D  I  C  P  A  Q  L  I  R  H  V  L  H  T  G  E  T  V  N   400

1381 AAAGCTCATGATCACATAGGATTTGCTAACAAGTTTGAGAATGAATACTTTCAAACAACA  1440
401   K  A  H  D  H  I  G  F  A  N  K  F  E  N  E  Y  F  Q  T  T   420

1441 GATAAAAAGTATTCAGTTGTGTGTTTGCCATTAAAGAGTCTGCTTGGATTATTTGGTGCA  1500
421   D  K  K  Y  S  V  V  C  L  P  L  K  S  L  L  G  L  F  G  A   440

1501 CTTTATCTAGAAGGTAGTGATGGTGATTTTGGACATGAAGATTTGTTCAATGAAAGGAAA  1560
441   L  Y  L  E  G  S  D  G  D  F  G  H  E  D  L  F  N  E  R  K   460

1561 TGTGATTTGTTACAACTTTTTTGCACACAAGCAGCTGTGGCTTTGGGTAAGGAGCGTTTG  1620
461   C  D  L  L  Q  L  F  C  T  Q  A  A  V  A  L  G  K  E  R  L   480

1621 CTTTTGCAAATGGAACTAGCAAAAATGGCAGCAGAAGACGCCACTGATGAAAAAGCCAGT  1680
481   L  L  Q  M  E  L  A  K  M  A  A  E  D  A  T  D  E  K  A  S   500

1681 TTTTTGGCAAACATGTCACATGAAATACGAACCCCATTCAATTCGTTATTGTCATTTGCT  1740
501   F  L  A  N  M  S  H  E  I  R  T  P  F  N  S  L  L  S  F  A   520
```

FIG. 2B

```
1741 ATTTTTTTGTTAGATACCAAATTGGATTCTACTCAAAGAGAATATGTCGAGGCAATTCAG 1800
 521  I  F  L  L  D  T  K  L  D  S  T  Q  R  E  Y  V  E  A  I  Q   540

1801 AGCTCCGCAATGATAACGTTGAATATTATTGATGGGATACTTGCGTTTTCCAAAATTGAG 1860
 541  S  S  A  M  I  T  L  N  I  I  D  G  I  L  A  F  S  K  I  E   560

1861 CATGGATCCTTTACATTAGAAAATGCCCCCTTTTCTTTGAATGATTGTATCGAGACTGCT 1920
 561  H  G  S  F  T  L  E  N  A  P  F  S  L  N  D  C  I  E  T  A   580

1921 ATTCAAGTAAGTGGGGAAACAATTTTGAATGACCAGATTGAGTTGGTGTTTTGTAACAAT 1980
 581  I  Q  V  S  G  E  T  I  L  N  D  Q  I  E  L  V  F  C  N  N   600

1981 TGTCCAGAGATTGAATTTGTGGTTGGTGATCTAACGAGGTTCAGACAAATTGTGATCAAT 2040
 601  C  P  E  I  E  F  V  V  G  D  L  T  R  F  R  Q  I  V  I  N   620

2041 TTGGTGGGTAATGCTATTAAGTTTACAACCAAAGGTCATGTTTTGATTTCTTGTGATAGC 2100
 621  L  V  G  N  A  I  K  F  T  T  K  G  H  V  L  I  S  C  D  S   640

2101 CGAAAAATTACGGACGACAGATTTGAGATCAATGTGTCAGTTGAGGATTCAGGAATTGGA 2160
 641  R  K  I  T  D  D  R  F  E  I  N  V  S  V  E  D  S  G  I  G   660

2161 ATTTCCAAAAAATCTCAAAATAAAGTGTTTGGAGCATTTTCTCAAGTAGATGGTTCCGCA 2220
 661  I  S  K  K  S  Q  N  K  V  F  G  A  F  S  Q  V  D  G  S  A   680

2221 AGACGAGAATATGGTGGCTCTGGATTAGGTTTAGCTATATCAAAGAAATTGACTGAACTA 2280
 681  R  R  E  Y  G  G  S  G  L  G  L  A  I  S  K  K  L  T  E  L   700

2281 ATGGGTGGCACAATTAGATTTGAAAGTGAGGAAGGGATTGGCACAACGTTTTATGTTAGC 2340
 701  M  G  G  T  I  R  F  E  S  E  E  G  I  G  T  T  F  Y  V  S   720

2341 GTCATTATGGACGCAAAAGAATACTCATCCCCGCCATTTAGTTTAAATAAAAAATGTTTG 2400
 721  V  I  M  D  A  K  E  Y  S  S  P  P  F  S  L  N  K  K  C  L   740

2401 ATTTACAGCCAGCATTGTCTTACTGCCAAGTCAATTTCAAATATGCTTAATTATTTTGGA 2460
 741  I  Y  S  Q  H  C  L  T  A  K  S  I  S  N  M  L  N  Y  F  G   760

2461 TCAACAGTTAAAGTCACTAATCAGAAGTCTGAGTTTTCAACTTCCGTGCAAGCCAACGAC 2520
 761  S  T  V  K  V  T  N  Q  K  S  E  F  S  T  S  V  Q  A  N  D   780

2521 ATCATTTTTGTTGATCGCGGAATGGAACCTGATGTTAGTTGCAAAACCAAAATCATTCCC 2580
 781  I  I  F  V  D  R  G  M  E  P  D  V  S  C  K  T  K  I  I  P   800

2581 ATCGACCCAAAACCTTTCAAAAGAAACAAACTCATTAGTATTCTCAAAGAACAACCAAGT 2640
 801  I  D  P  K  P  F  K  R  N  K  L  I  S  I  L  K  E  Q  P  S   820
```

FIG. 2C

```
2641 TTGCCCACCAAAGTGTTTGGAAACAACAAATCTAATTTATCAAAACAATACCCTCTAAGA 2700
 821  L  P  T  K  V  F  G  N  N  K  S  N  L  S  K  Q  Y  P  L  R   840

2701 ATATTATTAGCAGAAGACAATCTTTTGAACTATAAAGTATGTTTGAAGCATTTGGATAAA 2760
 841  I  L  L  A  E  D  N  L  L  N  Y  K  V  C  L  K  H  L  D  K   860

2761 TTGGGGTACAAGGCAGATCATGCCAAAGATGGAGTAGTAGTTTTGGATAAATGTAAAGAA 2820
 861  L  G  Y  K  A  D  H  A  K  D  G  V  V  V  L  D  K  C  K  E   880

2821 CTACTAGAAAAAGACGAAAAATATGATGTCATATTGATGGATATTCAAATGCCTCGTAAG 2880
 881  L  L  E  K  D  E  K  Y  D  V  I  L  M  D  I  Q  M  P  R  K   900

2881 GACGGTATTACAGCTACAAGGGATTTGAAAACATTGTTTCACACACAAAAAAAGGAAAGT 2940
 901  D  G  I  T  A  T  R  D  L  K  T  L  F  H  T  Q  K  K  E  S   920

2941 TGGTTACCCGTGATCGTAGCATTGACAGCTAATGTTGCTGGAGACGACAAAAAGAGGTGT 3000
 921  W  L  P  V  I  V  A  L  T  A  N  V  A  G  D  D  K  K  R  C   940

3001 CTAGAAGAGGGAATGTTTGATTTTATAACCAAACCCATTTTACCAGATGAACTTAGACGT 3060
 941  L  E  E  G  M  F  D  F  I  T  K  P  I  L  P  D  E  L  R  R   960

3061 ATTTTAACAAAAGTAGGGGAAACAGTGAATATGTAAAATGTGTATTTAATAATAAGATC 3119
 961  I  L  T  K  V  G  E  T  V  N  M                             971
```

FIG. 2D

| | | |
|---|---|---|
| CaHK | 498 | SKQYPLRILLAEDNLLNYKVCLKHLDKLGYKADHAKDG 535 |
| SHK1462 | 1185 | SLQPALQILLAEDNLVNQKVAHQMLNNLGYPVAIANNG 1222 |
| BarA | 663 | ESKLAMTVMAVDDNPANLKLIGALLEDMVQHVELCDSG 700 |
| LemA | 674 | LSSRAPRVLCVDDNPANLLLVQTLLEDMGAEVVAVEGG 711 |
| DokA | 1512 | QSQPKKYILVAEDNDINIKVVVRQLEKLGYTAIVGING 1549 |
| NIK-1 | 1081 | DNTKSFEILLAEDNTVNQRLAVKTLEXYHHVVTVVGNG 1118 |
| slnlp | 1083 | KNETSVXILVVEDNHVNQEVIYRMLNLEGGIENIELAC 1119 |
| | | ** * |

| | | |
|---|---|---|
| CaHK | 555 | ILMDIQMPRKDGITATRDLK 574 |
| SHK1462 | 1237 | VLMDMQMPVMDGITACRHIR 1256 |
| BarA | 715 | ILMDIQMPDMDGIRACELIH 741 |
| LemA | 726 | VLMDVQMPGMDGRQATEAIR 745 |
| DokA | 1564 | ILLDCQMPQMDGFTCSTIIR 1591 |
| Nik-1 | 1133 | ILMDVQMPIMGGFEATAKIP 1152 |
| Slnlp | 1141 | IPMDVQMPKVDGLLSTKMIR 1160 |
| | | * *** * |

| | | |
|---|---|---|
| CaHK | 585 | IVALTANVAGDDKKRCLEEGMFDFITKPILPDELRRIL 626 |
| SHK1462 | 1267 | IVAMTANAMPGDRQECLDAGMDGYXSKPISINQLRKVL 1304 |
| BarA | 744 | VIAVTAHAMAGQKEKLLGAGMSDYIJKPIEEERLHNLL 783 |
| LemA | 758 | IVALTAHAMANEXRSLLQSGMDDYLTKPISERQLAQVV 797 |
| DokA | 1591 | RIPIIAMTANDSKDRCFEVGMDDYLSKPVPVDRLQKTL 1628 |
| Nik-I | 1165 | IIALTAIAMMGDREKCIQAQMDEYLSKPLQQNHLIQTI 1202 |
| Slnlp | 1169 | IVALTAFADDSNIKECLESGMNGFLSKPIXRPKLKTIL 1206 |
| | | ** * ** * |

FIG. 3

```
AGATCTATATTGATTATGATAGCAAATTACAGTTCCTGATAACTCGTAGGTTTTTTTAAAAGTAGTAGA
GTATCGCCGAGTGAAAGTTGTCAGGAAAAATATTGGACAATTGATAACCAATATTCAGTGTCGTGCATT
TTTGTCATTAACTCAGCAATATACTAAAAAACTCTATATTTTTTGCAACTTGATCCCCCTCGAACATAA
GCAAGACCACGACAATAGCATAATTCAAATAGAAGAAGACTAGTTACTGGGATATGCAATAAATTTAA
GTACTAAATAGTGGCAAAAGTACAGAATTAGAAGAAAAATATGTAAAGACTTAGTATTTGTAAACACAA
TTGCGAGAAATCACTATTAATATGTTCAGAAATGGCAGTATCAAAAAAGTGCCGACTTCAAACAACCCC
AAGTTCAATCATCAATGTGTAACTAACATATTCGTCTTCTTTTGAAACTGTGTTTAAGAAGTCTTTGTG
GTATTACTAATCCAACCAAAACAGAGAATCCAGCCTCTTAGTAATCAAGCCAAAAAGCAACCAAGGCGG
CAAAAAAAAAACTCGCTTTCTAAGGCGGGCCACACTAAATAGATTGCTCATAGATTGTTTTTTTTTTG
ACCTTCCCAAAATTGATAATTAGCACCAAATATTTAGTCACATAAATCTTGAATGACAAGATATGAAAC
TGTTGCCTAATCGTTAAGAACATGGAGAAGTAAAATATTGAGAATTATTCGACTATATTGAAGATGTTG
TTTGGACTGAATTATAACTTCTAGACAATTTTTTTATTAAGGGTATCGGAAATTACCCACAAAATGCA
AACACCAAAAAGAACAAAATTAACAATACATACAATAAAATGCGTGGAAAATAAAAAAACGGTTTTTG
TGTTAGAAATAGCCATCGATAAACCTTCATGAATTATCATTAGTGAAAAGCAACCGTAAAATTAATT
TAAAACTTTTTTTTTAAAAGAAAAACTCCAAAGCTTTCTTCTTTTTTCTTTTAATAGGATTCGACTAAT
AGCCTTTTCTTACTTATTTGGTGCTACAGTATCTCTCACCTAACGTACAGACCTTTTACAGAATAGTT
TTTCAGTAAATCATGTCTATGAACTTTTTTAATTCAAGCGAACCTGCAAGGGACCACAAACCGGACCAG
GAAAAGGAAACAGTAATGACGACAGAACATTATGAATTTGAACGACCAGATGTCAAAGCTATACGAAAT
TTCAAATTCTTCAGGCTGGACGAAACAGAAACCAAAAAGGACCAAACCTTCATATTTCGGATCTATCC
CCTCTTGAATCACAATCTGTGCCCCCTTCAGCCTTAAGTTTAAATCATTCGATAATACCAGACCAATAT
GAACGACGTCAGGATACACCGGATCCTATACACACTCCTGAAATTTCATTAAGTGATTATTTATATGAT
CAGACATTGAGTCCCCAAGGTTTTGACAATAGCCGTGAAAATTTCAACATCCACAAAACAATCGCCAGT
TTATTCGAAGATAACTCATCTGtTGtATCACAAGAATCTACTGATGACACCAAGACAACATTATCACTG
GAAACATGTGATAGCTTTTCATTGAATAACGCATCATATTTGACCAACATTAACTTTGTGCAAAATCAT
TTACAATACcTTAGTCAAAATGTTTTGGGAAATCGCACTTCCAACAGCTTACCGCCATCATCATCATCA
CAGATAGACTTTGATGCCTCCAATTTGACACCCGATTCGATACCAGGGTACATTCTCAACAAGAAACTT
GGCTCTGTTCATCAACTGACAGACCTGGTATACAACGCTatCaaGATTCCTCAAAACGAAGAATACAAC
TGTTGCACTAAAGCTTCTGCTAGTCAAAATCCAACAAATTTGAATTCTAAAGTGATAGTGAGGCTATCA
CCTAATATTTTTCAAAACTTGTCACTTTCGCGTTTTCTTAATGAGTGGTACATATTATCTGGGAAGCAC
AGTTCAAAAGAGCACCAAATATGGTCCAATGAGTCTCTCACAAATGAATACGTACAAGACAAAACAATT
CCGACATTTGATAAAGAAAGTGCACGTTTTAGACCAACGTTGCCCATAAATATACCAGGTATCTTGTAC
CCGCAAGAGATAATAAACTTTTGTGTGAACAGCCATGATTATCCACTTGAACACCCATCACAGTCCACT
GATCAAAAAGATTTGCCATGGTGTACCAAGACAACGATTACAAGACATTCAAAGAACTCAGCATGTTC
ACTTTGCACGAGCTACAAACTAGACAGGGGTCGTATTCGTCCAACGAGTCACGACGAAAATCCAGCAGT
GGCTTTAATATAGGTGTCAATGCAACCACCACTGAAGCTGGGTCTTTGGAATCTTTTAGTAATCTAATG
CAGAATCACCATCTTGGTGCAACTTCAACCAACGGAGACCCATTTCACTCAAAACTAGCAAAGTTTGAG
TATGGAGTTTCCAAATCCCCTATGAAGCTTATAGAGATTTTGACTGATATAATGAGAGTTGTCGAGACA
ATAAGTGTTATTCATGAACTAGGATTTGTTCACAATGGCCTAACTAGCAGCAATTTATTGAAGTCAGAG
AAAAATGTCAGAGATATAAAAATAACAGGATGGGGGTTTGCATTCAGTTTTACTGAAAATTGCAGCCAG
GGTTACAGAAATAAACACTTGGCACAAGTCCAAGATTTAATACCTTACATGGCACCAGAGGTGTTGGCT
ATTACAAATTCGGTTGTGGATTATCGGTCGGACTTTTACTCGTTAGGGGTAATAATGTATGAGTTAGTT
TTGGGTATTTTGCCATTCAAAAATAGCAACCCCCAGAAATTGATCAGAATGCATACTTTTGAAAACCCA
ATAGCTCCCAGTGCTCTAGCACCAGGTTGGATTTCAGAGAATTGAGTGGCGTTATTATGAATTGTTA
GAGAAGCACCCACATAACAGATACACCGACTGCCACTCATTGCTCCACGATTTAATTGAAGTTAAAAAT
ATGTACATTAGCAAATTATTGGATTCAGGGGAAACAATCCCCAATAGTAACCTAAATTTAAGTGATCGC
CAGTACTATTTGACTAAAGAAAATTTACTTCATCCCGAGAAAATGGGAATTACTCCTGTACTTGGGTTG
AAAGAAAGTTTTATTGGAAGAAGAGATTTCTTGCAAAATGTTACTGAAGTTTACAATAACAGCAAAAAT
GGGATTGATTTACTTTTTATATCCGGTGAAAGCGGAAGAGGTAAAACGATAATATTACAAGATCTTCGA
GCAGCAGCAGTTTTGAAACAAGACTTTTATTACTCATGGAAGTTTAGTTTTTTTGGAGCAGATACACAT
GTGTACCGGTTTCTTGTTGAAGGTGTTCAAAAGATTATTACCCAGATTCTAAATTCTTCAGAAGAAATT
```

FIG. 4A

```
CAAAATACATGGAGAGATGTGATTTTGACACACATTCCTATAGATCTAAGCATATTATTTTATTTGATT
CCTGAGCTAAAAGTACTATTGGGGAAAAAATACACTTCCATTTACAAACATAAAATTGGAATGGGGATG
CTAAAGAGAAGTTTCAAAGAAGACCAAACACTGAGACTAGAGATTAAATTGAGACAAATACTAAAAGAA
TTTTTCAAACTTGTAGCGAAACAAGGCTTGTCTATTTTTTTAGATGATGTACAGTGGTGTTCAGAAGAG
TCCTGGAGGTTATTATGTGATGTATTAGATTTTGATTCATCTGGAGAGGTGCGAGAGAGCTATAACATC
AAAATAGTTGTGTGCTATGCTTTGAATGCAGACCATTTAGAGAATGTTAATATCGAGCATAAAAGATT
TCTTTTTGCCGATATGCCAAACAAAGCCACTTAAATTTGCGTGAGTTTAGTATACCTCATATCCCACTT
GAAGACGCTATTGAATTTTGTGTGAACCTTACACGAGACTGCACGATCATGAATGTAACAGTAAAAAG
TCTGATGTAATTGCCAATTTAAACTGCACAAATGAATATCCTCAGAACACTTGCAAAGTCATCCCCAGT
ATAATCCAAGAGTTGTATCAATCATCAGAAGGGAATGTTTTGCTTTTGATATTCCTAACAAGAATGACA
AAGCTATCTGGCAAAGTTCCCTTTCAACGATTTTCGGTCAAAAATTCATATCTATATGATCACCTACTG
AATAGTAACTATGGAACTACAAGAAAAGAGATTCTTACAAATTATTTGAATATGGGAACTAACTCAGAC
ACAAGAGCCTTGCTTAAAGTTGCAGCGTTAATCTCCAATGGATCGGGATTCTTTTTTTCAGATTTAATT
GTAGCCACCGACTTGCCCATGGCTGAAGCGTTTCAGTTGTTACAAATATGTATTCATTCCAGAATAATT
GTTCCTACTAGCACATATTATAAAATACCTATGGATTTAATAGCCTCTGACCAGACTCCATTTGATTTA
ACAGATGATAATATTTGGAAACTAGCCACTTTATGCAGCTACAAGTTCTATCATGATTCTATTTGTACT
CATATAATCAAAGAATTAAACGCCAGTGGCGAATTCAAAGAACTTTCTCGGTTATGTGGGTTGAGATTT
TACAATACAATTACAAAAGAACGTTTATTAAATATTGGTGGCTATCTTCAAATGGCTACTCACTTTAGA
AACTCATACGAGGTGGCAGGTCCCGAAGAAAATGAAAGTATGTTGAAGTTTTGGTCCAGGCAGGACGA
TATGCCATATCGACATATAATATGAAGTTGTCTCAATGGTTTTTCAATGTTGTTGGCGAATTGGTATAT
AATCTTGATTCGAAAACTCAGTTAAAATCCGTGTTAACAATAGCCGAGAATCATTTTAATTCTCGTGAA
TTTGAACAATGCCTAAGTGTGGTTGAAAATGCACAGAGGAAATTTGGTTTTGACAGGTTGATATTTTCC
ATTCAAATAGTCCGTTGCAAAATTGAATTAGGTGATTATGACGAAGCACATCGAATTGCAATTGAATGT
CTTAAGGAATTAGGTGTTCCATTAGATGACGATGACGAATATACAAGTGAAAACCTGCTTGAGACGTGT
TTGGGAAAAATTCCGCTCTCTGTTGCTGACATTAGAGGTATTTTGAAGATTAAAAGATGCAAGAATTCA
AGAACATTGCTAATGTATCAGTTAATTTCAGAGCTAATTGTACTATTCAAGCTTCAAGGTAAAGACAAA
GTGAGAAGGTTTCTCACAGCTTATGCGATGAGTCAAATTCATACTCAAGGGTCTTCTCCTTATTGTGCA
GTAATTCTTATAGACTTTGCACAATCATTTGTCAACGAAACCACAACTTCAGGAATGCTTAAAGCAAAA
GAACTCAGTATTGTCATGTTGTCATTGATTAATAGAGCACCAGAAATATCTTTATCATATGTTCAGTCT
ATTTATGAATATTATTTCAGTTGTCATGCTGTATTTTTGAATCAATTGAAAAAATGCTGGATCTTATA
CATCCAGGTAACGCTAGTTCCCATTGCACAAGACTGTCTTATTATTCATCTTTTCATTTGATAGTTAAT
GTTTCCAAGATTTTCTTTTCATGTATGAATGGAGAAAGTTTCAAAATGTTCTCAACATTCAAGTGTAAA
TCCTATTTAACAGGGGATCCCCAAATGCCTGAAATGGACAATTTTTTATACGATAGTGAAATGTTACTT
GCTGGACATTCAGAATTGAATGAATTTATGAGAAAATATCAGTCATTCAACCAAACTTCCGTTGGTAAA
TTTTGCTACTATTTAATTGTACTACTTGTAATGTCACGTGAACACAGATTTGACGAGGCTGCCGATTTG
GTTTTGAAAGTTTTGGAAGACTTACTGGAAAAATTGCCTGTATCTTTTTGCATCATCAATATTACTTA
ATATGTGGTAAAGTGTTTGCTTATCACCAGACCAAAACCCCAGAAAGTGAGGAACAAGTGGAACGTATT
TTGGCTCGTCAATTTGAAAGATATGAATTGTGGGCACTGACGAATAAGCCGACCCTTCTACCACGGTAC
TTGTTGTTGAGTACCTACAAACAGATTAGAGAAACCATGTTGACAAGTTAGAAATACTAGATTCATTT
GAGGAGGCGTTACAGACGGCCCATAAATTTCATAATGTATATGATATGTGCTGGATCAATTTGGAATGT
GCAAGATGGTTAATTAGCATAAACCAAAAAGGCACAGAATCTCAAGAATGGTTAAACAAGGTCTTAAA
ATTTTGAGAAGCTTGGAATTAAATAATCATTTAAGATTAGCTGAATTTGAATTTGATGAATACATTGAG
GACGAAGATCACAGAAATAAATGGGCAGGGTTAACTAATAATCCAACATTGGATACTGTTACTACCTGG
CAACAACAGAACATGCCCGATAAGGTATCTCCATGCAATGACAAGCAGTTGGTCCACGGAAAACAATTT
GGCAAAAAGAGTTTGATAGCCATTTGCTCAGATTGCACTTTGATGGCCAATATACAGGCCTAGATTTG
AATTCAGCTATTCGTGAATGTCTAGCAATATCCGAAGCTTTAGACGAAAATTCCATTCTCACAAAGTTG
ATGGCATCTGCCATCAAGTATTCAGGTGCCACATATGGGGTAATTGTCACGAAGAAAACCAGGAGACA
CCTTTTCTTAGAACAATTGGCTCGCAGCACAATATTCACACATTAAACAACATGCCAATTTCCGACGAC
ATTTGTCCTGCTCAGTTGATTCGTCATGTATTGCATACAGGAGAAACGGTGAACAAAGCTCATGATCAC
ATAGGATTTGCTAACAAGTTTGAGAATGAATACTTTCAAACAACAGATAAAAAGTATTCAGTTGTGTGT
TTGCCATTAAAGAGTCTGCTTGGATTATTTGGTGCACTTTATCTAGAAGGTAGTGATGGTGATTTTGGA
```

FIG. 4B

```
CATGAAGATTTGTTCAATGAAAGGAAATGTGATTTGTTACAACTTTTTTGCACACAAGCAGCTGTGGCT
TTGGGTAAGGAGCGTTTGCTTTTGCAAATGGAACTAGCAAAAATGGCAGCAGAAGACGCCACTGATGAA
AAAGCCAGTTTTTTGGCAAACATGTCACATGAAATACGAACCCCATTCAATTCGTTATTGTCATTTGCT
ATTTTTTTGTTAGATACCAAATTGGATTCTACTCAAAGAGAATATGTCGAGGCAATTCAGAGCTCCGCA
ATGATAACGTTGAATATTATTGATGGGATACTTGCGTTTTCCAAAATTGAGCATGGATCCTTTACATTA
GAAAATGCCCCCTTTTCTTTGAATGATTGTATCGAGACTGCTATTCAAGTAAGTGGGGAAACAATTTTG
AATGACCAGATTGAGTTGGTGTTTTGTAACAATTGTCCAGAGATTGAATTTGTGGTTGGTGATCTAACG
AGGTTCAGACAAATTGTGATCAATTTGGTGGGTAATGCTATTAAGTTTACAACCAAAGGTCATGTTTTG
ATTTCTTGTGATAGCCGAAAAATTACGGACGACAGATTTGAGATCAATGTGTCAGTTGAGGATTCAGGA
ATTGGAATTTCCAAAAAATCTCAAAATAAAGTGTTTGGAGCATTTTCTCAAGTAGATGGTTCCGCAAGA
CGAGAATATGGTGGCTCTGGATTAGGTTTAGCTATATCAAAGAAATTGACTGAACTAATGGGTGGCACA
ATTAGATTTGAAAGTGAGGAAGGGATTGGCACAACGTTTTATGTTAGCGTCATTATGGACGCAAAAGAA
TACTCATCCCCGCCATTTAGTTTAAATAAAAAATGTTTGATTTACAGCCAGCATTGTCTTACTGCCAAG
TCAATTTCAAATATGCTTAATTATTTTGGATCAACAGTTAAAGTCACTAATCAGAAGTCTGAGTTTTCA
ACTTCCGTGCAAGCCAACGACATCATTTTTGTTGATCGCGGAATGGAACCTGATGTTAGTTGCAAAACC
AAAATCATTCCCATCGACCCAAAACCTTTCAAAAGAAACAAACTCATTAGTATTCTCAAAGAACAACCA
AGTTTGCCCACCAAAGTGTTTGGAAACAACAAATCTAATTTATCAAAACAATACCCTCTAAGAATATTA
TTAGCAGAAGACAATCTTTTGAACTATAAAGTATGTTTGAAGCATTTGGATAAATTGGGGTACAAGGCA
GATCATGCCAAAGATGGAGTAGTAGTTTTGGATAAATGTAAAGAACTACTAGAAAAAGACGAAAATAT
GATGTCATATTGATGGATATTCAAATGCCTCGTAAGGACGGTATTACAGCTACAAGGGATTTGAAAACA
TTGTTTCACACACAAAAAAAGGAAAGTTGGTTACCCGTGATCGTAGCATTGACAGCTAATGTTGCTGGA
GACGACAAAAAGAGGTGTCTAGAAGAGGGAATGTTTGATTTTATAACCAAACCCATTTTACCAGATGAA
CTTAGACGTATTTTAACAAAAGTAGGGGAAACAGTGAATATGTAAAATGTGTATTTAATAATAAGATCT
```

FIG. 4C

```
MSMNFFNSSEPARDHKPDQEKETVMTTEHYEFERPDVKAIRNFKFFRLDETETKKGPNLHISDLSPLES
QSVPPSALSLNHSIIPDQYERRQDTPDPIHTPEISLSDYLYDQTLSPQGFDNSRENFNIHKTIASLFED
NSSVVSQESTDDTKTTLSLETCDSFSLNNASYLTNINFVQNHLQYLSQNVLGNRTSNSLPPSSSSQIDF
DASNLTPDSIPGYILNKKLGSVHQLTDLVYNAIKIPQNEEYNCCTKASASQNPTNLNSKVIVRLSPNIF
QNLSLSRFLNEWYILSGKHSSKEHQIWSNESLTNEYVQDKTIPTFDKESARFRPTLPINIPGILYPQEI
INFCVNSHDYPLEHPSQSTDQKRFAMVYQDNDYKTFKELSMFTLHELQTRQGSYSSNESRRKSSSGFNI
GVNATTTEAGSLESFSNLMQNHHLGATSTNGDPFHSKLAKFEYGVSKSPMKLIEILTDIMRVVETISVI
HELGFVHNGLTSSNLLKSEKNVRDIKITGWGFAFSFTENCSQGYRNKHLAQVQDLIPYMAPEVLAITNS
VVDYRSDFYSLGVIMYELVLGILPFKNSNPQKLIRMHTFENPIAPSALAPGWISEKLSGVIMKLLEKHP
HNRYTDCHSLLHDLIEVKNMYISKLLDSGETIPNSNLNLSDRQYYLTKENLLHPEKMGITPVLGLKESF
IGRRDFLQNVTEVYNNSKNGIDLLFISGESGRGKTIILQDLRAAAVLKQDFYYSWKFSFFGADTHVYRF
LVEGVQKIITQILNSSEEIQNTWRDVILTHIPIDLSILFYLIPELKVLLGKKYTSIYKHKIGMGMLKRS
FKEDQTLRLEIKLRQILKEFFKLVAKQGLSIFLDDVQWCSEESWRLLCDVLDFDSSGEVRESYNIKIVV
CYALNADHLENVNIEHKKISFCRYAKQSHLNLREFSIPHIPLEDAIEFLCEPYTRLHDHECNSKKSDVI
ANLNCTNEYPQNTCKVIPSIIQELYQSSEGNVLLLIFLTRMTKLSGKVPFQRFSVKNSYLYDHLLNSNY
GTTRKEILTNYLNMGTNSDTRALLKVAALISNGSGFFFSDLIVATDLPMAEAFQLLQICIHSRIIVPTS
TYYKIPMDLIASDQTPFDLTDDNIWKLATLCSYKFYHDSICTHIIKELNASGEFKELSRLCGLRFYNTI
TKERLLNIGGYLQMATHFRNSYEVAGPEENEKYVEVLVQAGRYAISTYNMKLSQWFFNVVGELVYNLDS
KTQLKSVLTIAENHFNSREFEQCLSVVENAQRKFGFDRLIFSIQIVRCKIELGDYDEAHRIAIECLKEL
GVPLDDDDEYTSENLLETCLGKIPLSVADIRGILKIKRCKNSRTLLMYQLISELIVLFKLQGKDKVRRF
LTAYAMSQIHTQGSSPYCAVILIDFAQSFVNETTTSGMLKAKELSIVMLSLINRAPEISLSYVQSIYEY
YFSCHAVFFESIEKMLDLIHPGNASSHCTRLSYYSSFHLIVNVSKIFFSCMNGESFKMFSTFKCKSYLT
GDPQMPEMDNFLYDSEMLLAGHSELNEFMRKYQSFNQTSVGKFCYYLIVLLVMSREHRFDEAADLVLKV
LEDLLEKLPVSFLHHQYYLICGKVFAYHQTKTPESEEQVERILARQFERYELWALTNKPTLLPRYLLLS
TYKQIRENHVDKLEILDSFEEALQTAHKFHNVYDMCWINLECARWLISINQKRHRISRMVKQGLKILRS
LELNNHLRLAEFEFDEYIEDEDHRNKWAGLTNNPTLDTVTTWQQQNMPDKVSPCNDKQLVHGKQFGKKE
FDSHLLRLHFDGQYTGLDLNSAIRECLAISEALDENSILTKLMASAIKYSGATYGVIVTKKNQETPFLR
TIGSQHNIHTLNNMPISDDICPAQLIRHVLHTGETVNKAHDHIGFANKFENEYFQTTDKKYSVVCLPLK
SLLGLFGALYLEGSDGDFGHEDLFNERKCDLLQLFCTQAAVALGKERLLLQMELAKMAAEDATDEKASF
LANMSHEIRTPFNSLLSFAIFLLDTKLDSTQREYVEAIQSSAMITLNIIDGILAFSKIEHGSFTLENAP
FSLNDCIETAIQVSGETILNDQIELVFCNNCPEIEFVVGDLTRFRQIVINLVGNAIKFTTKGHVLISCD
SRKITDDRFEINVSVEDSGIGISKKSQNKVFGAFSQVDGSARREYGGSGLGLAISKKLTELMGGTIRFE
SEEGIGTTFYVSVIMDAKEYSSPPFSLNKKCLIYSQHCLTAKSISNMLNYFGSTVKVTNQKSEFSTSVQ
ANDIIFVDRGMEPDVSCKTKIIPIDPKPFKRNKLISILKEQPSLPTKVFGNNKSNLSKQYPLRILLAED
NLLNYKVCLKHLDKLGYKADHAKDGVVVLDKCKELLEKDEKYDVILMDIQMPRKDGITATRDLKTLFHT
QKKESWLPVIVALTANVAGDDKKRCLEEGMFDFITKPILPDELRRILTKVGETVNM
```

FIG. 4D

```
  1  AGATCTATATTGATTATGATAGCAAATTACAGTTCCTGATAACTCGTAGGTTTTTTTAAA   60

61  AGTAGTAGAGTATCGCCGAGTGAAAGTTGTCAGGAAAAATATTGGACAATTGATAACCAA  120

121  TATTCAGTGTCGTGCATTTTTGTCATTAACTCAGCAATATACTAAAAAACTCTATATTTT  180

181  TTGCAACTTGATCCCCCTCGAACATAAGCAAGACCACGACAATAGCATAATTCAAATAGA  240

241  AAGAAGACTAGTTACTGGGATATGCAATAAATTTAAGTACTAAATAGTGGCAAAAGTACA  300

301  GAATTAGAAGAAAAATATGTAAAGACTTAGTATTTGTAAACACAATTGCGAGAAATCACT  360

361  ATTAATATGTTCAGAAATGGCAGTATCAAAAAAGTGCCGACTTCAAACAACCCCAAGTTC  420

421  AATCATCAATGTGTAACTAACATATTCGTCTTCTTTTGAAACTGTGTTTAAGAAGTCTTT  480

481  GTGGTATTACTAATCCAACCAAAACAGAGAATCCAGCCTCTTAGTAATCAAGCCAAAAG   540

541  CAACCAAGGCGGCAAAAAAAAAACTCGCTTTCTAAGGCGGGCCACACTAAATAGATTGCT  600

601  CATAGATTGTTTTTTTTTTTGACCTTCCCAAAATTGATAATTAGCACCAAATATTTAGTC  660

661  ACATAAATCTTGAATGACAAGATATGAAACTGTTGCCTAATCGTTAAGAACATGGAGAAG  720

721  TAAAATATTGAGAATTATTCGACTATATTGAAGATGTTGTTTGGACTGAATTATAACTTC  780

781  TAGACAATTTTTTTTATTAAGGGTATCGGAAATTACCCACAAAATGCAAACACCAAAAAA  840

841  GAACAAAATTAACAATACATACAATAAAATGCGTGGAAAATAAAAAAACGGTTTTTGTGT  900

901  TAGAAATAGCCATCGATAAACCTTCATGAATTATCATTAGTGAAAAAGCAACCGTAAAAA  960

961  TTAATTTAAAACTTTTTTTTAAAAGAAAAACTCCAAAGCTTTCTTCTTTTTCTTTTAA   1020

1021 TAGGATTCGACTAATAGCCTTTTCTTACTTATTTTGGTGCTACAGTATCTCTCACCTAAC 1080

1081 GTACAGACCTTTTACAGAATAGTTTTTCAGTAAATCATGTCTATGAACTTTTTTAATTCA 1140
   1                                        M  S  M  N  F  F  N  S    8

1141 AGCGAACCTGCAAGGGACCACAAACCGGACCAGGAAAAGGAAACAGTAATGACGACAGAA 1200
   9  S  E  P  A  R  D  H  K  P  D  Q  E  K  E  T  V  M  T  T  E    28
```

FIG. 5A

```
1201  CATTATGAATTTGAACGACCAGATGTCAAAGCTATACGAAATTTCAAATTCTTCAGGCTG  1260
  29    H   Y   E   F   E   R   P   D   V   K   A   I   R   N   F   K   F   F   R   L    48

1261  GACGAAACAGAAACCAAAAAAGGACCAAACCTTCATATTTCGGATCTATCCCCTCTTGAA  1320
  49    D   E   T   E   T   K   K   G   P   N   L   H   I   S   D   L   S   P   L   E    68

1321  TCACAATCTGTGCCCCCTTCAGCCTTAAGTTTAAATCATTCGATAATACCAGACCAATAT  1380
  69    S   Q   S   V   P   P   S   A   L   S   L   N   H   S   I   I   P   D   Q   Y    88

1381  GAACGACGTCAGGATACACCGGATCCTATACACACTCCTGAAATTTCATTAAGTGATTAT  1440
  89    E   R   R   Q   D   T   P   D   P   I   H   T   P   E   I   S   L   S   D   Y   108

1441  TTATATGATCAGACATTGAGTCCCCAAGGTTTTGACAATAGCCGTGAAAATTTCAACATC  1500
 109    L   Y   D   Q   T   L   S   P   Q   G   F   D   N   S   R   E   N   F   N   I   128

1501  CACAAAACAATCGCCAGTTTATTCGAAGATAACTCATCTGtTGtATCACAAGAATCTACT  1560
 129    H   K   T   I   A   S   L   F   E   D   N   S   S   V   V   S   Q   E   S   T   148

1561  GATGACACCAAGACAACATTATCACTGGAAACATGTGATAGCTTTTCATTGAATAACGCA  1620
 149    D   D   T   K   T   T   L   S   L   E   T   C   D   S   F   S   L   N   N   A   168

1621  TCATATTTGACCAACATTAACTTTGTGCAAAATCATTTACAATACcTTAGTCAAAATGTT  1680
 169    S   Y   L   T   N   I   N   F   V   Q   N   H   L   Q   Y   L   S   Q   N   V   188

1681  TTGGGAAATCGCACTTCCAACAGCTTACCGCCATCATCATCATCACAGATAGACTTTGAT  1740
 189    L   G   N   R   T   S   N   S   L   P   P   S   S   S   Q   I   D   F   D   208

1741  GCCTCCAATTTTGACACCCGATTCGATACCAGGGTACATTCTCAACAAGAAACTTGGCTCT  1800
 209    A   S   N   L   T   P   D   S   I   P   G   Y   I   L   N   K   K   L   G   S   228

1801  GTTCATCAACTGACAGACCTGGTATACAACGCTatCaaGATTCCTCAAAACGAAGAATAC  1860
 229    V   H   Q   L   T   D   L   V   Y   N   A   I   K   I   P   Q   N   E   E   Y   248

1861  AACTGTTGCACTAAAGCTTCTGCTAGTCAAAATCCAACAAATTTGAATTCTAAAGTGATA  1920
 249    N   C   C   T   K   A   S   A   S   Q   N   P   T   N   L   N   S   K   V   I   268

1921  GTGAGGCTATCACCTAATATTTTTCAAAACTTGTCACTTTCGCGTTTTCTTAATGAGTGG  1980
 269    V   R   L   S   P   N   I   F   Q   N   L   S   L   S   R   F   L   N   E   W   288

1981  TACATATTATCTGGGAAGCACAGTTCAAAAGAGCACCAAATATGGTCCAATGAGTCTCTC  2040
 289    Y   I   L   S   G   K   H   S   S   K   E   H   Q   I   W   S   N   E   S   L   308

2041  ACAAATGAATACGTACAAGACAAAACAATTCCGACATTTGATAAAGAAAGTGCACGTTTT  2100
 309    T   N   E   Y   V   Q   D   K   T   I   P   T   F   D   K   E   S   A   R   F   328
```

FIG. 5B

```
2101  AGACCAACGTTGCCCATAAATATACCAGGTATCTTGTACCCGCAAGAGATAATAAACTTT  2160
 329   R   P   T   L   P   I   N   I   P   G   I   L   Y   P   Q   E   I   I   N   F    348

2161  TGTGTGAACAGCCATGATTATCCACTTGAACACCCATCACAGTCCACTGATCAAAAAGA  2220
 349   C   V   N   S   H   D   Y   P   L   E   H   P   S   Q   S   T   D   Q   K   R    368

2221  TTTGCCATGGTGTACCAAGACAACGATTACAAGACATTCAAAGAACTCAGCATGTTCACT  2280
 369   F   A   M   V   Y   Q   D   N   D   Y   K   T   F   K   E   L   S   M   F   T    388

2281  TTGCACGAGCTACAAACTAGACAGGGGTCGTATTCGTCCAACGAGTCACGACGAAAATCC  2340
 389   L   H   E   L   Q   T   R   Q   G   S   Y   S   S   N   E   S   R   R   K   S    408

2341  AGCAGTGGCTTTAATATAGGTGTCAATGCAACCACCACTGAAGCTGGGTCTTTGGAATCT  2400
 409   S   S   G   F   N   I   G   V   N   A   T   T   T   E   A   G   S   L   E   S    428

2401  TTTAGTAATCTAATGCAGAATCACCATCTTGGTGCAACTTCAACCAACGGAGACCCATTT  2460
 429   F   S   N   L   M   Q   N   H   H   L   G   A   T   S   T   N   G   D   P   F    448

2461  CACTCAAAACTAGCAAAGTTTGAGTATGGAGTTTCCAAATCCCCTATGAAGCTTATAGAG  2520
 449   H   S   K   L   A   K   F   E   Y   G   V   S   K   S   P   M   K   L   I   E    468

2521  ATTTTGACTGATATAATGAGAGTTGTCGAGACAATAAGTGTTATTCATGAACTAGGATTT  2580
 469   I   L   T   D   I   M   R   V   V   E   T   I   S   V   I   H   E   L   G   F    488

2581  GTTCACAATGGCCTAACTAGCAGCAATTTATTGAAGTCAGAGAAAAATGTCAGAGATATA  2640
 489   V   H   N   G   L   T   S   S   N   L   L   K   S   E   K   N   V   R   D   I    508

2641  AAAATAACAGGATGGGGGTTTGCATTCAGTTTTACTGAAAATTGCAGCCAGGGTTACAGA  2700
 509   K   I   T   G   W   G   F   A   F   S   F   T   E   N   C   S   Q   G   Y   R    528

2701  AATAAACACTTGGCACAAGTCCAAGATTTAATACCTTACATGGCACCAGAGGTGTTGGCT  2760
 529   N   K   H   L   A   Q   V   Q   D   L   I   P   Y   M   A   P   E   V   L   A    548

2761  ATTACAAATTCGGTTGTGGATTATCGGTCGGACTTTTACTCGTTAGGGGTAATAATGTAT  2820
 549   I   T   N   S   V   V   D   Y   R   S   D   F   Y   S   L   G   V   I   M   Y    568

2821  GAGTTAGTTTTGGGTATTTTGCCATTCAAAAATAGCAACCCCCAGAAATTGATCAGAATG  2880
 569   E   L   V   L   G   I   L   P   F   K   N   S   N   P   Q   K   L   I   R   M    588

2881  CATACTTTTGAAAACCCAATAGCTCCCAGTGCTCTAGCACCAGGTTGGATTTCAGAGAAA  2940
 589   H   T   F   E   N   P   I   A   P   S   A   L   A   P   G   W   I   S   E   K    608

2941  TTGAGTGGCGTTATTATGAAATTGTTAGAGAAGCACCCACATAACAGATACACCGACTGC  3000
 609   L   S   G   V   I   M   K   L   L   E   K   H   P   H   N   R   Y   T   D   C    628
```

FIG. 5C

```
3001 CACTCATTGCTCCACGATTTAATTGAAGTTAAAAATATGTACATTAGCAAATTATTGGAT 3060
 629  H  S  L  L  H  D  L  I  E  V  K  N  M  Y  I  S  K  L  L  D   648

3061 TCAGGGGAAACAATCCCCAATAGTAACCTAAATTTAAGTGATCGCCAGTACTATTTGACT 3120
 649  S  G  E  T  I  P  N  S  N  L  N  L  S  D  R  Q  Y  Y  L  T   668

3121 AAAGAAAATTTACTTCATCCCGAGAAAATGGGAATTACTCCTGTACTTGGGTTGAAAGAA 3180
 669  K  E  N  L  H  P  E  K  M  G  I  T  P  V  L  G  L  K  E      688

3181 AGTTTTATTGGAAGAAGAGATTTCTTGCAAAATGTTACTGAAGTTTACAATAACAGCAAA 3240
 689  S  F  I  G  R  R  D  F  L  Q  N  V  T  E  V  Y  N  N  S  K   708

3241 AATGGGATTGATTTACTTTTTATATCCGGTGAAAGCGGAAGAGGTAAAACGATAATATTA 3300
 709  N  G  I  D  L  L  F  I  S  G  E  S  G  R  G  K  T  I  I  L   728

3301 CAAGATCTTCGAGCAGCAGCAGTTTTGAAACAAGACTTTTATTACTCATGGAAGTTTAGT 3360
 729  Q  D  L  R  A  A  A  V  L  K  Q  D  F  Y  Y  S  W  K  F  S   748

3361 TTTTTTGGAGCAGATACACATGTGTACCGGTTTCTTGTTGAAGGTGTTCAAAAGATTATT 3420
 749  F  F  G  A  D  T  H  V  Y  R  F  L  V  E  G  V  Q  K  I  I   768

3421 ACCCAGATTCTAAATTCTTCAGAAGAAATTCAAAATACATGGAGAGATGTGATTTTGACA 3480
 769  T  Q  I  L  N  S  S  E  E  I  Q  N  T  W  R  D  V  I  L  T   788

3481 CACATTCCTATAGATCTAAGCATATTATTTTATTTGATTCCTGAGCTAAAAGTACTATTG 3540
 789  H  I  P  I  D  L  S  I  L  F  Y  L  I  P  E  L  K  V  L  L   808

3541 GGGAAAAAATACACTTCCATTTACAAACATAAAATTGGAATGGGGATGCTAAAGAGAAGT 3600
 809  G  K  K  Y  T  S  I  Y  K  H  K  I  G  M  G  M  L  K  R  S   828

3601 TTCAAAGAAGACCAAACACTGAGACTAGAGATTAAATTGAGACAAATACTAAAAGAATTT 3660
 829  F  K  E  D  Q  T  L  R  L  E  I  K  L  R  Q  I  L  K  E  F   848

3661 TTCAAACTTGTAGCGAAACAAGGCTTGTCTATTTTTTTAGATGATGTACAGTGGTGTTCA 3720
 849  F  K  L  V  A  K  Q  G  L  S  I  F  L  D  D  V  Q  W  C  S   868

3721 GAAGAGTCCTGGAGGTTATTATGTGATGTATTAGATTTTGATTCATCTGGAGAGGTGCGA 3780
 869  E  E  S  W  R  L  L  C  D  V  L  D  F  D  S  S  G  E  V  R   888

3781 GAGAGCTATAACATCAAAATAGTTGTGTGCTATGCTTTGAATGCAGACCATTTAGAGAAT 3840
 889  E  S  Y  N  I  K  I  V  V  C  Y  A  L  N  A  D  H  L  E  N   908

3841 GTTAATATCGAGCATAAAAAGATTTCTTTTTGCCGATATGCCAAACAAAGCCACTTAAAT 3900
 909  V  N  I  E  H  K  K  I  S  F  C  R  Y  A  K  Q  S  H  L  N   928
```

FIG. 5D

```
3901  TTGCGTGAGTTTAGTATACCTCATATCCCACTTGAAGACGCTATTGAATTTTTGTGTGAA  3960
 929   L  R  E  F  S  I  P  H  I  P  L  E  D  A  I  E  F  L  C  E    948

3961  CCTTACACGAGACTGCACGATCATGAATGTAACAGTAAAAAGTCTGATGTAATTGCCAAT  4020
 949   P  Y  T  R  L  H  D  H  E  C  N  S  K  K  S  D  V  I  A  N    968

4021  TTAAACTGCACAAATGAATATCCTCAGAACACTTGCAAAGTCATCCCCAGTATAATCCAA  4080
 969   L  N  C  T  N  E  Y  P  Q  N  T  C  K  V  I  P  S  I  I  Q    988

4081  GAGTTGTATCAATCATCAGAAGGGAATGTTTTGCTTTTGATATTCCTAACAAGAATGACA  4140
 989   E  L  Y  Q  S  S  E  G  N  V  L  L  I  F  L  T  R  M  T     1008

4141  AAGCTATCTGGCAAAGTTCCCTTTCAACGATTTTCGGTCAAAAATTCATATCTATATGAT  4200
1009   K  L  S  G  K  V  P  F  Q  R  F  S  V  K  N  S  Y  L  Y  D   1028

4201  CACCTACTGAATAGTAACTATGGAACTACAAGAAAAGAGATTCTTACAAATTATTTGAAT  4260
1029   H  L  L  N  S  N  Y  G  T  T  R  K  E  I  L  T  N  Y  L  N   1048

4261  ATGGGAACTAACTCAGACACAAGAGCCTTGCTTAAAGTTGCAGCGTTAATCTCCAATGGA  4320
1049   M  G  T  N  S  D  T  R  A  L  L  K  V  A  A  L  I  S  N  G   1068

4321  TCGGGATTCTTTTTTTCAGATTTAATTGTAGCCACCGACTTGCCCATGGCTGAAGCGTTT  4380
1069   S  G  F  F  F  S  D  L  I  V  A  T  D  L  P  M  A  E  A  F   1088

4381  CAGTTGTTACAAATATGTATTCATTCCAGAATAATTGTTCCTACTAGCACATATTATAAA  4440
1089   Q  L  L  Q  I  C  I  H  S  R  I  I  V  P  T  S  T  Y  Y  K   1108

4441  ATACCTATGGATTTAATAGCCTCTGACCAGACTCCATTTGATTTAACAGATGATAATATT  4500
1109   I  P  M  D  L  I  A  S  D  Q  T  P  F  D  L  T  D  D  N  I   1128

4501  TGGAAACTAGCCACTTTATGCAGCTACAAGTTCTATCATGATTCTATTTGTACTCATATA  4560
1129   W  K  L  A  T  L  C  S  Y  K  F  Y  H  D  S  I  C  T  H  I   1148

4561  ATCAAAGAATTAAACGCCAGTGGCGAATTCAAAGAACTTTCTCGGTTATGTGGGTTGAGA  4620
1149   I  K  E  L  N  A  S  G  E  F  K  E  L  S  R  L  C  G  L  R   1168

4621  TTTTACAATACAATTACAAAAGAACGTTTATTAAATATTGGTGGCTATCTTCAAATGGCT  4680
1169   F  Y  N  T  I  T  K  E  R  L  L  N  I  G  G  Y  L  Q  M  A   1188

4681  ACTCACTTTAGAAACTCATACGAGGTGGCAGGTCCCGAAGAAAATGAAAAGTATGTTGAA  4740
1189   T  H  F  R  N  S  Y  E  V  A  G  P  E  E  N  E  K  Y  V  E   1208

4741  GTTTTGGTCCAGGCAGGACGATATGCCATATCGACATATAATATGAAGTTGTCTCAATGG  4800
1209   V  L  V  Q  A  G  R  Y  A  I  S  T  Y  N  M  K  L  S  Q  W   1228
```

FIG. 5E

```
4801 TTTTTCAATGTTGTTGGCGAATTGGTATATAATCTTGATTCGAAAACTCAGTTAAAATCC 4860
1229  F  F  N  V  V  G  E  L  V  Y  N  L  D  S  K  T  Q  L  K  S  1248

4861 GTGTTAACAATAGCCGAGAATCATTTTAATTCTCGTGAATTTGAACAATGCCTAAGTGTG 4920
1249  V  L  T  I  A  E  N  H  F  N  S  R  E  F  E  Q  C  L  S  V  1268

4921 GTTGAAAATGCACAGAGGAAATTTGGTTTTGACAGGTTGATATTTTCCATTCAAATAGTC 4980
1269  V  E  N  A  Q  R  K  F  G  F  D  R  L  I  F  S  I  Q  I  V  1288

4981 CGTTGCAAAATTGAATTAGGTGATTATGACGAAGCACATCGAATTGCAATTGAATGTCTT 5040
1289  R  C  K  I  E  L  G  D  Y  D  E  A  H  R  I  A  I  E  C  L  1308

5041 AAGGAATTAGGTGTTCCATTAGATGACGATGACGAATATACAAGTGAAAACCTGCTTGAG 5100
1309  K  E  L  G  V  P  L  D  D  D  D  E  Y  T  S  E  N  L  L  E  1328

5101 ACGTGTTTGGGAAAAATTCCGCTCTCTGTTGCTGACATTAGAGGTATTTTGAAGATTAAA 5160
1329  T  C  L  G  K  I  P  L  S  V  A  D  I  R  G  I  L  K  I  K  1348

5161 AGATGCAAGAATTCAAGAACATTGCTAATGTATCAGTTAATTTCAGAGCTAATTGTACTA 5220
1349  R  C  K  N  S  R  T  L  L  M  Y  Q  L  I  S  E  L  I  V  L  1368

5221 TTCAAGCTTCAAGGTAAAGACAAAGTGAGAAGGTTTCTCACAGCTTATGCGATGAGTCAA 5280
1369  F  K  L  Q  G  K  D  K  V  R  R  F  L  T  A  Y  A  M  S  Q  1388

5281 ATTCATACTCAAGGGTCTTCTCCTTATTGTGCAGTAATTCTTATAGACTTTGCACAATCA 5340
1389  I  H  T  Q  G  S  S  P  Y  C  A  V  I  L  I  D  F  A  Q  S  1408

5341 TTTGTCAACGAAACCACAACTTCAGGAATGCTTAAAGCAAAAGAACTCAGTATTGTCATG 5400
1409  F  V  N  E  T  T  T  S  G  M  L  K  A  K  E  L  S  I  V  M  1428

5401 TTGTCATTGATTAATAGAGCACCAGAAATATCTTTATCATATGTTCAGTCTATTTATGAA 5460
1429  L  S  L  I  N  R  A  P  E  I  S  L  S  Y  V  Q  S  I  Y  E  1448

5461 TATTATTTCAGTTGTCATGCTGTATTTTTTGAATCAATTGAAAAAATGCTGGATCTTATA 5520
1449  Y  Y  F  S  C  H  A  V  F  F  E  S  I  E  K  M  L  D  L  I  1468

5521 CATCCAGGTAACGCTAGTTCCCATTGCACAAGACTGTCTTATTATTCATCTTTTCATTTG 5580
1469  H  P  G  N  A  S  S  H  C  T  R  L  S  Y  Y  S  S  F  H  L  1488

5581 ATAGTTAATGTTTCCAAGATTTTCTTTTCATGTATGAATGGAGAAAGTTTCAAAATGTTC 5640
1489  I  V  N  V  S  K  I  F  F  S  C  M  N  G  E  S  F  K  M  F  1508

5641 TCAACATTCAAGTGTAAATCCTATTTAACAGGGGATCCCCAAATGCCTGAAATGGACAAT 5700
1509  S  T  F  K  C  K  S  Y  L  T  G  D  P  Q  M  P  E  M  D  N  1528
```

FIG. 5F

```
5701  TTTTTATACGATAGTGAAATGTTACTTGCTGGACATTCAGAATTGAATGAATTTATGAGA  5760
1529   F   L   Y   D   S   E   M   L   L   A   G   H   S   E   L   N   E   F   M   R   1548

5761  AAATATCAGTCATTCAACCAAACTTCCGTTGGTAAATTTTGCTACTATTTAATTGTACTA  5820
1549   K   Y   Q   S   F   N   Q   T   S   V   G   K   F   C   Y   Y   L   I   V   L   1568

5821  CTTGTAATGTCACGTGAACACAGATTTGACGAGGCTGCCGATTTGGTTTTGAAAGTTTTG  5880
1569   L   V   M   S   R   E   H   R   F   D   E   A   A   D   L   V   L   K   V   L   1588

5881  GAAGACTTACTGGAAAAATTGCCTGTATCTTTTTTGCATCATCAATATTACTTAATATGT  5940
1589   E   D   L   L   E   K   L   P   V   S   F   L   H   H   Q   Y   Y   L   I   C   1608

5941  GGTAAAGTGTTTGCTTATCACCAGACCAAAACCCCAGAAAGTGAGGAACAAGTGGAACGT  6000
1609   G   K   V   F   A   Y   H   Q   T   K   T   P   E   S   E   E   Q   V   E   R   1628

6001  ATTTTGGCTCGTCAATTTGAAAGATATGAATTGTGGGCACTGACGAATAAGCCGACCCTT  6060
1629   I   L   A   R   Q   F   E   R   Y   E   L   W   A   L   T   N   K   P   T   L   1648

6061  CTACCACGGTACTTGTTGTTGAGTACCTACAAACAGATTAGAGAAAACCATGTTGACAAG  6120
1649   L   P   R   Y   L   L   S   T   Y   K   Q   I   R   E   N   H   V   D   K   1668

6121  TTAGAAATACTAGATTCATTTGAGGAGGCGTTACAGACGGCCCATAAATTTCATAATGTA  6180
1669   L   E   I   L   D   S   F   E   E   A   L   Q   T   A   H   K   F   H   N   V   1688

6181  TATGATATGTGCTGGATCAATTTGGAATGTGCAAGATGGTTAATTAGCATAAACCAAAAA  6240
1689   Y   D   M   C   W   I   N   L   E   C   A   R   W   L   I   S   I   N   Q   K   1708

6241  AGGCACAGAATCTCAAGAATGGTTAAACAAGGTCTTAAAATTTTGAGAAGCTTGGAATTA  6300
1709   R   H   R   I   S   R   M   V   K   Q   G   L   K   I   L   R   S   L   E   L   1728

6301  AATAATCATTTAAGATTAGCTGAATTTGAATTTGATGAATACATTGAGGACGAAGATCAC  6360
1729   N   N   H   L   R   L   A   E   F   E   F   D   E   Y   I   E   D   E   D   H   1748

6361  AGAAATAAATGGGCAGGGTTAACTAATAATCCAACATTGGATACTGTTACTACCTGGCAA  6420
1749   R   N   K   W   A   G   L   T   N   N   P   T   L   D   T   V   T   T   W   Q   1768

6421  CAACAGAACATGCCCGATAAGGTATCTCCATGCAATGACAAGCAGTTGGTCCACGGAAAA  6480
1769   Q   Q   N   M   P   D   K   V   S   P   C   N   D   K   Q   L   V   H   G   K   1788

6481  CAATTTGGCAAAAAAGAGTTTGATAGCCATTTGCTCAGATTGCACTTTGATGGCCAATAT  6540
1789   Q   F   G   K   K   E   F   D   S   H   L   L   R   L   H   F   D   G   Q   Y   1808

6541  ACAGGCCTAGATTTGAATTCAGCTATTCGTGAATGTCTAGCAATATCCGAAGCTTTAGAC  6600
1809   T   G   L   D   L   N   S   A   I   R   E   C   L   A   I   S   E   A   L   D   1828
```

FIG. 5G

```
6601 GAAAATTCCATTCTCACAAAGTTGATGGCATCTGCCATCAAGTATTCAGGTGCCACATAT 6660
1829  E  N  S  I  L  T  K  L  M  A  S  A  I  K  Y  S  G  A  T  Y  1848

6661 GGGGTAATTGTCACGAAGAAAAACCAGGAGACACCTTTTCTTAGAACAATTGGCTCGCAG 6720
1849  G  V  I  V  T  K  K  N  Q  E  T  P  F  L  R  T  I  G  S  Q  1868

6721 CACAATATTCACACATTAAACAACATGCCAATTTCCGACGACATTTGTCCTGCTCAGTTG 6780
1869  H  N  I  H  T  L  N  N  M  P  I  S  D  D  I  C  P  A  Q  L  1888

6781 ATTCGTCATGTATTGCATACAGGAGAAACGGTGAACAAAGCTCATGATCACATAGGATTT 6840
1889  I  R  H  V  L  H  T  G  E  T  V  N  K  A  H  D  H  I  G  F  1908

6841 GCTAACAAGTTTGAGAATGAATACTTTCAAACAACAGATAAAAAGTATTCAGTTGTGTGT 6900
1909  A  N  K  F  E  N  E  Y  F  Q  T  T  D  K  K  Y  S  V  V  C  1928

6901 TTGCCATTAAAGAGTCTGCTTGGATTATTTGGTGCACTTTATCTAGAAGGTAGTGATGGT 6960
1929  L  P  L  K  S  L  L  G  L  F  G  A  L  Y  L  E  G  S  D  G  1948

6961 GATTTTGGACATGAAGATTTGTTCAATGAAAGGAAATGTGATTTGTTACAACTTTTTTGC 7020
1949  D  F  G  H  E  D  L  F  N  E  R  K  C  D  L  L  Q  L  F  C  1968

7021 ACACAAGCAGCTGTGGCTTTGGGTAAGGAGCGTTTGCTTTTGCAAATGGAACTAGCAAAA 7080
1969  T  Q  A  A  V  A  L  G  K  E  R  L  L  L  Q  M  E  L  A  K  1988

7081 ATGGCAGCAGAAGACGCCACTGATGAAAAAGCCAGTTTTTTGGCAAACATGTCACATGAA 7140
1989  M  A  A  E  D  A  T  D  E  K  A  S  F  L  A  N  M  S  H  E  2008

7141 ATACGAACCCCATTCAATTCGTTATTGTCATTTGCTATTTTTTTGTTAGATACCAAATTG 7200
2009  I  R  T  P  F  N  S  L  L  S  F  A  I  F  L  L  D  T  K  L  2028

7201 GATTCTACTCAAAGAGAATATGTCGAGGCAATTCAGAGCTCCGCAATGATAACGTTGAAT 7260
2029  D  S  T  Q  R  E  Y  V  E  A  I  Q  S  S  A  M  I  T  L  N  2048

7261 ATTATTGATGGGATACTTGCGTTTTCCAAAATTGAGCATGGATCCTTTACATTAGAAAAT 7320
2049  I  I  D  G  I  L  A  F  S  K  I  E  H  G  S  F  T  L  E  N  2068

7321 GCCCCCTTTTCTTTGAATGATTGTATCGAGACTGCTATTCAAGTAAGTGGGGAAACAATT 7380
2069  A  P  F  S  L  N  D  C  I  E  T  A  I  Q  V  S  G  E  T  I  2088

7381 TTGAATGACCAGATTGAGTTGGTGTTTTGTAACAATTGTCCAGAGATTGAATTTGTGGTT 7440
2089  L  N  D  Q  I  E  L  V  F  C  N  N  C  P  E  I  E  F  V  V  2108

7441 GGTGATCTAACGAGGTTCAGACAAATTGTGATCAATTTGGTGGGTAATGCTATTAAGTTT 7500
2109  G  D  L  T  R  F  R  Q  I  V  I  N  L  V  G  N  A  I  K  F  2128
```

FIG. 5H

```
7501 ACAACCAAAGGTCATGTTTTGATTTCTTGTGATAGCCGAAAAATTACGGACGACAGATTT 7560
2129  T  T  K  G  H  V  L  I  S  C  D  S  R  K  I  T  D  D  R  F  2148

7561 GAGATCAATGTGTCAGTTGAGGATTCAGGAATTGGAATTTCCAAAAAATCTCAAAATAAA 7620
2149  E  I  N  V  S  V  E  D  S  G  I  G  I  S  K  K  S  Q  N  K  2168

7621 GTGTTTGGAGCATTTTCTCAAGTAGATGGTTCCGCAAGACGAGAATATGGTGGCTCTGGA 7680
2169  V  F  G  A  F  S  Q  V  D  G  S  A  R  R  E  Y  G  G  S  G  2188

7681 TTAGGTTTAGCTATATCAAAGAAATTGACTGAACTAATGGGTGGCACAATTAGATTTGAA 7740
2189  L  G  L  A  I  S  K  K  L  T  E  L  M  G  G  T  I  R  F  E  2208

7741 AGTGAGGAAGGGATTGGCACAACGTTTTATGTTAGCGTCATTATGGACGCAAAAGAATAC 7800
2209  S  E  E  G  I  G  T  T  F  Y  V  S  V  I  M  D  A  K  E  Y  2228

7801 TCATCCCCGCCATTTAGTTTAAATAAAAAATGTTTGATTTACAGCCAGCATTGTCTTACT 7860
2229  S  S  P  P  F  S  L  N  K  K  C  L  I  Y  S  Q  H  C  L  T  2248

7861 GCCAAGTCAATTTCAAATATGCTTAATTATTTTGGATCAACAGTTAAAGTCACTAATCAG 7920
2249  A  K  S  I  S  N  M  L  N  Y  F  G  S  T  V  K  V  T  N  Q  2268

7921 AAGTCTGAGTTTTCAACTTCCGTGCAAGCCAACGACATCATTTTTGTTGATCGCGGAATG 7980
2269  K  S  E  F  S  T  S  V  Q  A  N  D  I  I  F  V  D  R  G  M  2288

7981 GAACCTGATGTTAGTTGCAAAACCAAAATCATTCCCATCGACCCAAAACCTTTCAAAAGA 8040
2289  E  P  D  V  S  C  K  T  K  I  I  P  I  D  P  K  P  F  K  R  2308

8041 AACAAACTCATTAGTATTCTCAAAGAACAACCAAGTTTGCCCACCAAAGTGTTTGGAAAC 8100
2309  N  K  L  I  S  I  L  K  E  Q  P  S  L  P  T  K  V  F  G  N  2328

8101 AACAAATCTAATTTATCAAAACAATACCCTCTAAGAATATTATTAGCAGAAGACAATCTT 8160
2329  N  K  S  N  L  S  K  Q  Y  P  L  R  I  L  L  A  E  D  N  L  2348

8161 TTGAACTATAAAGTATGTTTGAAGCATTTGGATAAATTGGGGTACAAGGCAGATCATGCC 8220
2349  L  N  Y  K  V  C  L  K  H  L  D  K  L  G  Y  K  A  D  H  A  2368

8221 AAAGATGGAGTAGTAGTTTTGGATAAATGTAAAGAACTACTAGAAAAAGACGAAAAATAT 8280
2369  K  D  G  V  V  V  L  D  K  C  K  E  L  L  E  K  D  E  K  Y  2388

8281 GATGTCATATTGATGGATATTCAAATGCCTCGTAAGGACGGTATTACAGCTACAAGGGAT 8340
2389  D  V  I  L  M  D  I  Q  M  P  R  K  D  G  I  T  A  T  R  D  2408

8341 TTGAAAACATTGTTTCACACACAAAAAAAGGAAAGTTGGTTACCCGTGATCGTAGCATTG 8400
2409  L  K  T  L  F  H  T  Q  K  K  E  S  W  L  P  V  I  V  A  L  2428
```

FIG. 5I

```
8401  ACAGCTAATGTTGCTGGAGACGACAAAAAGAGGTGTCTAGAAGAGGGAATGTTTGATTTT  8460
2429   T  A  N  V  A  G  D  D  K  K  R  C  L  E  E  G  M  F  D  F   2448

8461  ATAACCAAACCCATTTTACCAGATGAACTTAGACGTATTTTAACAAAAGTAGGGGAAACA  8520
2449   I  T  K  P  I  L  P  D  E  L  R  R  I  L  T  K  V  G  E  T   2468

8521  GTGAATATGTAAAATGTGTATTTAATAATAAGATCT  8556
2469   V  N  M  *                          2471
```

FIG. 5J

HISTIDINE KINASE TWO-COMPONENT IN *CANDIDA ALBICANS*

This application claims benefit of 35 U.S.C. section 119(e) based on copending U.S. Provisional application Ser. No.: 60/052,273, filed Jul. 10, 1997 and Provisional application Ser. No: 60/074,308, filed Feb. 11, 1998, which are hereby incorporated by reference in their entireties.

FIELD OF THE INVENTION

The present invention relates to a novel *Candida albicans* gene encoding a polypeptide which is a member of the histidine kinase family. More specifically, isolated nucleic acid molecules are provided encoding a *Candida albicans* polypeptide named Histidine Kinase-1 (CaHK-1). CaHK-1 polypeptides are also provided, as are vectors, host cells and recombinant methods for producing the same. The invention further relates to methods for testing compounds for ability to inhibit CaHK-1, an enzyme which is active in phosphorylating host cell proteins to render the host cell susceptible to invasion by Candida albicans

BACKGROUND OF THE INVENTION

All cells must sense changes in their environment and respond appropriately. In this regard, the two-component signal transduction regulatory system was initially described in prokaryotic organisms where it is thought to play a function in chemotaxis, osmoregulation, sporulation, host-pathogen interactions and response to carbon, nitrogen and phosphate availability. In these microorganisms, the prototypical two-component regulator system is comprised of two proteins, a histidine protein kinase (also called a sensor protein and usually cell membrane-bound) and a response regulator (or effector protein), which is associated with an internal response. The sensor kinase, when activated by a signal, autophosphorylates a histidine residue using ATP as a phosphodonor; the histidine is a part of a conserved block of residues, typically referred to as the H-box. Subsequently, the phosphorylated sensor kinase serves as a phosphodonor to a conserved aspartate residue in the response regulator. This phosphorylation modulates the activity of the effector protein to elicit an adaptive response to the stimulus (reviewed in Hoch and Silhavy, *Two-component signal transduction,* ASM Press. Washington, D.C. USA (1995)).

Although the general sequence of events and the number of proteins involved is similar for all of these organisms, each pathway exhibits some variation on the basic scheme (Appleby et al., *Signal transduction via the multi-step phosphorelay; not necessarily a road less traveled,* Cell 86, 845–848 (1996)). For instance, in *Bordetella pertussis,* the BvgS-BvgA two-component modulates the transcriptional control of several virulence factors. Although there are two proteins, four phosphorylation events occur in sequence, creating a four-step His-Asp-His-Asp phosphorelay (Uhl and Miller; *Integration of multiple domains in a two-component sensor protein: the Bordetella pertussis BvgAS phosphorelay,* EMBO J. 15, 1028–1036 (1996)). A similar mechanism has been the plant pathogenic bacterium, *Pseudomonas syringae.*

Homologous pathways have recently been identified in several eukaryotic organisms, including, *Saccharomyces cerevisiae, Dictyostelium discoideum, Neurospora crassa* and *Arabidopsis thaliana.* In *S. cerevisiae* the phosphorelay through a two-component signal pathway is composed of three proteins. An Sln1p transmembrane protein serves as a sensor protein, which after autophosphorylation of a histidine residue and transfer to an aspartate in the same protein, phosphorylates a histidine residue of a second protein (Ypd1p). Ypd1p is a small cytoplasmic protein, which functions much like a sensor protein and, in turn, it phosphorylates a third protein effector in the relay system (Ssk1p). The activation of a downstream MAP kinase cascade is dependent upon the phosphorylation of Ssk1p. In cells which are grown under low osmotic conditions, phosphorylated Ssk1p does not activate the Map kinase pathway. However, under conditions of hyperosmolarity, phosphotransfer among the two-component does not occur. Consequently, the MAP kinase pathway and the transcription of genes involved in glycerol metabolism occur. This pathway, referred to as the HOG pathway (High Osmolarity Glycerol Response), thus provides a phosphorylated effector molecule which is inactive in environmentally stressed conditions. In *D. discoideum* two different histidine kinases (DhkA and DokA) have been described. DhkA modulates the transcriptional regulation of prestalk gene expression and the control of the terminal differentiation pathway. DokA is involved, like Sln1p in S. cerevisiae, in the osmoregulatory pathway. In *N. crassa,* a two-component histidine kinase (Nik-1) has been reported to be involved in hyphal development and osmosensitivity. Finally, in *A. thaliana* the product of the ETR1 gene may be involved in an early step in ethylene signal transduction through phosphorylation, as in the prokaryotic two-component systems. Thus, there is a need for the discovery of proteins responsible for causing diseases resulting from infection with pathogenic fungi because such proteins may be used in the development of treatments for such diseases.

SUMMARY OF THE INVENTION

The present invention provides isolated nucleic acid molecules comprising a polynucleotide encoding a portion of the CaHK-1 polypeptide having the amino acid sequence shown in FIGS. 2A–D (SEQ ID NO:2) or the amino acid sequence encoded by the cDNA clone deposited as plasmid DNA as ATCC Deposit Number 209504 on 26 Nov. 1997. The nucleotide sequence was determined by sequencing the deposited cloned DNA, which is shown in FIGS. 2A–D (SEQ ID NO: 1), and contains an open reading frame encoding a complete polypeptide of 971 amino acid residues, including an initiation codon encoding an N-terminal methionine at nucleotide positions 181 to 183. Nucleic acid molecules of the invention include those encoding the complete amino acid sequence excepting the N-terminal methionine shown in FIGS. 2A–D (SEQ ID NO: 1), or the complete amino acid sequence excepting the N-terminal methionine encoded by the cloned DNA in ATCC Deposit Number 209504, which molecules also can encode additional amino acids fused to the N-terminus of the CaHK-1 amino acid sequence.

The invention further provides isolated nucleic acid molecules comprising a polynucleotide encoding a full length CaHK-1 polypeptide having the complete amino acid sequence shown in FIGS. 5A–J (SEQ ID NO:4) or the complete amino acid sequence encoded by the cDNA clones deposited as plasmid DNA as ATCC Deposit Numbers 209504 and 209505 deposited 26 Nov. 1997. The nucleotide sequence was determined by sequencing the deposited cloned DNA, which is shown in FIGS. 5A–J (SEQ ID NO:3), and contains an open reading frame encoding a complete polypeptide of 2471 amino acid residues, including an initiation codon encoding an N-terminal methionine at nucleotide positions 1117 to 1119. Nucleic acid molecules of the invention include those encoding a complete amino acid sequence excepting the N-terminal methionine shown in FIGS. 5A–J (SEQ ID NO:3), or the partial amino acid sequence excepting the N-terminal methionine encoded by the cloned DNA in ATCC Deposit Numbers 209504 and 209505, which molecules also can encode additional amino acids fused to the N-terminus of the CaHK-1 amino acid sequence.

The CaHK-1 proteins of the present invention share sequence homology with the translation products of the mRNA for two component histidine kinases from several prokaryotes and eukaryotes (FIG. 3), including the following conserved domains: (a) the predicted sensor domain (residues 482 to 721 in FIGS. 2A–D (SEQ ID NO:2) or residues 1982 to 2221 in FIGS. 5A–J) (SEQ ID NO:4); and (b) the predicted response regulator domain domain (residues 834 to 971 in FIGS. 2A–D (SEQ ID NO:2) or residues 2334 to 2471 in FIGS. 5A–J) (SEQ ID NO:4). Two component histidine kinases are thought to be important in virulence. The homology between CaHK-1 and other histidine kinases (FIG. 3) indicates that CaHK-1 may also be involved in virulence of Candida albicans.

Thus, one aspect of the invention provides an isolated nucleic acid molecule comprising a polynucleotide having a nucleotide sequence selected from the group consisting of: (a) a nucleotide sequence encoding a full-length CaHK- I polypeptide having the complete amino acid sequences in FIGS. 2A–D (SEQ ID NO: 1) or FIGS. 5A–J, (SEQ ID NO:3) or the complete amino acid sequence encoded by the cloned DNA contained in the ATCC Deposit Numbers. 209504 and 209505; (b) a nucleotide sequence encoding a full-length CaHK- I polypeptide having the complete amino acid sequence in FIGS. 2A–D (SEQ ID NO: 1) or FIGS. 5A–J (SEQ ID NO:3) excepting the N-terminal methionine (i.e., amino acid positions 2 to 971 in FIGS. 2A–D (SEQ ID NO: 1) and amino acid positions 2 to 2471 in FIGS. 5A–J) (SEQ ID NO:3) or the complete amino acid sequence excepting the N-terminal methionine encoded by the cloned DNA contained in the ATCC Deposit Numbers. 209504 and 209505; (c) a nucleotide sequence encoding the predicted sensor domain of the CaHK-1 polypeptide having the amino acid sequence at positions 482 to 721 in FIGS. 2A–D (SEQ ID NO:1) or 1982 to 2221 in FIGS. 5A–J (SEQ ID NO:3), or as encoded by the cloned DNA contained in the ATCC Deposit Numbers 209504 and 209505; (d) a nucleotide sequence encoding a polypeptide comprising the predicted response regulator domain of the CaHK-1 polypeptide having the amino acid sequence at positions 834 to 971 in FIGS. 2A–D (SEQ ID NO: 1) or residues 2334 to 2471 in FIGS. 5A–J (SEQ ID NO:3), or as encoded by the cloned DNA contained in the ATCC Deposit Numbers 209504 and 209505; (e) the predicted sensor and response regulator domains of the CaHK-1 polypeptide having the amino acid sequence at positions 482 to 971 in FIGS. 2A–D (SEQ ID NO:3) or residues 1982 to 2471 in FIGS. 5A–J (SEQ ID NO:4), or as encoded by the cloned DNA contained in the ATCC Deposit Numbers 209504 and 209505; and (f) a nucleotide sequence complementary to any of the nucleotide sequences in (a), (b), (c), (d) or (e) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e) or (f), above, or a polynucleotide which hybridizes under stringent hybridization conditions to a polynucleotide in (a), (b), (c), (d), (e) or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CaHK-1 polypeptide having an amino acid sequence in (a), (b), (c), (d) or (e), above.

The present invention also relates to recombinant vectors, which include the isolated nucleic acid molecules of the present invention, and to host cells containing the recombinant vectors, as well as to methods of making such vectors and host cells and for using them for production of CaHK-1 polypeptides or peptides by recombinant techniques.

The invention further provides an isolated CaHK-1 polypeptide comprising an amino acid sequence selected from the group consisting of: (a) the amino acid sequence of the full-length CaHK-1 polypeptide having the complete amino acid sequence shown in FIGS. 2A–D (SEQ ID NO:2) or FIGS. 5A–J (SEQ ID NO:4), or the complete amino acid sequence encoded by the DNAs clone contained in the ATCC Deposit Numbers 209504 and 209505; (b) the amino acid sequence of a full-length CaHK-1 polypeptide having the complete amino acid sequence shown in FIGS. 2A–D (SEQ ID NO:2) or FIGS. 5A–J (SEQ ID NO:4), excepting the N-terminal methionine (i.e., amino acid positions 2 to 971 of FIGS. 2A–D (SEQ ID NO:2) and positions 2 to 2471 of FIGS. 5A–J (SEQ ID NO:4)) or the complete amino acid sequence excepting the N-terminal methionine encoded by the DNA clone contained in the ATCC Deposit Numbers 209504 and 209505; (c) the amino acid sequence of the sensor domain of the CaHK- I polypeptide having the amino acid sequence at positions 482 to 721 in FIGS. 2A–D (SEQ ID NO:2) or 1982 to 2221 in FIGS. 5A–J (SEQ ID NO:4), or as encoded by the DNA clones contained in the ATCC Deposit Numbers 209504 and 209505; (d) the amino acid sequence of the response regulator domain of the CaHK-1 polypeptide having the amino acid sequence at positions 834 to 971 in FIGS. 2A–D (SEQ ID NO:2) or residues 2334 to 2471 in FIGS. 5A–J (SEQ ID NO:3), or as encoded by the DNA clones contained in the ATCC Deposit Numbers 209504 and 209505; and (e) the amino acid sequence of the sensor and response regulator domains of the CaHK-1 polypeptide having the amino acid sequence at positions 482 to 971 in FIGS. 2A–D (SEQ ID NO:2) or positions 1982 to 2471 in FIGS. 5A–J (SEQ ID NO:3), or as encoded by the DNA clones contained in the ATCC Deposit Numbers 209504 and 209505.

A further nucleic acid embodiment of the invention relates to an isolated nucleic acid molecule comprising a polynucleotide which encodes the amino acid sequence of a CaHK-1 polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a polynucleotide which encodes the amino acid sequence of a CaHK-1 polypeptide to have an amino acid sequence which contains not more than 10, 9, 8, 7, 6, 5, 4, 3, 2 or 1 conservative amino acid substitutions.

An additional embodiment of this aspect of the invention relates to a peptide or polypeptide which comprises the amino acid sequence of an epitope-bearing portion of a CaHK-1 polypeptide having an amino acid sequence described in (a), (b), (c), (d) or (e), above. Peptides or polypeptides having the amino acid sequence of an epitope-bearing portion of a CaHK-1 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a CaHK-1 polypeptide having an amino acid sequence described in (a), (b), (c), (d) or (e) above. The term antibody includes polyclonal and monoclonal antibodies and fragments thereof including F(ab), F(ab)$_2$, single-chain antibodies (sFv), disulfide-linked variable regions (dsFv), The term antibody further includes humanized and chimeric antibodies. The invention further provides methods for isolating antibodies that bind specifically to a CaHK-1 polypeptides having an amino acid sequence as described herein including but not limited to hybridoma technology and phage display methods. Such antibodies are useful diagnostically or therapeutically as described below.

DESCRIPTION OF THE FIGURES AND TABLES

FIG. 1 shows the nucleotide sequence of a CaHK-1 polynucleotide (FIG. 1 A, SEQ ID NO: 1) and the deduced amino acid sequence (FIG. 1B, SEQ ID NO:2) of a CaHK-1 polypeptide. In case of conflict between FIGS. 1A–B and FIGS. 2A–D, FIG. 1 is controlling.

FIGS. 2A–D shows the nucleotide sequence of a partial C. albicans CaHK-1 gene clone and flanking regions. The predicted amino acid sequence of the ORF is shown in a one-letter code. Six putative N-glyosylation sites (Ans-X-Ser/Thr) are underlined, and the predicted autophosphorylated His and the Asp which serves as the residue for the second phosphorylation are bolded.

FIG. 3 shows a comparison of the sensor kinase domain of CaHK-1, using the residue designation from FIG. 2, with other histidine kinases from prokaryotic (Shk, BarA and LemA) and eukaryotic (DokA, Nik-1 and Sln1p) cells. The putative autophosphorylated His is indicated by an asterisk.

FIGS. 4A–D shows the nucleotide sequence of a CaHK-1 polynucleotide (FIGS. 4A–C, SEQ ID NO:3) and the deduced amino sequence (FIG. 4D, SEQ ID NO:4) of a CaHK-1 polypeptide.

FIGS. 5A–J shows the nucleotide sequence of the full length C. albicans CaHK-1 gene and flanking regions. The putative TATA-like sequence, AT-rich, and CT-box are underlined. The predicted amino acid sequence of the ORF is shown in a one-letter code.

Table 1 lists the amino acid residues comprising antigenic epitopes present in the full length CaHK-1 polypeptide described in FIG. 4, as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power MacIntosh, DNASTAR, Inc., 1228 South Park Street Madison, Wis.). It will be appreciated that depending on the analytical criteria used to predict antigenic determinants, the exact address of the determinant may vary slightly. The exact location of the antigenic determinant may shift by about 1 to 5 residues, more likely 1 to 2 residues, depending on the criteria used. It will also be appreciated that, generally speaking, amino acids can be added to either terminus of a peptide or polypeptide containing an antigenic epitope without affecting its activity, whereas removing residues from a peptide or polypeptide containing only the antigenic determinant is much more likely to destroy activity. It will be appreciated that the residues and locations shown described in Table 1 correspond to the polypeptide sequence of FIG. 4 (SEQ ID NO:4).

DESCRIPTION OF THE INVENTION

A histidine kinase, two-component gene (CaHK-1) from Candida albicans has been cloned and characterized. The full length gene encodes a 2471 amino acid protein with an estimated molecular mass of 281.8kDa (FIGS. 5A–J). A partial length clone has also been isolated that encodes a 110.66kDa fragment (FIGS. 2A–D). A homology search of CaHK-1 polypeptides with other proteins in the databases showed that CaHK-1 exhibits the greatest homology, with both the sensor and regulator components of prokaryotic and eukaryotic two-component histidine kinases. A further analysis of this homology showed that CaHK-1 possessed both sensor and regulator domains in the same polypeptide. Also, CaHK-1 is probably found as a soluble protein. The sensor kinase domain of CaHK-1 contains a conserved motif that is characteristic of all histidine kinase proteins, including the putative histidine which is believed to be autophosphorylated during activation, ATP binding motifs and others (F and N-motifs), with unknown function. The CaHK-1 sensor domain also contains conserved aspartate and lysine residues and the putative aspartate which is secondarily phosporylated by the autophosphorylated histidine. In addition, Southern blot analysis of the C. albicans genomic DNA suggests that only there is one copy of the CaHK-1 gene in the C. albicans genome.

Until now, the isolation of two-component genes from human pathogenic fungi has not been reported. However, recently, a partial cDNA has been isolated by random sequencing of a cDNA Candida albicans library. The partial cDNA has a significant homology with a cyanobacterium histidine kinase (Synechocystis app.) (Kanero et al., 1996), Pseudomonas aeruginosa histidine kinase LemA, a sensor Escherichia coli histidine kinase (BarA), Erwinia carotovora subsp. carotovora sensor/regulator protein RpfA, as well as with histidine kinases of N. crassa, D. discoideum and S. cerevisiae. CaHK-1 is believed to function similarly to the two-component histidine kinases in the regulation of virulence in pathogenic bacteria and in the molecular events that regulate the osmolarity and differentiation in fungi.

Restriction map of the CaHK-1 gene

In order to isolate the CaHK-1 gene to a specific restriction fragment of the genomic DNA of C. albicans, a Southern blot experiment at high stringency was performed after digestion of the genomic DNA with several restriction enzymes as described (see section 2.4). A 5.0 kb BglII—BglII fragment was identified from genomic DNA which hybridized to the 1.0 kb NotI-SalI probe. These results indicate that the C. albicans genome contains only one copy of the CaHK-1 gene. However, this does not preclude the possibility of additional histidine kinase genes in C. albicans. Using reduced stringency conditions, multiple histidine kinases have been detected in Arabidopsis. In Dictyostelium and Neurospora, two histidine kinases have been characterized by PCR using degenerate oligonucleotides as primers that were designed based on the conserved sequences of bacterial histidine kinases.

On the other hand, by a northern experiment, it was shown that the full length CaHK-1 gene is transcribed in a 7.6 kb mRNA which matches the size of the full length ORF, so the whole ORF of CaHK-1 should be contained within the 5.0 kb fragment.

Isolation of a Histidine kinase gene of C. albicans (CaHK-1)

Fourteen clones (designed G1–G14) were isolated from a genomic λEMBL3 library of C. albicans. Restrictions analysis of the DNA samples obtained from each clone by BglII digestion and Southern blot, revealed that only five of them contained the entire 5.0 kb BglII—BglII fragment described above. This fragment from the clone G3 was purified, subcloned into pBS SK+(Stratagene) and sequenced on both strands. In FIGS. 2A–D is shown the relevant 3.13 kb DNA sequence that contains a 2913 bp ORF of CaHK-1 encoding a protein with 971 amino acids with a predicted molecular mass and pI of 110.6 kDa and 6.54, respectively. A new probe corresponding to a 1.1 kb BglII-EcoR1 fragment, located at the 5' end of the 5.0 kb BglII—BglII, was prepared. By using this probe, a 2.6 kb EcoR1—EcoR1 fragment that overlapped the 5.0 kb BglII—BglII fragment by 1.1 kb was identified, subcloned and sequenced. Finally, a new round of chromosome walking was completed by using as a probe the new 1.5 kb non-overlapping sequence of the 2.6 kb fragment. A 3.5 kb BglII—BglII fragment, which overlaps the 2.6 kb EcoR1—EcoR1 fragment, was identified, subcloned, and sequenced. A putative start site for the CaHK-1 gene within this fragment was identified. The full length CaHK-1 gene is shown in FIGS. 5A–J. The 2913 ORF discussed above is an inframe ORF within the full length CaHK-1 7413 bp ORF of FIGS. 5A–J.

In order to determine how far the mRNA extends upstream from the start site, we amplified the 5' end of the mRNA by RT-PCR using two different pairs of primers. In all cases, one primer was the same (p1) and was primary used in the RT step. In the PCR reaction, the p1 primer, which hybridizes between positions 845 to 864 downstream from the start site (FIGS. 5A–J), was used in combination with the other primers, which were designed according to their locations within the 5' non-coding sequence.

One of these primers (p2) hybridized just downstream from the putative TATA-like sequence, and the other (p3) hybridized just upstream from the AT-rich region (FIGS. 5A–J). The results showed that RT-PCR using the p1/p2 pair produced a fragment of 0.98 kb, but when the p1/p3 pair was used, no product was obtained, indicating that the mRNA does not extend beyond the point where the p2 primer hybridizes. Moreover, the TATA-like sequence located just upstream from where p2 hybridizes should be most probable functional TATA-like sequence.

In addition to the putative TATA-like sequence (from position –62 to –67 of the start site shown in FIGS. 5A–J) in the 5'non-coding region of CaHK-1, a CT-bot and an AT-rich region, localized between positions –99 to –117 and –126 to –162 upstream from the start codon (FIGS. 5A–J), respectively, are also found. The consensus sequence surrounding the start codon of the CaHK-1 gene (5'-AAATCATGTCT-3') (SEQ ID NO:8), also matches the consensus sequence surrounding S. cerevisiae start codons (5'-AAAYAATGTCT-3') (SEQ ID NO:9), (Hinnebush and Liebman (1991) In Broach, J. R. et al. (Eds.) The Molecular and Cellular Biology of the Yeast Saccharomyces. Cold Spring Harbor Laboratory Press, Cold Spring Harbor, N.Y., pp. 627–735). In the 3' non-coding region, there is a putative polyadenylation signal (AATAAA-like) between positions 12 to 19 downstream from the stop codon (FIGS. 5A–J). Within the encoding region, no introns were identified, similar to most of the C albicans genes characterized thus far.

The 7413bp ORF of CaHK-1 encodes a protein of 2471 amino acids with a predicted molecular mass of 281.1 kDa and a pI of 6.51. Analysis of previously characterized bacterial and eukaryotic histidine kinases has revealed the existence of two extensive hydrophobic regions which are thought to correspond to transmembrane-spanning segments that define a sensory extracellular domain. However, the CaHK-1 gene product, when analyzed using Kyte-Doolittle and Goldman algorithms, does not show any extensive hydrophobic stretch of amino acids. Hence, it is expected that CaHK-1 is fairly protein soluble.

Comparison of the amino acid sequence of CaHK-1 with other related histidine kinases A computer search using the BLAST program (Altschul et al., 1990) revealed that the N-terminal end of the CaHK-1 protein does not share homology with any protein. This is in agreement with all other histidine kinases, whose sensor input domain differs broadly in structure, reflecting the variety of chemical and physical stimuli they detect.

However, the CaHK1 C-terminal end shares strong homology to kinases of the cyanobacterium Synechocystis sp. (GeneBank Accession numbers: D90903 and D90910), the E. coli sensor regulator BarA, the P. synringae LemA, Erwinia carotovora subsp. carotovora sensor/regulator protein RpfA, and with the B. pertussis BvgS virulence regulator factor. It also shows a strong homology with several eukaryotic histidine kinases among them, DokA and DhkA from D. discoideum; Nik-1 from N. crassa; Sln1p from S. cerevisiae; and ETR1 from A. thaliana. The deduced CaHK-1 sequence is most similar to the sequence of the Synechocystis histidine kinases ORF ID:slr1759 [D90903] (40.8% identity; 50.2% similarity), Pseudomonas aeruginosa histidine kinase LemA (4105% identity; 51.4% similarity), Synechocystis histidine kinase [D90910] ORF ID:sll1905 (42.3% identity; 51.5% similarity), Erwinia carotovora subsp. carotovora sensor/regulator protein RpfA (40.0% identity; 51.2% similarity), and E. coli BarA sensor-regulator protein. (39.9% identity; 53.1 % similarity), The carboxyl-terminal sequences of histidine kinases of both prokaryotes and eukaryotes have highly conserved sensor and response regulator domains. The average length of 240 aa for the sensor and 120 as for the response regulator appears to be fairly uniform. In bacteria, the histidine kinase domain of the sensor is characterized by five sequence motifs arranged in a specific order with loosely conserved spacing. This was also found in DhkA and DokA from Dictyostelium, Sln1p from Saccharomyces, Nik-1 from Neurospora and ETR1 from Arabidopsis. All of these enzymes are characterized by a motif flanking the histidine residue that is autophosphrylated (H-motif), a N-motif which is located about 100 aa downstream from the H-motif, two glycine-rich regions (G1 and G2 motifs) that form the ATP biding site, and the F-motif which is located between the G1 and G2 motifs. On the other hand, the sensor protein is usually membrane-bound, while most of the response regulators from bacteria are found as soluble proteins. However, in some histidine kinases from bacteria (for example, in BvgS from B. pertussis) and in the characterized eukaryotic histidine kinases, the sensor and the response regulator are different domains of a single polypeptides which are membrane-bound, except Nik-1 and DhkA which appear as soluble proteins. In all of these examples, in the response regulator domain, there are three conserved motifs that include a pair of aspartates near the N-termini, an aspartate motif which accepts a phosphate and a motif near the C-termini which contains a key lysine.

Comparison of CaHK-1 polypeptides to sequences in databases revealed extensive similarities to both the sensor and response regulator of bacterial, fungal and plant two-component systems. The CaHK-1 polypeptides, like most of the characterized eukaryotic histidine kinases, exhibits the sensor kinase and the receiver module of the response regulator in the same polypeptide. The histidine kinase domain (sensor domain) of the CaHK-1 polypeptides is located between residues 482 and 721 (FIGS. 2A–D) and 1982 to 2221 (FIGS. 5A–J). This domain contains all of the conserved residues and spacing between prokaryotic and eukaryotic histidine kinases, including the putative phosphoryl group acceptor ($His^{507}$) and the conserved Asn ($Asn^{620}$) separated by 112 aa. Other conserved motifs in this domain include the sequences of the G1 motif (residues 656–660 (FIGS. 2A–D) or 2156–2160 (FIGS. 5A–J), DSGIG) and G2 motif (residues 686–690 (FIG. 2) or 2186–2190 (FIG. 5), GSGLG), which fit the consensus GXGXG-[$X_{15-50}$]-GXGXG for glycine rich loops characteristics of adenosine triphosphate (ATP)-binding proteins. Between the G1 and G2 motifs is also found the F-motif (residues 670–673 (FIGS. 2A–D) or 2170–2173 (FIGS. 5A–J), FXXF) (Ota and Varsharvsky, 1993).

In the response regulator domain of CaHK-1 (2334–2471 in FIGS. 5A–J), FIG. 3, and by inference from sequence similarities, the $Asp^{2394}$ should be the predicted site of phosphorylation and the $His^{2007}$ of the CaHK-1 sensor kinase domain the putative donor of the phosphoryl group. The $Asp^{2346}$ should be one of the pair of aspartates that are conserved among prokaryotic response regulators but apparently not in eukaryotic, in which it appears as ED instead of DD. The $Lys^{2451}$ should be the other conserved residue.

As Nik-1, Sln1p and Doka have been shown to be associated with osmosensing, CaHK-1 may also be associated with this process in *C. albicans*. On the other hand, its similarity with virulence factor regulators such as the BvgS from *B. pertussis* and LemA from *P. syringae,* may indicate that the CaHK-1 gene could play a key role in the regulation of the virulence in *C. albicans*.

CaHK-1 polynucleotides can be used in an expression system for producing CaHK-1 protein in sufficient quantities for use in assays. The in vitro assay involves measuring the activity of the CaHK-1 protein in the presence of putative inhibitory compounds. The activity of the CaHK-1 protein in the presence of each compound is measured and compared to untreated CaHK-1. The CaHK-1 protein transfers phosphate to a second protein (acceptor protein). The activity of the CaHK-1 is measured by the transfer of radiolabeled phosphate from CaHK-1 to the acceptor protein. This method provides a ready means for testing the inhibitory potential of such compounds before testing as described below.

Antibodies which specifically bind/recognize CaHK-1 polypeptides may be used in immunoassays to detect the presence of *C. albicans* in biological samples including but not limited to tissues, smears, and fluids (e.g. urine, blood, saliva).

In the second phase, active compounds that are inhibitory can be tested in vitro against cells of the organism to determine if the compound inhibits growth of the Candida organism. Inhibitory compounds characterized through these studies can then be tested in animal models for candidiasis.

Nucleic Acid Molecules

The present invention also relates to recombinant vectors including, which include the isolated nucleic acid molecules of the present invention or fragments thereof. The present invention also relates to host cells containing the recombinant vectors, as well as to methods of making such vectors and host cells and for using them for production of CaHK-1 polypeptides or peptides by recombinant techniques. In another aspect, the invention provides isolated nucleic acid molecules encoding the CaHK-1 polypeptide having an amino acid sequence encoded by the cDNA clone contained in the plasmid deposited on 26 Nov. 1997 under the Terms of the Budapest Treaty with the American Type Culture Collection (ATCC), located at 10801 University Boulevard, Manassas, Va. 20110-2209, as ATCC Deposit Nos. 209504 and 209505.

In addition, isolated nucleic acid molecules of the invention include DNA molecules which comprise a sequence substantially different from those described above but which, due to the degeneracy of the genetic code, still encode the CaHK-1 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the CaHK-1 polypeptide having an amino acid sequence encoded by the cDNA clone contained in the plasmid deposited as ATCC Deposit No.s 209504 and 209505.

Unless otherwise indicated, each "nucleotide sequence" set forth herein is presented as a sequence of deoxyribonucleotides (abbreviated A, G , C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The invention further provides an isolated nucleic acid molecule having the nucleotide sequence shown in FIG. 1A and FIGS. 4A–D (SEQ ID NO: 1 and SEQ ID NO:3 respectively) or a nucleic acid molecule having a sequence complementary to one of the above sequences. Such isolated molecules, particularly DNA molecules, are useful as probes for gene mapping and for identifying *C, albicans* a biological sample, for instance, by PCR, Southern blot, Northern blot, or other form of hybridization analysis.

The present invention is further directed to nucleic acid molecules encoding portions or fragments of the nucleotide sequences described herein. Fragments include portions of the nucleotide sequences of FIGS. 1A or 4A–C (SEQ ID NO: 1 and SEQ ID NO:3 respectively) at least 10 contiguous nucleotides in length selected from any two integers, one of which representing a 5' nucleotide position and a second of which representing a 3' nucleotide position, where the first nucleotide for each nucleotide sequence in FIGS. 1A or 4A–C (SEQ ID NO: 1 and SEQ ID NO:3 respectively) is position 1. That is, every combination of a 5' and 3' nucleotide position that a fragment at least 10 contiguous nucleotides in length could occupy is included in the invention. "At least" means a fragment may be 10 contiguous nucleotide bases in length or any integer between 10 and the length of an entire nucleotide sequence of FIGS. 1A or 4A–C (SEQ ID NO: 1 and SEQ ID NO:3 respectively) minus 1. For example, for SEQ ID NO:3 fragment sizes include any interger between 10 and 8555 in length specified by 5' and 3' positions. Therefore, included in the invention are contiguous fragments specified by any 5' and 3' nucleotide base positions of a nucleotide sequences of FIGS. 1A or 4–C (SEQ ID NO: 1 and SEQ ID NO:3 respectively) wherein the contiguous fragment is any integer between 10 and the length of an entire nucleotide sequence minus 1.

Further, the invention includes polynucleotides comprising fragments specified by size, in nucleotides, rather than by nucleotide positions. The invention includes any fragment size, in contiguous nucleotides, selected from integers between 10 and the length of an entire nucleotide sequence minus 1. For example, for SEQ ID NO:3 fragment sizes include any interger between 10 and 8555 in length. Preferred sizes of contiguous nucleotide fragments include 20 nucleotides, 30 nucleotides, 40 nucleotides, 50 nucleotides. Other preferred sizes of contiguous nucleotide fragments, which may be useful as diagnostic probes and primers, include fragments 50, 100, 150, 200, 250, and 300 nucleotides in length which include, as discussed above, fragment sizes representing each integer between 50–300. Larger fragments are also useful according to the present invention corresponding to most, if not all, of the nucleotide sequences shown in FIGS. 1A or 4A–C (SEQ ID NO: 1 and SEQ ID NO:3 respectively). The preferred sizes are, of course, meant to exemplify not limit the present invention as all size fragments, representing any integer between 10 and the length of an entire nucleotide sequence minus 1, are included in the invention. Additional preferred nucleic acid fragments of the present invention include nucleic acid molecules encoding epitope-bearing portions of CaHK-1 polypeptides of the present invention. Other preferred nucleic acid fragments of the present invention also include nucleic acid molecules comprising sequences encoding the residues comprising epitope-bearing portions of the CaHK-1 polypeptides shown in Table 1.

The present invention also provides for the exclusion of any fragment, specified by 5' and 3' base positions or by size in nucleotide bases as described above for the nucleotide sequences of FIGS. 1A or 4A–C (SEQ ID NO: 1 and SEQ ID NO:3 respectively). Any number of fragments of nucleotide sequences in FIGS. 1A or 4A–C (SEQ ID NO: 1 and SEQ ID NO:3 respectively) or specified fragmented thereof, specified by 5' and 3' base positions or by size in nucleotides, as described above, may be excluded from the present invention.

In another aspect, the invention provides isolated nucleic acid molecules comprising polynucleotides which hybridize under stringent hybridization conditions to a polynucleotide sequence of the present invention described above, for instance, a nucleic acid sequence shown in FIGS. 1A or 4A–C (SEQ ID NO: 1 and SEQ ID NO:3 respectively) or specified fragment thereof. By "stringent hybridization conditions" is intended overnight incubation at 42 C in a solution comprising: 50% formamide, 5x SSC (150 mM NaCl, 15 mM trisodium citrate), 50 mM sodium phosphate (pH 7.6), 5x Denhardt's solution, 10% dextran sulfate, and 20 g/ml denatured, sheared salmon sperm DNA, followed by washing the filters in 0.1 x SSC at about 65 C.

These polynucleotides are useful as diagnostic probes and primers as discussed above and in more detail below. Hybridizing polynucleotide fragments of the present invention are useful diagnostically either as probes according to conventional DNA hybridization techniques or as primers for amplification of a target sequence by PCR, as described, for instance, in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Variant and Mutant Polynucleotides

Since nucleic acid sequences encoding the CaHK-1 polypeptides of the present invention are provided in FIGS. 1B or 4D (SEQ ID NO: 1 and SEQ ID NO:3 respectively), generating polynucleotides which hybridize to portions of these sequences would be routine to the skilled artisan. For example, the hybridizing polynucleotides of the present invention could be generated synthetically according to known techniques.

Nucleic acid molecules of the present invention which encode CaHK-1 polypeptides of the present invention may include, but are not limited to those encoding the amino acid sequences of the polypeptides by themselves; and additional coding sequences which code for additional amino acids, such as those which provide additional functionalities. Thus, the sequences encoding these polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al, *Proc. Natl. Acad. Sci. USA* 86:821–824 (1989), for instance, hexa-histidine provides for convenient purification of the resulting fusion protein.

Thus, the present invention also includes genetic fusions wherein the CaHK-1 nucleic acid sequences coding sequences provided in FIGS. 1A–B and 4A–D (SEQ ID NO: 1 and SEQ ID NO:3 respectively) are linked to additional nucleic acid sequences to produce fusion proteins. These fusion proteins may include epitopes of Candidal or non-Candidal origin designed to produce proteins having enhanced immunogenicity or stability. Further, the fusion proteins of the present invention may contain antigenic determinants known to provide helper T-cell stimulation, peptides encoding sites for post-translational modifications which enhance immunogenicity (e.g., acylation), peptides which facilitate purification (e.g., histidine "tag"), or amino acid sequences which target the fusion protein to a desired location (e.g., a heterologous leader sequence). For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al. (1984) Cell 37:767. As discussed below, other such fusion proteins include the CaHK-1 polypeptides of the present invention fused to an immunoglobulin, Fc, or portion thereof, at the N- or C-terminus.

The present invention thus includes nucleic acid molecules and sequences which encode fusion proteins comprising one or more CaHK-1 polypeptides of the present invention fused to an amino acid sequence which allows for post-translational modification to enhance immunogenicity. This post-translational modification may occur either in vitro or when the fusion protein is expressed in vivo in a host cell. An example of such a modification is the introduction of an amino acid sequence which results in the attachment of a lipid moiety. Such a lipid moiety attachment site of OspA, which is lipidated upon expression in *E. coli*, has been identified. Bouchon, B. et al, *Anal. Biochem.* 246:52–61 (1997).

Thus, as indicated above, the present invention includes genetic fusions wherein a CaHK-1 nucleic acid sequence provided in FIGS. 1A and 4A–C (SEQ ID NO: 1 and SEQ ID NO:3 respectively) is linked to a nucleotide sequence encoding a heterologous amino acid sequence. These other amino acid sequences may be of Candidal origin or non-Candidal origin.

The present invention further relates to variants of the nucleic acid molecules of the present invention, which encode portions, analogs or derivatives of the CaHK-1 polypeptides shown in FIGS. 1B and 4D (SEQ ID NO: 1 and SEQ ID NO:3 respectively). Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. These variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the CaHK-1 polypeptides disclosed herein or portions thereof. Also especially preferred in this regard are conservative substitutions.

The present application is further directed to nucleic acid molecules at least 90%, 95%, 96%, 97%, 98% or 99% identical to a nucleic acid sequence shown in FIGS. 1A and 4A–C (SEQ ID NO: I and SEQ ID NO:3 respectively). The above nucleic acid sequences are included irrespective of whether they encode a polypeptide having CaHK-1 activity. This is because even where a particular nucleic acid molecule does not encode a polypeptide having CaHK-1 activity, one of skill in the art would still know how to use the nucleic acid molecule, for instance, as a hybridization probe. For example, uses of the nucleic acid molecules of the present invention that do not encode a polypeptide having CaHK-1 activity include, inter alia, isolating an CaHK-1 gene or allelic variants thereof from a DNA library, and detecting CaHK-1 mRNA expression samples, environmental samples, suspected of containing C albicans by Northern Blot analysis.

Embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding an amino acid sequence of the full-length polypeptides shown in FIGS. 1B and 4D (SEQ ID NO:2 and SEQ ID NO:4 respectively); (b) a nucleotide sequence encoding any of the amino acid sequences of the full-length polypeptides shown in FIGS. 1B and 4D (SEQ ID NO:2 and SEQ ID NO:4 respectively), but minus the N-terminal methionine residue; and (c) a nucleotide sequence complementary to any of the nucleotide sequences in (a) or (b) above.

Preferred, are nucleic acid molecules having sequences at least 90%, 95%, 96%, 97%, 98% or 99% identical to the nucleic acid sequence shown in FIGS. 1A and 4A–C (SEQ ID NO: 1 and SEQ ID NO:3 respectively), which do, in fact, encode a polypeptide having CaHK-1 protein activity By "a polypeptide having CaHK-1 activity" is intended polypeptides exhibiting activity similar, but not necessarily identical, to an activity of the CaHK-1 protein of the invention, as measured in a particular biological assay known in the art, e.g. the kinase assays described in Huang J. et al. 1992 J. Biol. Chem. 267(22):15511–15515.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences shown in FIGS. 1A and 4A–C (SEQ ID NO: 1 and SEQ ID NO:3 respectively) will encode a polypeptide having CaHK-1 protein activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CaHK-1 protein activity. This is because the skilled artisan is fully aware of amino acid substitutions that are either less likely or not likely to significantly effect protein function (e.g., replacing one aliphatic amino acid with a second aliphatic amino acid), as further described below. The biological activity or function of the polypeptides of the present invention are expected to be similar or identical to polypeptides from other organisms that share a high degree of structural identity/similarity, such as those discussed herein.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the CaHK-1 polypeptide. In other words, to obtain a polynucleotide having a nucleotide sequence at least 95% identical to a reference nucleotide sequence, up to 5% (5 of 100) of the nucleotides in the reference sequence may be deleted, inserted, or substituted with another nucleotide. The query sequence may be an entire sequence shown in FIGS. 1A and 4A–C (SEQ ID NO: 1 and SEQ ID NO:3 respectively), the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are to made for the purposes of the present invention.

Vectors and Host Cells

The present invention also relates to vectors which include the isolated DNA molecules of the present invention, host cells which are genetically engineered with the recombinant vectors, and the production of CaHK-1 polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral, cosmid, YAC, or vector including adenoviral and retroviral vectos. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, fungal cells, including yeast cells, such as *Candida albicans* and Saccharomyces cerevisiae; bacterial cells, such as *E. coli,* Streptomyces and *Salmonella typhimurium* cells; insect cells such as Drosophila S2 and Spodoptera Sf9 cells; animal cells such as HeLa, L, F9, CHO, COS and Bowes melanoma cells; and plant cells. Appropriate culture mediums and conditions for the above-described host cells are known in the art.

Also included in the present invention are *Candida albicans* cells with heterozygous or homozygous (null) mutations including knockout deletions, insertions, or substitutions. Further included are mutations that increase, reduce, or eliminate CaHK-1 activity. These mutant strains of *C. albicans* are useful in virulence studies and in drug screening methods to identity and assay drugs, including agonist and antagonist, that target CaHK-1.

Among vectors preferred for use in bacteria include pQE70, pQE60 and pQE-9, available from Qiagen; pBS vectors, Phagescript vectors, Bluescript vectors, pNH8A, pNH 16a, pNH18A, pNH46A available from Stratagene; pET series of vectors available from Novagen; and ptrc99a, pKK223–3, pKK233–3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al, *Basic Methods In Molecular Biology* (1986).

Transcription of DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide (e.g. KDEL). The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al., *J. Molec. Recogn.* 8:52–58 (1995) and Johanson, K. et al., *J. Biol. Chem.* 270 (16):9459–9471 (1995).

The CaHK-1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Polypeptides and Fragments

The invention further provides isolated polypeptides having the amino acid sequences in FIGS. 1B and 4D (SEQ ID NO:2 and SEQ ID NO:4 respectively), and peptides or polypeptides comprising portions of the above polypeptides. The terms "peptide" and "oligopeptide" are considered synonymous (as is commonly recognized) and each term can be used interchangeably as the context requires to indicate a chain of at least two amino acids coupled by peptidyl linkages. All oligopeptide and polypeptide formulas or sequences herein are written from left to right and in the direction from amino terminus to carboxy terminus.

Variant and Mutant Polypeptides

To improve or alter the characteristics of CaHK-1 polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

It is known in the art that one or more amino acids may be deleted from the N-terminus or C-terminus without substantial loss of biological function. For instance, Ron et al. J. Biol. Chem., 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the amino acid sequence of the CaHK-1 polypeptides and polynucleotides of the present invention.

Similarly, many examples of biologically functional C-terminal deletion muteins are known. For instance, Interferon gamma shows up to ten times higher activities by deleting 8–10 amino acid residues from the carboxy terminus of the protein See, e.g., Dobeli, et al. (1988) J. Biotechnology 7:199–216. Accordingly, the present invention provides polypeptides having one or more residues from the carboxy terminus of the amino acid sequence of the CaHK-1 polypeptides of the present invention. The invention also provides polypeptides having one or more amino acids deleted from both the amino and the carboxyl termini as described below.

The present invention is further directed to polynucleotides encoding portions or fragments of the amino acid sequences described herein as well as to portions or fragments of the isolated amino acid sequences described herein. Fragments include portions of the amino acid sequences of FIGS. 1B and 4D (SEQ ID NO:2 and SEQ ID NO:4 respectively), at least 7 contiguous amino acid in length, selected from any two integers, one of which representing the N-terminal position. The first N-terminal and the other representing the C-terminal position of the fragment codon of the polypeptides of the FIGS. 1B and 4D (SEQ ID NO:2 and SEQ ID NO:4 respectively) is position 1. Every combination of a N-terminal and C-terminal position that a fragment at least 7 contiguous amino acid residues in length could occupy, on any given amino acid sequence of FIGS. 1B and 4D (SEQ ID NO:2 and SEQ ID NO:4 respectively) is included in the invention. At least means a fragment may be 7 contiguous amino acid residues in length or any integer between 7 and the number of residues in a full length amino acid sequence minus 1. For example, for SEQ ID NO:4 "at least" means a fragment between 7 and 2470 residues in length. Therefore, included in the invention are contiguous fragments specified by N-terminal and C-terminal position STET of amino acid sequences set forth in FIGS. 1B and 4D (SEQ ID NO:2 and SEQ ID NO:4 respectively) wherein the contiguous fragment is any integer between 7 and the number of residues in a full length sequence minus 1.

Further, the invention includes polypeptides comprising fragments specified by size, in amino acid residues, rather than by N-terminal and C-terminal positions. The invention includes any fragment size, in contiguous amino acid residues, selected from integers between 7 and the number of residues in a full length sequence minus 1. For example, for SEQ ID NO:4 fragment sizes between the integers of 7 and 2470 residues in length are included in the present invention. Preferred sizes of contiguous polypeptide fragments include about 7 amino acid residues, about 10 amino acid residues, about 20 amino acid residues, about 30 amino acid residues, about 40 amino acid residues, about 50 amino acid residues, about 100 amino acid residues, about 200 amino acid residues, about 300 amino acid residues, and about 400 amino acid residues. The preferred sizes are, of course, meant to exemplify, not limit, the present invention as all size fragments representing any integer between 7 and the number of residues in a full length sequence minus 1 are included in the invention. The present invention also provides for the exclusion of any fragments specified by N-terminal and C-terminal positions or by size in amino acid residues as described above Any number of fragments specified by N-terminal and C-terminal positions or by size in amino acid residues as described above may be excluded.

The above fragments need not be active since they would be useful, for example, in immunoassays, in epitope mapping, epitope tagging, to generate antibodies to a particular portion of the protein, as vaccines, and as molecular weight markers in gel electrophoresis and column chromatography.

Other Mutants

In addition to N- and C-terminal deletion forms of the protein discussed above, it also will be recognized by one of ordinary skill in the art that some amino acid sequences of the CaHK-1 polypeptides can be varied without significant effect of the structure or function of the protein. If such differences in sequence are contemplated, it should be remembered that there will be critical areas on the protein which determine activity.

Thus, the invention further includes variations of the CaHK-1 polypeptides which show substantial CaHK-1 polypeptide activity or which include regions of CaHK-1 polypeptides such as the protein portions discussed below. Such mutants include deletions, insertions, inversions, repeats, and type substitutions selected according to general rules known in the art so as to have little effect on activity. For example, guidance concerning how to make phenotypically silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative, analog, or homolog of the polypeptides of FIGS. 1B and 4D (SEQ ID NO:2 and SEQ ID NO:4 respectively), may be: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the CaHK-I polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein. Thus, the CaHK-1 polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein.

Amino acids in the CaHK-1 polypeptides of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and preferably are substantially purified. A recombinantly produced version of the CaHK-1 polypeptide can be substantially purified by the one-step method described by Smith et al. (1988) Gene 67:3140. Polypeptides of the invention also can be purified from natural or recombinant sources using antibodies directed against the polypeptides of the invention in methods which are well known in the art of protein purification.

The invention further provides for isolated CaHK-1 polypeptides comprising an amino acid sequence selected from the group consisting of: (a) the amino acid sequence of a full-length CaHK-1 polypeptide having the complete amino acid sequence shown in FIGS. 1B and 4D (SEQ ID NO:2 and SEQ ID NO:4 respectively); (b) the amino acid sequence of a full-length CaHK-1 polypeptide having the complete amino acid sequence shown in FIGS. 1B and 4D (SEQ ID NO:2 and SEQ ID NO:4 respectively) excepting the N-terminal methionine; (c) the complete amino acid sequence encoded by the plasmids listed in FIGS. 1B and 4A–D (SEQ ID NO:2 and SEQ ID NO:4 respectively); and (d) the complete amino acid sequence excepting the N-terminal methionine encoded by the plasmids contained in ATCC Deposit No.s 209504 and 209505. The polypeptides of the present invention also include polypeptides having an amino acid sequence at least 80% identical, more preferably at least 90% identical, and still more preferably 95%, 96%, 97%, 98% or 99% identical to those described in (a), (b), (c), and (d) above.

Further polypeptides of the present invention include polypeptides which have at least 90% similarity, more preferably at least 95% similarity, and still more preferably at least 96%, 97%, 98% or 99% similarity to those described above.

A further embodiment of the invention relates to a polypeptide which comprises the amino acid sequence of a CaHK-1 polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a CaHK-1 polypeptide, having at least one, but not more than 10, 9, 8, 7, 6, 5, 4, 3, 2 or I conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in FIGS. 1B and 4D (SEQ ID NO:2 and SEQ ID NO:4 respectively), a specified fragment thereof, or to the amino acid sequence encoded by the plasmids contained in ATCC Deposit No.s 209504 and 209505 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=l, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have CaHK-1 activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting *C. albicans* or CaHK-1 protein expression, or as agonists and antagonists capable of enhancing or inhibiting CaHK-1 protein function. Further, such polypeptides can be used in the yeast two-hybrid system to "capture" CaHK-1 protein binding proteins which are also candidate agonists and antagonists according to the present invention. See, e.g., Fields et al. (1989) Nature 340:245–246.

Epitope-Bearing Portions

In another aspect, the invention provides peptides and polypeptides comprising epitope-bearing portions of the CaHK-1 polypeptides of the present invention. These epitopes are immunogenic or antigenic epitopes of the polypeptides of the present invention. An "immunogenic epitope" is defined as a part of a protein that elicits an antibody response when the whole protein or polypeptide is the immunogen. On the other hand, a region of a protein molecule to which an antibody can bind is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:3998–4002. Predicted residues comprising antigenic epitopes are shown in Table 1, below. It is pointed out that Table 1 only lists amino acid residues comprising epitopes predicted to have the highest degree of antigenicity. The polypeptides not listed in Table 1 and portions of polypeptides not listed in Table 1 are not considered non-antigenic. This is because they may still be antigenic in vivo but merely not recognized as such by the particular algorithm used. Thus, Table 1 lists the amino acid residues comprising preferred antigenic epitopes but not a complete list. Amino acid residues comprising other anigenic epitopes may be determined by algorithms similar to the Jameson-Wolf analysis or by in vivo testing for an antigenic response using the methods described herein or those known in the art.

TABLE 1

Residues Comprising Antigenic Epitope-Bearing Portions of CaHK-1.

From about Thr-148 to about Lys-152, from about Arg-192 to about Asn-195,
from about Thr-364 to about Lys-367, from about Asp-375 to about Tyr-378,
from about Glu-403 to about Ser-408, from about Arg-528 to about Lys-530,
from about Arg-624 to about Thr-626, from about Asn-705 to about Asn-709, TABLE 1-continued Residues Comprising Antigenic Epitope-Bearing Portions of CaHK-1.

from about Gly-721 to about Gly-723, from about Asn-959 to about Lys-962,
from about Pro-976 to about Asn-978, from about Lys-1351 to about Arg-1354,
from about Gly-1373 to about Asp-1375, from about Pro-1778 to about Asn-1780,
from about Asp-1805 to about Gln-1807, from about Asp-1921 to about Lys-1923,
from about Asp-2139 to about Arg-2141.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, et al., (1983) Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. See, Sutcliffe, et al., supra, p. 661. For instance, 18 of 20 peptides designed according to these guidelines, containing 8–39 residues covering 75% of the sequence of the influenza virus hemagglutinin HA 1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. See Sutcliffe, et al., supra, p. 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, e.g., Wilson, et al., (1984) Cell 37:767–778. The anti-peptide antibodies of the invention also are useful for purification of the mimicked protein, for instance, by adsorption chromatography using methods known in the art.

Antigenic epitope-bearing peptides and polypeptides of the invention designed according to the above guidelines preferably contain a sequence of at least seven, more preferably at least nine and most preferably between about 10 to about 50 amino acids (i.e. any integer between 7 and 50) contained within the amino acid sequence of a polypeptide of the invention. However, peptides or polypeptides comprising a larger portion of an amino acid sequence of a polypeptide of the invention, containing about 50 to about 100 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate an Candida-specific immune response or antibodies include portions of the amino acid sequences identified in FIGS. 1B and 4D (SEQ ID NO:2 and SEQ ID NO:4 respectively). More specifically, Table 1 discloses a list of non-limiting residues that are involved in the antigenicity of the epitope-bearing fragments of the present invention. Therefore, the present inventions provides for isolated and purified antigenic epitope-bearing fragments of the polypeptides of the present invention comprising a peptide sequences of Table 1. The antigenic epitope-bearing fragments comprising a peptide sequence of Table 1 preferably contain a sequence of at least seven, more preferably at least nine and most preferably between about 10 to about 50 amino acids (i.e. any integer between 7 and 50) of a polypeptide of the present invention. That is, included in the present invention are antigenic polypeptides between the integers of 7 and 50 amino acid in length comprising one or more of the sequences of Table 1. Therefore, in most cases, the polypeptides of Table 1 make up only a portion of the antigenic epitope-bearings STET. All combinations of sequences between the integers of 7 and 50 amino acid in length comprising one or more of the sequences of Table 1 are included. The antigenic epitope-bearing fragments may be specified by either the number of contiguous amino acid residues or by specific N-terminal and C-terminal positions as described above for the polypeptide fragments of the present invention. Any number of the described antigenic epitope-bearing fragments of the present invention may also be excluded from the present invention in the same manner.

The epitope-bearing peptides and polypeptides of the invention may be produced by any conventional means for making peptides or polypeptides including recombinant means using nucleic acid molecules of the invention. For instance, an epitope-bearing amino acid sequence of the present invention may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HAI polypeptide which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing peptides and polypeptides of the invention are used to induce antibodies according to methods well known in the art. See, e.g., Sutcliffe, et al., supra;; Wilson, et al., supra;; and Bittle, et al. (1985) J. Gen. Virol. 66:2347–2354. Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen, et al, supra, discloses a procedure for rapid concurrent synthesis on solid supports of hundreds of peptides of sufficient purity to react in an ELISA. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method.

U.S. Pat. No. 4,708,781 to Geysen (1987) further describes this method of identifying a peptide bearing an immunogenic epitope of a desired protein.

Further still, U.S. Pat. No. 5,194,392, to Geysen (1990), describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, also to Geysen (1989), describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods. The entire disclosure of each document cited in this section on "Polypeptides and Fragments" is hereby incorporated herein by reference.

As one of skill in the art will appreciate, the polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4polypeptide and various domains of the constant regions of the heavy or light chains of mammalian immunoglobulins. (EPA 0,394,827; Traunecker et al. (1988) Nature 331:84–86. Fusion proteins that have a disulfide-linked dimeric structure due to the IgG part can also be more efficient in binding and neutralizing other molecules than a monomeric CaHK-1 polypeptide or fragment thereof alone. See Fountoulakis et al. (1995) J. Biochem. 270:3958–3964. Nucleic acids encoding the above epitopes of CaHK-1 polypeptides can also be recombined with a gene of interest as an epitope tag to aid in detection and purification of the expressed polypeptide.

Antibodies

CaHK-1 protein-specific antibodies for use in the present invention can be raised against the intact CaHK-1 polypeptide or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules, single chain whole antibodies, and antibody fragments. Antibody fragments of the present invention include Fab and F(ab')2 and other fragments including single-chain Fvs (scFv) and disulfide-linked Fvs (sdFv). Also included in the present invention are chimeric and humanized monoclonal antibodies and polyclonal antibodies specific for the polypeptides of the present invention. The antibodies of the present invention may be prepared by any of a variety of methods. For example, cells expressing a polypeptide of the present invention or an antigenic fragment thereof can be administered to an animal in order to induce the production of sera containing polyclonal antibodies. For example, a preparation of a CaHK-1 polypeptide or fragment thereof is prepared and purified to render it substantially free of natural contaminants. Such a preparation is then introduced into an animal in order to produce polyclonal antisera of greater specific activity.

In a preferred method, the antibodies of the present invention are monoclonal antibodies or binding fragments thereof. Such monoclonal antibodies can be prepared using hybridoma technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981). Fab and F(ab')2 fragments may be produced by proteolytic cleavage, using enzymes such as papain (to produce Fab fragments) or pepsin (to produce F(ab')2 fragments). Alternatively, CaHK-1 polypeptide-binding fragments, chimeric, and humanized antibodies can be produced through the application of recombinant DNA technology or through synthetic chemistry using methods known in the art.

Alternatively, additional antibodies capable of binding to a polypeptide antigen of the present invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CaHK-1 polypeptide-specific antibodies are used to immunize an animal, preferably a mouse. The splenocytes of such an animal are then used to produce hybridoma cells, and the hybridoma cells are screened to identify clones which produce an antibody whose ability to bind to the CaHK-1 polypeptide-specific antibody can be blocked by the CaHK-1 polypeptide antigen. Such antibodies comprise anti-idiotypic antibodies to the CaHK-1 spolypeptide-specific antibody and can be used to immunize an animal to induce formation of further CaHK-1 polypeptide-specific antibodies.

Antibodies and fragements thereof of the present invention may be described by the portion of a polypeptide of the present invention recognized or specifically bound by the antibody. Antibody binding fragements of a polypeptide of the present invention may be described or specified in the same manner as for polypeptide fragements discussed above., i.e, by N-terminal and C-terminal positions or by size in contiguous amino acid residues. Any number of antibody binding fragments, of a polypeptide of the present invention, specified by N-terminal and C-terminal positions or by size in amino acid residues, as described above, may also be excluded from the present invention. Therefore, the present invention includes antibodies the specifically bind a particularly described fragment of a polypeptide of the present invention and allows for the exclusion of the same.

Antibodies and fragements thereof of the present invention may also be described or specified in terms of their cross-reactivity. Antibodies and fragements that do not bind polypeptides of any other species of Candida other than *C. albicans* are included in the present invention. Likewise, antibodies and fragements that bind only species of Candida, i.e. antibodies and fragements that do not bind yeast/fungi from any genus other than Candida, are included in the present invention.

Diagnostic Assays

The present invention further relates to methods for assaying Candidal infection in an animal by detecting the expression of genes encoding polypeptides of the present invention. The methods comprise analyzing tissue or body fluid from the animal for Candida specific antibodies, nucleic acids, or proteins. Analysis of nucleic acid specific to Candida is assayed by PCR or hybridization techniques using nucleic acid sequences of the present invention as either hybridization probes or primers. See, e.g., Sambrook et al. Molecular cloning: A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group Rickettsiae species by analysis of restriction fragment length polymorphism of PCR-amplified DNA) and Chen et al. 1994 J. Clin. Microbiol. 32:589–595 (detecting bacterial nucleic acids via PCR).

Where diagnosis of a disease state related to infection with Candida has already been made, the present invention is useful for monitoring progression or regression of the disease state whereby patients exhibiting enhanced CaHK-1 gene expression will experience a worse clinical outcome relative to patients expressing these gene(s) at a lower level. The present invention is also useful for monitoring the progression or regression of the disease state whereby the presence of Candida is indicated either quantitatively or qualitatively by detecting CaHK-1 gene expression.

By "biological sample" is intended any biological sample obtained from an animal, cell line, tissue culture, or other source which contains Candida polypeptide, mRNA, or DNA.

Biological samples include body fluids (such as saliva, blood, plasma, urine, mucus, synovial fluid, etc.) tissues (such as muscle, skin, and cartilage) and any other biological source suspected of containing CaHK-1 polypeptides or nucleic acids. Methods for obtaining biological samples such as tissue are well known in the art.

The present invention is useful for detecting diseases related to Candida infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidinium-thiocyanate-phenol-chloroform method described in Chomczynski et al. (1987) Anal. Biochem. 162:156–159. mRNA encoding CaHK-1 polypeptides having sufficient homology to the nucleic acid sequences identified in FIGS. 1 and 4 (SEQ ID NO:2 and SEQ ID NO:4 respectively) to allow for hybridization between complementary sequences are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A polynucleotide sequence of the present invention, labeled according to any appropriate method (such as the $^{32}$P-multiprimed DNA labeling system (Amersham)), is used as probe. After hybridization overnight, the filter is washed and exposed to x-ray film. DNA for use as probe according to the present invention is described in the sections above.

S1 mapping can be performed as described in Fujita et al. (1987) Cell 49:357–367. To prepare probe DNA for use in S1 mapping, the sense strand of an above-described CaHK-1 sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding CaHK-1 polypeptides).

Levels of mRNA encoding CaHK-1 polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the CaHK-1 polypeptides of the present invention) are quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995). Also included in the present invention are methods of detecting polypeptides sequences and Candida species, including, C albican, using Real-time Quantitative PCR (see e.g. U.S. Pat. No. 5,210,015) using, for example, ABI PRISM® 7700 Sequence Detection System by Perkin-Elmer Applied Biosystems.

The polynucleotides of the present invention, including both DNA and RNA, may be used to detect polynucleotides of the present invention or Candida species including C. albicans using bio chip technology. The present invention includes both high density chip arrays (>1000 oligonucleotides per cm$^2$) and low density chip arrays (<1000 oligonucleotides per cm$^2$). Bio chips comprising arrays of polynucleotides of the present invention may be used to detect the same or Candida species, including C. albicans, in biological and environmental samples and to diagnose an animal, including humans, with an C. albicans or other Candida infections. The bio chips of the present invention may comprise polynucleotide sequences of other pathogens including bacteria, viral, parasitic, and fungal polynucleotide sequences, in addition to the polynucleotide sequences of the present invention, for use in rapid differential pathogenic detection and diagnosis. The bio chips can also be used to monitor an C. albicans or other Candida infections and to monitor the genetic changes (deletions, insertions, mismatches, etc.) in response to drug therapy in the clinic and drug development in the laboratory. The bio chip technology comprising arrays of polynucleotides of the present invention may also be used to simultaneously monitor the expression of a multiplicity of genes, including those of the present invention. The polynucleotides used to comprise a selected array may be specified in the same manner as for the fragements, i.e, by their 5' and 3' positions or length in contigious base pairs and include from. Methods and particular uses of the polynucleotides of the present invention to detect the same or Candida species, including C. albicans, using bio chip technology include those known in the art and those of: U.S. Pat. Nos. 5,510,270, 5,545,531, 5,445,934, 5,677,195, 5,532,128, 5,556,752, 5,527,681, 5,451,683, 5,424,186, 5,607,646, 5,658,732 and World Patent Nos. WO/9710365, WO/9511995, WO/9743447, WO/9535505, each incorporated herein in their entireties.

Biosensors using the polynucleotides of the present invention may also be used to detect, diagnose, and monitor C.

albicans or other Candida species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. Methods and particular uses of the polynucleotides of the present invention to detect Candy species, including C. albicans, using biosenors include those known in the art and those of: U.S. Pat. Nos. 5,721,102, 5,658,732, 5,631,170, and World Patent Nos. WO97/3501 1, WO/9720203, each incorporated herein in their entireties.

Thus, the present invention includes both bio chips and biosensors comprising polynucleotides of the present invention and methods of their use.

Assaying CaHK-1 polypeptide levels in a biological sample can occur using any art-known method, such as antibody-based techniques. For example, CaHK-1 polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of CaHK-1 polypeptides for Western-blot or dot/slot assay. See, e.g., Jalkanen, M. et al. (1985) J. Cell. Biol. 101:976–985; Jalkanen, M. et al. (1987) J. Cell . Biol. 105:3087–3096. In this technique, which is based on the use of cationic solid phases, quantitation of a CaHK-1 polypeptide can be accomplished using an isolated CaHK-1 polypeptide as a standard. This technique can also be applied to body fluids.

Other antibody-based methods useful for detecting CaHK-1 polypeptide gene expression include immunoassays, such as the ELISA and the radioimmunoassay (RIA). For example, a CaHK-1 polypeptide-specific monoclonal antibodies can be used both as an immunoabsorbent and as an enzyme-labeled probe to detect and quantify a CaHK-1 polypeptide. The amount of a CaHK-1 polypeptide present in the sample can be calculated by reference to the amount present in a standard preparation using a linear regression computer algorithm. Such an ELISA is described in Iacobelli et al. (1988) Breast Cancer Research and Treatment 11:19–30. In another ELISA assay, two distinct specific monoclonal antibodies can be used to detect CaHK-1 polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the CaHK-1 polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^3$H), indium ($^{112}$In), and technetium ($^{99m}$Tc), and fluorescent labels, such as fluorescein and rhodamine, and biotin.

Further suitable labels for the CaHK-1 polypeptide-specific antibodies of the present invention are provided below. Examples of suitable enzyme labels include malate dehydrogenase, a bacterial nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, $^{99m}$Tc etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxysuccinimide ester method, all of which methods are incorporated by reference herein.

In a related aspect, the invention includes a diagnostic kit for use in screening serum containing antibodies specific against C. albicans infection. Such a kit may include an isolated CaHK-1 antigen comprising an epitope which is specifically immunoreactive with at least one anti-CaHK-1 antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the CaHK-1 antigen can be detected by binding of the reporter labeled antibody to the anti-CaHK-1 polypeptide antibody.

In a related aspect, the invention includes a method of detecting C. albicans infection in a subject. This detection method includes reacting a body fluid, preferably serum, from the subject with an isolated CaHK-1 antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein , typically through a free amine group, to a chemically reactive group on the solid support, such as an activated carboxyl, hydroxyl, or aldehyde group. Alternatively, streptavidin coated plates can be used in conjunction with biotinylated antigen(s).

The polypeptides and antibodies of the present invention, including fragments thereof, may be used to detect Candida species including C. albicans using bio chip and biosensor technology. Bio chip and biosensors of the present invention may comprise the polypeptides of the present invention to detect antibodies, which specifically recognize Candida species, including C. albicans. Bio chip and biosensors of the present invention may also comprise antibodies which specifically recognize the polypeptides of the present invention to detect Candida species, including C. albicans or specific polypeptides of the present invention. Bio chips or biosensors comprising polypeptides or antibodies of the present invention may be used to detect Candida species, including C. albicans, in biological and environmental samples and to diagnose an animal, including humans, with an C. albicans or other Candida infection. Thus, the present invention includes both bio chips and biosensors comprising polypeptides or antibodies of the present invention and methods of their use.

The bio chips of the present invention may further comprise polypeptide sequences of other pathogens including bacteria, viral, parasitic, and fungal polypeptide sequences, in addition to the polypeptide sequences of the present invention, for use in rapid differential pathogenic detection and diagnosis. The bio chips of the present invention may further comprise antibodies or fragements thereof specific for other pathogens including bacteria, viral, parasitic, and fungal polypeptide sequences, in addition to the antibodies or fragements thereof of the present invention, for use in rapid differential pathogenic detection and diagnosis. The bio chips and biosensors of the present invention may also be used to monitor an C. albicans or other Candida infection and to monitor the genetic changes (amino acid deletions, insertions, substitutions, etc.) in response to drug therapy in the clinic and drug development in the laboratory. The bio chip and biosensors comprising polypeptides or antibodies of the present invention may also be used to simultaneously monitor the expression of a multiplicity of polypeptides, including those of the present invention. The polypeptides used to comprise a bio chip or biosensor of the present invention may be specified in the same manner as for the fragements, i.e, by their N-terminal and C-terminal positions or length in contigious amino acid residue. Methods and particular uses of the polypeptides and antibodies of the present invention to detect Candida species, including C albicans, or specific polypeptides using bio chip and biosensor technology include those known in the art, those of the U.S. Pat. Nos. and World Patent Nos. listed above for bio chips and biosensors using polynucleotides of the present invention, and those of: U.S. Pat. Nos. 5,658,732, 5,135,852, 5,567,301, 5,677,196, 5,690,894 and World Patent Nos. WO9729366, WO9612957, each incorporated herein in their entireties.

Treatment:

Agonists and Antagonists—Assays and Molecules

The present invention also provides a screening method for identifying compounds capable of enhancing or inhibiting (preferably inhibiting) a biological activity of the CaHK-1 polypeptide, which involves contacting a candidate compound with a CaHK-1 polypeptide in the presence of an phosphate acceptor polypeptide, assaying the activity of a CaHK-1 polypeptide in the presence of the candidate compound and acceptor polypeptide, and comparing the CaHK-1 activity to a standard level of activity, the standard being assayed when contact is made between a CaHK-1 polypeptide and the acceptor polypeptide in the absence of the candidate compound. Examples of screening assays well known in the art are described in Huang J. et al. 1992 J. Biol. Chem. 267(22):15511–15515. In this assay, an increase in CaHK-1 activity over the standard indicates that the candidate compound is an agonist of CaHK-1 activity and a decrease in CaHK-1 activity compared to the standard indicates that the compound is an antagonist of CaHK-1 activity. Other examples of methods that may be modified and used to test compounds that target CaHK-1 and inhibit the growth or virulence of C. albicans include those disclosed in U.S. Pat. No. 5,580,747, U.S. Pat. No. 5,747,276 WO 97/37230, and WO 95/06132.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity. Possible antagonists include, but are not limited to, isoflavones such as genistein. Other possible antagonists include the molecules disclosed in U.S. Pat. No. 5,643,950.

The antagonists may be employed for instance to inhibit histidine kinase activity. Antibodies against CaHK-1 may be employed to bind to and inhibit CaHK-1 activity to treat C. albicans. Possible methods of using antagonists include, but are not limited to, treating oral candidosis, including oral candidosis associated with HIV infection. The term treatment includes eliminating, reducing, controlling, and slowing the progress of oral candidosis. The term treatment comprises any clinically useful result either alone or in combinations with other drugs. Any of the above antagonists may be employed in a composition with a pharmaceutically acceptable carrier. The antagonists could be administered parenterally or by oral adminstration. Adminstration may include topical administration. Doses of antagonists would include those normally used by those skilled in the art for the route of adminstration and particular drug used. Doses can also be determined from extrapolating in vitro and in vivo assays in animal models. Extrapolations may be aided by data from similar drugs.

Vaccines

The present invention also provides vaccines comprising one or more polypeptides of the present invention. Heterogeneity in the composition of a vaccine may be provided by combining CaHK-1 polypeptides of the present invention. Multi-component vaccines of this type are desirable because they are likely to be more effective in eliciting protective immune responses against multiple species and strains of the Candida genus than single polypeptide vaccines. Thus, as discussed in detail below, a multi-component vaccine of the present invention may contain one or more, preferably 2 to about 20, more preferably 2 to about 15, and most preferably 3 to about 8, of the CaHK-1 polypeptides shown in FIGS. 1B and 4D (SEQ ID NO:2 and SEQ ID NO:4 respectively), or fragments thereof.

Multi-component vaccines are known in the art to elicit antibody production to numerous immunogenic components. Decker, M. and Edwards, K., *J. Infect. Dis.* 174:S270–275 (1996). In addition, a hepatitis B, diphtheria, tetanus, pertussis tetravalent vaccine has recently been demonstrated to elicit protective levels of antibodies in human infants against all four pathogenic agents. Aristegui, J. et a., *Vaccine* 15:7–9 (1997).

The present invention thus also includes multi-component vaccines. These vaccines comprise more than one polypeptide, immunogen or antigen. An example of such a multi-component vaccine would be a vaccine comprising more than one of the CaHK-1 polypeptides of the present invention or at least one of CaHK-1 polypeptides of the present invention in combination with other heterologous polypeptides of either Candidal or non-Candidal origin. Thus, a multi-component vaccine which confers protective immunity to both a Candidal infection and infection by another pathogenic agent is also within the scope of the invention.

Further within the scope of the invention are whole cell and whole viral vaccines. Such vaccines may be produced recombinantly and involve the expression of one or more of the CaHK-1 polypeptides shown in FIGS. 1B and 4A–C (SEQ ID NO:2 and SEQ ID NO:4 respectively). For example, the CaHK-1 polypeptides of the present invention may be either secreted or localized intracellular, on the cell surface, or in the periplasmic space. Further, when a recombinant virus is used, the CaHK-1 polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al., *Nature Biotech.* 15:653–657 (1997); Sirard, J. et al., *Infect. Immun.* 65:2029–2033 (1997); Chabalgoity, J. et al., *Infect. Immun.* 65:2402–2412 (1997). These cells may be administered live or may be killed prior to administration. Chabalgoity, J. et al., supra, for example, report the successful use in mice of a live attenuated Salmonella vaccine strain which expresses a portion of a platyhelminth fatty acid-binding protein as a fusion protein on its cells surface.

A multi-component vaccine can also be prepared using techniques known in the art by combining one or more CaHK-1 polypeptides of the present invention, or fragments thereof, with additional non-Candidal components (e.g., diphtheria toxin or tetanus toxin, and/or other compounds known to elicit an immune response). Such vaccines are useful for eliciting protective immune responses to both members of the Candida genus and non-Candidal pathogenic agents.

The vaccines of the present invention also include DNA vaccines. DNA vaccines are currently being developed for a number of infectious diseases. Boyer, J et al., *Nat. Med* 3:526–532 (1997); reviewed in Spier, R., *Vaccine* 14:1285–1288 (1996). Such DNA vaccines contain a nucleotide sequence encoding one or more CaHK-1 polypeptides of the present invention oriented in a manner that allows for expression of the subject polypeptide.

The present invention also relates to the administration of a vaccine which is co-administered with a molecule capable of modulating immune responses. Kim, J. et al., *Nature Biotech.* 15:641–646 (1997), for example, report the enhancement of immune responses produced by DNA immunizations when DNA sequences encoding molecules which stimulate the immune response are co-administered. In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to Candidal infection by either passive or active immunization. When the vaccines of the present invention are used to confer resistance to Candidal infection through active immunization, a vaccine of the present invention is administered to an animal to elicit a protective immune response which either prevents or attenuates a Candidal infection. When the vaccines of the present invention are used to confer resistance to Candidal infection through passive immunization, the vaccine is provided to a host animal (e.g., human, dog, or mouse), and the antisera elicited by this antisera is recovered and directly provided to a recipient suspected of having an infection caused by a member of the Candida genus.

The ability to label antibodies, or fragments of antibodies, with toxin molecules provides an additional method for treating Candidal infections when passive immunization is conducted. In this embodiment, antibodies, or fragments of antibodies, capable of recogniing the CaHK-1 polypeptides disclosed herein, or fragments thereof, as well as other Candida proteins, are labeled with toxin molecules prior to their administration to the patient. When such toxin derivatized antibodies bind to Candida cells, toxin moieties will be localized to these cells and will cause their death.

The present invention thus concerns and provides a means for preventing or attenuating a Candidal infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylatic" or "therapeutic" purpose. When provided prophylactically, the compound(s) are provided in advance of any symptoms of Candidal infection. The prophylactic administration of the compound (s) serves to prevent or attenuate any subsequent infection. When provided therapeutically, the compound(s) is provided upon or after the detection of symptoms which indicate that an animal may be infected with a member of the Candida genus. The therapeutic administration of the compound(s)

serves to attenuate any actual infection. Thus, the CaHK-1 polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., *Antibodies: A Laboratory Manual*, 2nd Ed; Cold Spring Harbor Laboratory Press, Cold Spring Harbor, New York (1988), the entire disclosure of which is incorporated by reference herein.

A composition is said to be "pharmacologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the CaHK-1 polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they non-specifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Coryne bacterium parvum*, or *Bordetella pertussis*, and members of the genus Brucella. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlH_4(SO_4)$. Examples of materials suitable for use in vaccine compositions are provided in *Remington's Pharmaceutical Sciences* (Osol, A, Ed, Mack Publishing Co, Easton, Pa., pp. 1324–1341 (1980), which reference is incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization of mice against *Bordetella pertussis* infection using vaccines encapsulated in biodegradable microsphere composed of poly(DL-lactide-co-glycolide) has been shown to stimulate protective immune responses. Shahin, R. et al., *Infect. Immun.* 63:1195–1200 (1995). Similarly, orally administered encapsulated *Salmonella typhimurium* antigens have also been shown to elicit protective immunity in mice. Allaoui-Attarki, K. et al., *Infect. Immun.* 65:853–857 (1997). Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

EXAMPLES

Strains And Growth Media

*Candida albicans* (strain SC5314) was grown in YEPD complex medium (1% yeast extract (Gibco-BRL), 2% peptone (Gibco-BRL) and 2% glucose), at 30° C. shaking at 250 rpm for 14 hours. Cells were harvested from liquid medium by centrifugation at 4000 x g for 10 minutes at 4° C. For RNA isolation, the same strain was grown in YNB for 3.5h at 30° C. [0.67% YNB (Gibco-BRL) and 2% glucose], inculated with $10^7$ cells/ml from an overnight culture in YNB.

E. coli strain LE392 was used for propagation of bacteriophage λEMBL3. All plasmid subcloning studies were performed in E. coli strain DH5α.

DNA Manipulations

Plasmid DNA was extracted from E. coli DH5α cells according to the manufacturer's instructions (Plasmid Midi Kit, Qiagen). Restriction enzymes and T4 DNA ligase were obtained from Gibco-BRL and used with buffers provided by the supplier under the recommended conditions. Agarose gel electrophoresis of DNA was performed according to standard protocols (Sambrook et al., *Molecular cloning: a Laboratory Manual*. 2nd Ed., Cold Spring Harbor Laboratory Press, Cold Spring Harbor, N.Y. (1989)). Construction of recombinant plasmids and selection of transformants were done by standard techniques (Sambrook et al., supra). Sequencing was carried out by the dideoxy chain termination method on an automatic sequencer (373A DNA sequencer, Applied Biosystems).

cDNA Library

The cDNA library was prepared from yeast-phase cells of C. albicans (ATCC strain 24433) grown at 37° C. on YPD agar plates for 14 hours. Cells were harvested in sterile water and total nucleic acid was prepared as described by Choi and Nuss, "A viral gene confers hypovirulence-associated traits to the chestnut blight fungus" EMBO J. 11, 473477 (1992)). RNA was isolated by precipitation with LiCl at 2M for 4 hours on ice followed by centrifugation at 10,000 x g for 10 minutes at 4° C. Poly-A$^+$ mRNA was purified using Oligotex-dT (Qiagen) and a cDNA library was constructed in the pSPORT1 vector using the SuperScript plasmid system for cDNA synthesis and plasmid cloning (Gibco-BRL). A 1.0 kb NotI-SalI partial cDNA with homology to the 3' end of the histidine kinase gene of the cyanobacterium Synechocystis was obtained by random sequencing. The fragment was digoxigenin-labelled by non-radioactive random priming (DIG DNA Labeling Kit, Boehringer Mannheim, Germany) and used as probe to isolate the full-length clone from a λEMBL3 C. albicans genomic library.

Southern Blot Experiments

Genomic DNA and total RNA from C. albicans were obtained according to the method described by Sherman et al. (1986). Four micrograms of DNA and 10 μg of RNA per lane were typically loaded for Southern and Northern, respectively. The DNA and RNA was transferred by capillarity to positively-charged nylon membranes (Amersham) by standard protocols (Sambrook et al., supra) and hybridized with the 1.0 kb NotI-SalI fragment described above (see section 2.3). The probe was labeled by non-radioactive random priming (DIG DNA Labeling Kit, Boehringer Mannheim) and detected according to the manufacturer's recommendation (DIG Nucleic Acid Detection Kit, Boehringer Mannheim).

Screening of the λEMBL3 Candida Albicans Genomic Library

λEMBL3 *Candida albicans* genomic library was screened by a standard protocol (Sambrook et al., supra), using the same probe that was used for Southern experiments. DNA samples were obtained from positive clones according to the manufacturer's instructions (Lambda Mini Kit, Qiagen). All DNAs were analyzed by BglII digestion and Southern blot hybridization as described above.

Reverse Transcription-Polymerase Chain Reaction (RT-PCR) Analysis

Removal of chromosal DNA contamination in total RNA was done by treatment of total RNA with Tnase-free DNAaseI (Amplification Grade, Gibco-BRL) for 15 min at room temperature in the buffer supplied with the enzyme. RT-PCR was carried out according to the protocols supplied with the reverse transcriptase (SuperScript II Rnase H-Reverse Transcriptase, Gibco-BRL) and the Taq DNA polymerase (Gibco-BRL), respectively. The primers used in the amplification were: p1 (5'-CCACTCATTAAGAAAACGCG-3') (SEQ ID NO:5), p2 (5'-CAGTATCTCTCACCTAACGTACAGACC-3') (SEQ ID NO:6), and p3 (5'-CGGTTTTTGTGTTAGAAATAGCC-3') (SEQ ID NO:7), at 50° C. as the annealing temperature for 35 cycles in a thermal cycler (HYBAID™, OmniGene).

Homology Searches. Sequence Analysis And Multiple Alignments

Homology searches were performed using the BLAST network service. The computer analysis of the completed sequence as well as the predicted protein sequence were performed using the GCG software package (University of Wisconsin).

Isolation of a Selected CaHK-1 DNA Clone From C. albicans

Three approaches, in addition to the one discussed above, may be used to isolate a C. albicans clone comprising a polynucleotide of the present invention from any C. albicans genomic DNA library. A wide varity of C. albicans strains, including C. albicans (ATCC strain 24433), can be used to obtain the polynucleotides and polypeptides of the present invention.

In the first method, a plasmid is directly isolated by screening a plasmid C. albicans genomic DNA library using a polynucleotide probe corresponding to a polynucleotide of the present invention. Particularly, a specific polynucleotide with 3040 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989). The transformants are plated on 1.5% agar plates (containing the appropriate selection 30 agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989) or other techniques known to those of skill in the art.

Alternatively, two primers of 15–25 nucleotides derived from the 5' and 3' ends of a polynucleotide of FIGS. 1A and 4A–C (SEQ ID NO: 1 and SEQ ID NO:3 respectively) are synthesized and used to amplify the desired DNA by PCR using a C. albicans genomic DNA prep as a template. PCR is carried out under routine conditions, for instance, in 25 μl of reaction mixture with 0.5 ug of the above DNA template. A convenient reaction mixture is 1.5–5 mM MgCl, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of FIGS. 1A and 4A–C (SEQ ID NO: 1 and SEQ ID NO:3 respectively) can be chemically synthesized and used to generate a nucleotide sequence of desired length using PCR methods known in the art.

Expression and Purification CaHK-1 polypeptides in E. coli

The bacterial expression vector pQE60 is used for bacterial expression of the polypeptide fragements of the present invention. (QIAGEN, Inc., 9259 Eton Avenue, Chatsworth, Calif., 9131 1). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6 X His tag") covalently linked to the carboxyl terminus of that polypeptide.

The DNA sequence encoding the desired portion of a CaHK-1 protein of the present invention is amplified from C. albicans genomic DNA using PCR oligonucleotide primers which anneal to the 5' and 3' sequences coding for the portions of the CaHK-1 polynucleotide shown in FIGS. 1A and 4A–C (SEQ ID NO: I and SEQ ID NO:3 respectively). Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desireda CaHK-1 polynucleotide sequence in FIGS. 1A and 4A–C (SEQ ID NO: 1 and SEQ ID NO:3 respectively). One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the polypeptide coding sequence of FIGS. 1A and 4A–C (SEQ ID NO: 1 and SEQ ID NO:3 respectively), excluding a stop codon, with the coding sequence aligned with the restriction site so as to maintain its reading frame with that of the six His codons in the pQE60 vector.

The amplified CaHK-1 DNA fragment and the vector pQE60 are digested with restriction enzymes which recognize the sites in the primers and the digested DNAs are then ligated together. The CaHK-1 DNA is inserted into the restricted pQE60 vector in a manner which places the CaHK-1 protein coding region downstream from the IPTG-inducible promoter and in-frame with an initiating AUG and the six histidine codons.

The ligation mixture is transformed into competent E. coli cells using standard procedures such as those described by Sambrook et al., supra.. E. coli strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing a CaHK-1 polypeptide, is available commercially (QIAGEN, Inc., supra). Transformants are identified by their ability to grow on LB agar plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the CaHK-1 polypeptide is loaded onto a nickel-nitrilo-tri-acetic acid ("Ni-NTA") affinity resin column (QIAGEN, Inc., supra). Proteins with a 6 x His tag bind to the Ni-NTA resin with high affinity are purified in a simple one-step procedure (for details see: The QIAexpressionist, 1995, QIAGEN, Inc., supra). Briefly the supernatant is loaded onto the column in 6M guanidine-HCl, pH 8, the column is first washed with 10 volumes of 6 M guanidine-HCl, pH 8, then washed with 10 volumes of 6 M guanidine-HCl pH 6, and finally the CaHK-1 polypeptide is eluted with 6M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein could be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The polypeptides of the present invention are also prepared using a non-denaturing protein purification method. For these polypeptides, the cell pellet from each liter of culture is resuspended in 25 mls of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm is approximately 10–20 O.D./ml. The suspension is then put through three freeze/thaw cycles from −70° C. (using a ethanol-dry ice bath) up to room temperature. The cells are lysed via sonication in short 10 sec bursts over 3 minutes at approximately 80W while kept on ice. The sonicated sample is then centrifuged at 15,000 RPM for 30 minutes at 4° C. The supernatant is passed through a column containing 1.0 ml of CL4B resin to pre-clear the sample of any proteins that may bind to agarose non-specifically, and the flow-through fraction is collected.

The pre-cleared flow-through is applied to a nickel-nitrilo-tri-acetic acid ("Ni-NTA") affinity resin column (Quiagen, Inc., supra). Proteins with a 6 X His tag bind to the Ni-NTA resin with high affinity and can be purified in a simple one-step procedure. Briefly, the supernatant is loaded onto the column in Lysis Buffer A at 4° C., the column is first washed with 10 volumes of Lysis Buffer A until the A280 of the eluate returns to the baseline. Then, the column is washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5). The protein is eluted off of the column with a series of increasing Imidazole solutions made by adjusting the ratios of Lysis Buffer A to Buffer B. Three different concentrations are used: 3 volumes of 75 mM midazole, 3 volumes of 150 mM Imidazole, 5 volumes of 500 mM Imidazole. The fractions containing the purified protein are analyzed using 8 %, 10 % or 14% SDS-PAGE depending on the protein size. The purified protein is then dialyzed 2X against phosphate-buffered saline (PBS) in order to place it into an easily workable buffer. The purified protein is stored at 4° C. or frozen at −80°.

The following alternative method may be used to purify a CaHK-1 polypeptide expressed in E coli when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5M NaCl, followed by centrifugation at 7000 x g for 15 min. The resultant pellet is washed again using 0.5M NaCl, 100 mM Tris, 50 mM EDTA, pH 7.4.

The resulting washed inclusion bodies are solubilized with 1.5M guanidine hydrochloride (GuHCl) for 2–4 hours. After 7000 x g centrifugation for 15 min., the pellet is discarded and the CaHK-1 polypeptide-containing supernatant is incubated at 4° C. overnight to allow further GuHCl extraction.

Following high speed centrifugation (30,000 x g) to remove insoluble particles, the GUHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded CaHK-1 polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the CaHK-1 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2M NaCl, 50 mM sodium acetate, pH 6.0 to 1.0M NaCl, 50 mM sodium acetate, pH 6.5. Fractions are collected under constant $A_{280}$ monitoring of the effluent. Fractions containing the CaHK-1 polypeptide (determined, for instance, by 16% SDS-PAGE) are then pooled.

The resultant CaHK-1 polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Alternative Expression and Purification CaHK-1 polypeptides in *E. coli*

The vector pQE10 is alternatively used in this example to clone and express the polypeptides of the present invention. The difference being such that an inserted DNA fragment encoding a polypeptide expresses that polypeptide with the six His residues (i.e., a "6 X His tag") covalently linked to the amino terminus of that polypeptide. The bacterial expression vector pQE10 (QIAGEN, Inc., 9259 Eton Avenue, Chatsworth, Calif., 91311) was used in this example. The components of the pQE 10 plasmid are arranged such that the inserted DNA sequence encoding a polypeptide of the present invention expresses the polypeptide with the six His residues (i.e., a "6 X His tag")) covalently linked to the amino terminus.

The DNA sequences encoding the desired portions of a polypeptide of FIGS. 1A and 4A–C (SEQ ID NO: 1 and SEQ ID NO:3 respectively) are amplified using PCR oligonucleotide primers from genomic *C. albicans* DNA. The PCR primers anneal to the nucleotide sequences encoding the desired amino acid sequence of a polypeptide of the present invention. Additional nucleotides containing restriction sites to facilitate cloning in the pQE10 vector are added to the 5' and 3' primer sequences, respectively.

For cloning a polypeptide of the present invention, the 5' and 3' primers are selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer is designed so the coding sequence of the 6 X His tag is aligned with the restriction site so as to maintain its reading frame with that of *C. albicans* polypeptide. The 3' is designed to include an stop codon. The amplified DNA fragment is then cloned, and the protein expressed, as described above for the pQE60 plasmid.

The DNA sequences of FIGS. 1A and 4A–C (SEQ ID NO: 1 and SEQ ID NO:3 respectively) encoding amino acid sequences may also be cloned and expressed as fusion proteins by a protocol similar to that described directly above, wherein the pET-32b(+) vector (Novagen, 601 Science Drive, Madison, Wis. 53711) is preferentially used in place of pQE10.

The above methods are not limited to the polypeptide fragements actually produced. The above method, like the methods below, can be used to produce either full length polypeptides or desired fragements thereof.

Alternative Expression and Purification of CaHK-1 polypeptides in *E. coli*

The bacterial expression vector pQE60 is used for bacterial expression in this example (QIAGEN, Inc., 9259 Eton Avenue, Chatsworth, Calif., 91311). However, in this example, the polypeptide coding sequence is inserted such that translation of the six His codons is prevented and, therefore, the polypeptide is produced with no 6 X His tag.

The DNA sequence encoding the desired portion of the CaHK-1 amino acid sequence is amplified from a *C. albicans* genomic DNA prep the deposited DNA clones using PCR oligonucleotide primers which anneal to the 5' and 3' nucleotide sequences corresponding to the desired portion of the CaHK-1 polypeptides. Additional nucleotides containing restriction sites to facilitate cloning in the pQE60 vector are added to the 5' and 3' primer sequences.

For cloning CaHK-1 polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified CaHK-1 polynucleotide and the vector pQE60 are digested with restriction enzymes recognizing the sites in the primers and the digested DNAs are then ligated together. Insertion of the CaHK-1 polynucleotide into the restricted pQE60 vector places the CaHK-1 polypeptide coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described by Sambrook et al. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing CaHK-1 polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the CaHK-1 polypeptide, the cells are then stirred for 3–4 hours at 4° C. in 6M guanidine-HCl, pH 8. The cell debris is removed by centrifugation, and the supernatant containing the CaHK-1 polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure CaHK-1 polypeptide. The purified protein is stored at 4° C. or frozen at −80° C.

The following alternative method may be used to purify CaHK-1 polypeptides expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5M NaCl, followed by centrifugation at 7000 x g for 15 min. The resultant pellet is washed again using 0.5M NaCl, 100 mM Tris, 50 mM EDTA, pH 7.4.

The resulting washed inclusion bodies are solubilized with 1.5M guanidine hydrochloride (GuHCl) for 2–4 hours. After 7000 x g centrifugation for 15 min., the pellet is discarded and the CaHK-1 polypeptide-containing supernatant is incubated at 4° C. overnight to allow further GuHCl extraction.

Following high speed centrifugation (30,000 x g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded CaHK-1 polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the CaHK-1 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 MM NaCl. The CM-20 column is then eluted using a 10 column volume linear gradient ranging from 0.2M NaCl, 50 mM sodium acetate, pH 6.0 to 1.0M NaCl, 50 mM sodium acetate, pH 6.5. Fractions are collected under constant $A_{280}$ monitoring of the effluent. Fractions containing the CaHK-1 polypeptide (determined, for instance, by 16% SDS-PAGE) are then pooled.

The resultant CaHK-1 polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Cloning and Expression of CaHK-1 polypeptides in Other Bacteria

CaHK-1 polypeptides can also be produced in: *Enterococcus faecalis* using the methods of S. Skinner et al., (1988) Mol. Microbiol. 2:289–297 or J. I. Moreno (1996) Protein Expr. Purif. 8(3):332–340; Lactobacillus using the methods of C. Rush et al., 1997 Appl. Microbiol. Biotechnol. 47(5) :537–542; or in *Bacillus subtilis* using the methods Chang et al., U.S. Pat. No. 4,952,508.

Cloning and Expression of CaHK-1 polypeptides in COS Cells

A CaHK-1 expression plasmid is made by cloning a portion of the DNA encoding a CaHK-1 polypeptide into the expression vector pDNAI/Amp or pDNAIII (which can be obtained from Invitrogen, Inc.). The expression vector pDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a CaHK-1 polypeptide is cloned into the polylinker region of the vector so that recombinant protein expression is directed by the CMV promoter. The plasmid construction strategy is as follows. The DNA from a *C. albicans* genomic DNA prep is amplified using primers that contain convenient restriction sites, much as described above for construction of vectors for expression of CaHK-1 in *E. coli*. The 5' primer contains a Kozak sequence, an AUG start codon, and nucleotides of the 5' coding region of the CaHK-1 polypeptide. The 3' primer, contains nucleotides complementary to the 3' coding sequence of the CaHK-1 DNA, a stop codon, and a convenient restriction site.

The PCR amplified DNA fragment and the vector, pDNAI/Amp, are digested with appropriate restriction enzymes and then ligated. The ligation mixture is transformed into an appropriate *E. coli* strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the CaHK-1 polypeptide For expression of a recombinant CaHK-1 polypeptide, COS cells are transfected with an expression vector, as described above, using DEAE-dextran, as described, for instance, by Sambrook et al. (supra). Cells are incubated under conditions for expression of CaHK-1 by the vector.

Expression of the CaHK-1 HA fusion protein is detected by radiolabeling and immunoprecipitation, using methods described in, for example Harlow et al., supra. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Cloning and Expression of CaHK-1 in CHO Cells

The vector pC4 is used for the expression of CaHK-1 polypeptides in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3'intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the CaHK-1 polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the CaHK-1 polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the CaHK-1 polypeptide is synthesized and used. A 3' primer, containing a restriction site, stop codon, and nucleotides complementary to the 3' coding sequence of the CaHK-1 polypeptides is synthesized and used. The amplified fragment is digested with the restriction endonucleases and then purified again on a I% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using a lipid-mediated transfection agent such as Lipofectin™ or LipofectAMINE.™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μm, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

CaHK-1-Deletion Experiments

The standard "urablaster" approach was used to construct gene deleted strains in CaHK-1. Strain CAI4 (ura3−) was transformed with linearized CaHK-1 which had been deleted of an in 5.4 kb HindIII/BamH1 fragment and replaced with the hisGURA3hisG insert from pMB7 containing URA3. The deleted portion of CaHK-1 included the key histidine residue (His$^{2007}$ of SEQ ID NO:4) of the sensor domain as well as regions both N- and C terminal of the sensor domain. Ura+transformants were analyzed for integration by Southern hybridization. Subsequently, one of the Ura+ transformants was then plated on YNB containing 1 mg/ml 5-FOA to select for spontaneous Ura- derivatives. FOA is toxic for strains containing the URA3 gene; therefore, only those cells which have lost the URA3 by intrachromosomal or interchromosomal recombination will grow on YNB-FOA. The loss of the URA3hisG portion of the disruption casette was confirmed by Southern hybridization; the transformation protocol was then repeated using the ura3− segregant (hisG), heterozygous for CaHK-1 in order to disrupt the second allele and thereby provide a strain with the desired null phenotype. The in vitro phenotype of the CaHK-1 null was studied. Null cells displayed a flocculation phenotype in several liquid media at pH 7.5 but not at pH 3.5 (30° C.). This phenotype suggests that a change in the cell surface of the organism (hence, flocculation) is associated with a mutation in this putative signal gene.

Animal Studies of CaHK-1 Mutants

Upregulation of CaHK-1 in oral candidiasis. Quantitative RT-PCR was used in order to measure transcription of CaHK-1 during infection. For these experiments, a rat model of oropharyngeal candidiasis was established in pathogen-free rats. Hyposalivation of the animals was achieved by ligation of the parotid ducts and the removal of the submandibular and sublingual salivary glands. This procedure allows the organism to colonize the oral cavity. Rats were infected using a cotton-tipped applicator saturated with an actively growing culture (yeasts) of *C albicans*. At 72 h post-infection, infected animals were sacrificed, and the oral cavity was swabbed to remove adherent organisms. Cells were suspended in PBS for quantitation of organisms and RNA extraction. For comparison to in vitro grown organisms, strain SC53 14 was grown in Lee's medium at 37° C. to induce hyphae formation as occurred in vivo. Prior to RNA extraction, in vitro and in vivo samples were resuspended in cold RSB lysis buffer to lyse rat epithelial cells. Following centrifugation, the cell samples were resuspended in cold Tris-HCI (pH 7..5), containing 100 mM LiCl and 10 mM DTT. An equal volume of buffer-saturated phenol and glass beads was added, and the mixture was vortexed to break *C. albicans* cells. Samples were reextracted 2x with phenol/CHCl$_3$ and 1x with CHCl$_3$. Each RNA preparation was precipitated with ehtanol and stored. RT-PCR reactions included RNA isolated from independent samples obtained from at least two animals and RNA from cultures prepared in vitro. For all reactions, an additional control was also included in which the reverse transcriptase was omitted. Twenty-one-mer primers were designed from the sequence of the CaHK-1 which amplified a 300 bp fragment corresponding to positions 4157–4467 (SEQ ID NO: 1). RT was done using Superscript H (Gibro-BRL) under conditions recommended by the manufacturer. cDNAs were then amplified by PCR using AmpliTaq (Perkin-Elmer) with [α$^{33}$ P] dATP used as the radiolabel. The parameters for PCR were: denaturation for 5 min at 95° C.; denaturation for 45 sec at 95° C.; annealing for 45 sec at 68° C.; exyrndiond for 1 min at 72° C. (l5cyles). PCR products were resolved by electrophoresis in 6% polyacrylamide gel and visualized by autoradiography. A 4.5-fold increase in expression of CaHK-1 was determined by densitometer tracings. It was observed that transcription of CaHK-1 is upregulated during oral candidiasis. The data show that CaHK-1 is upregulated in oral disease and, therefore, suggestive that CaHK-1 is required for the successful infection of the oral cavity by the organism.

Animal Studies on the Virulence of the CaHK-1/CaHK-1 Null

The CaHK-1 null strain, described above, was furthure evaluated in a systemic murine model of candidiasis. Mice were infected intravenously with 1.5×10$^6$ yeast cells of CAF2-1 (CaHK-1/CaHK-1), CAF11 (CaHK-1/CaHK-1) or CAF21 (CaHK-1/CaHK-1). Groups of 5 mice were euthanised at 24, 48 and 72 h post-infection and tissue loads determined for CAF2-1 and CAF21. Additionally, revival of mice infected with each of the three strains was also measured daily for 21 days. Our data indicate that within 24 hrs, all mice infected with wt cells (CAF2-1) died. In comparison, all mice survived infection with CAF21 (CaHK-1 /CaHK-1) while 1/7 mice died when infected with CAF11 (CaHK-1/CaHK-1). Correspondingly, kidney levels of mice infected with the null strain reached a maximum at 24–48 hr and then decreased 2 logs by 72 hr. Actually, mice infected with the null strain have survived over a 14 day period, while 2/8 heterozygotes have died during this 21 day period. These data are highly suggestive that CaHK-1 is essential for infection. Our observation does not necessarily mean that CaHK-1 is a virulence factor. More likely, the gene provides some essential functions via a signal transduction mechanism which results in the transcription of virulence/growth genes.

The disclosure of all publications (including patents, patent applications, journal articles, laboratory manuals, books, or other documents) cited herein and the sequence listings are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparent to those skilled in the art from the foregoing description and accompanying drawings. Such modifications are intended to fall within the scope of the appended claims.

What is claimed is:

1. An isolated nucleic acid fragment comprising a polynucleotide having a nucleotide sequence selected from the group consisting of:
   (a) a nucleotide sequence encoding a CaHK-1 polypeptide having the amino acid sequence at positions 1 to 971 in SEQ ID NO:2;
   (b) a nucleotide sequence encoding a CaHK-1 polypeptide having the amino acid sequence at positions 1 to 2471 in SEQ ID NO:4;
   (c) a nucleotide sequence encoding a CaHK-1 polypeptide having the amino acid sequence at positions 2 to 971 in SEQ ID NO:2;
   (d) a nucleotide sequence encoding a CaHK-1 polypeptide having the amino acid sequence at positions 2 to 2471 in SEQ ID NO:4;
   (e) a nucleotide sequence encoding a CaHK-1 polypeptide having the amino acid sequence at positions 482 to 721 in SEQ ID NO:2;
   (f) a nucleotide sequence encoding a CaHK-1 polypeptide having the amino acid sequence at positions 834 to 971 in SEQ ID NO:2;
   (g) a nucleotide sequence encoding a CaHK-1 polypeptide having the amino acid sequence at positions 482 to 971 in SEQ ID NO:2;
   (h) a nucleotide sequence encoding a CaHK-1 polypeptide having the amino acid sequence encoded by the *Candida albicans* CaHK-1 cDNA contained in ATCC Deposit No. 209504 and ATCC Deposit No. 209505 wherein said cDNA in ATCC Deposit No. 209504 and ATCC Deposit No. 209505 together comprise a sequence encoding the full length CaHK-1 polypeptide; and
   (i) a nucleotide sequence fully complementary to any of the nucleotide sequences in (a), (b), (c), (d), (e), (f), (g), or (h) above.

2. An isolated nucleic acid fragment comprising a polynucleotide which hybridizes under stringent hybridization conditions to the nucleotide sequence of SEQ ID NO:3, wherein said polynucleotide does not hybridize under stringent hybridization conditions to a polynucleotide having a nucleotide sequence consisting of only A residues or of only T residues.

3. An isolated nucleic acid fragment comprising a polynucleotide which comprises at least 27 contiguous nucleotides of SEQ ID NO:1 or SEQ ID NO:3, wherein said polynucleotide encodes an amino acid sequence of an epitope-bearing portion of a CaHK-1 polypeptide, and wherein said amino acid sequence is at least 9 residues in length.

4. An isolated nucleic acid fragment comprising a polynucleotide having at least 50 contiguous nucleotides from nucleotide positions 750 to 3,000 of SEQ ID NO:3.

5. A method of detecting the presence of a *Candida albicans* Histidine Kinase-1 (CaHK-1) polynucleotide in a biological sample comprising:
   (a) contacting the sample with a probe that specifically hybridizes to the nucleotide sequence of SEQ ID NO:3 under conditions which allow the hybridizing of the probe and the polynucleotide; and
   (b) detecting hybridization of the probe and the polynucleotide as indicative of the presence of a CaHK-1 polynucleotide.

6. A method for making a recombinant vector comprising: inserting the isolated nucleic acid fragment of claim 1 into a vector; and isolating said recombinant vector.

7. A recombinant vector produced by the method of claim 6.

8. A method of making a recombinant host cell comprising:

introducing the recombinant vector of claim 7 into a host cell: and isolating said host cell.

9. A recombinant host cell produced by the method of claim 8.

10. A method for producing a CaHK-1 polypeptide comprising:

culturing a host cell of claim 9 under conditions such that said polypeptide is expressed; and recovering said polypeptide.

11. The isolated nucleic acid fragment of claim 1, wherein said polynucleotide is (a).

12. The isolated nucleic acid fragment of claim 1, wherein said polynucleotide is (b).

13. The isolated nucleic acid fragment of claim 1, wherein said polynucleotide is (c).

14. The isolated nucleic acid fragment of claim 1, wherein said polynucleotide is (d).

15. The isolated nucleic acid fragment of claim 1, wherein said polynucleotide is (e).

16. The isolated nucleic acid fragment of claim 1, wherein said polynucleotide is (f).

17. The isolated nucleic acid fragment of claim 1, wherein said polynucleotide is (g).

18. The isolated nucleic acid fragment of claim 1, wherein said polynucleotide is (h).

19. A method of detecting the presence of a *Candida albicans* Histidine Kinase-1 (CaHK-1) polynucleotide in a biological sample comprising:

(a) contacting the sample with a primer that specifically hybridizes to the nucleotide sequence of SEQ ID NO:3 under conditions which allow for hybridization of the primer and the polynucleotide;

(b) amplifying the polynucleotide by PCR using the primer; and (c) detecting amplification products of step (b) as indicative of the presence of a CaHK-1 polynucleotide.

20. The method of claim 5 or 19 wherein a device selected from the group consisting of:

(a) a bio chip;

(b) a biosensor;

(c) a nylon membrane; and (d) a thermocycler is used in the method.

* * * * *

SEQUENCE LISTING

```
<160> NUMBER OF SEQ ID NOS: 9

<210> SEQ ID NO 1
<211> LENGTH: 3119
<212> TYPE: DNA
<213> ORGANISM: Homo sapiens

<400> SEQUENCE: 1
catatgttca gtctatttat gaatattatt tcagttgtca tgctgtattt tttgaatcaa      60
ttgaaaaaat gctggatctt atacatccag gtaacgctag ttcccattgc acaagactgt     120
cttattattc atcttttcat ttgatagtta atgtttccaa gattttcttt tcatgtatga     180
atggagaaag tttcaaaatg ttctcaacat ttcaagtgta aatcctattt aacagaggat     240
ccccaaatgc ctgaaatgga caattttttta tacgatagtg aaatgttact tgctggacat     300
tcagaattga atgaatttat gagaaaatat cagtcattca accaaacttc cgttggtaaa     360
ttttgctact atttaattgt actacttgta atgtcacgtg aacacagatt tgacgaggct     420
gccgatttgg tttttgaaagt tttggaagac ttactggaaa aattgcctgt atctttttttg     480 catcatcaat attacttaat atgtggtaaa gtgtttgctt atcaccagac caaaacccca     540
gaaagtgagg aacaagtgga acgtatttttg gctcgtcaat ttgaaagata tgaattgtgg     600
gcactgacga ataagccgac ccttctacca cggtacttgt tgttgagtac ctacaaacag     660
attagagaaa accatgttga caagttagaa atactagatt catttgagga ggcgttacag     720
acggcccata aatttcataa tgtatatgat atgtgctgga tcaatttgga atgtgcaaga     780
tggttaatta gcataaacca aaaaaggcac agaatctcaa gaatggttaa acaaggtctt     840
aaaattttga gaagcttgga attaaataat catttaagat tagctgaatt tgaatttgat     900
gaatacattg aggacgaaga tcacagaaat aaatgggcag ggttaactaa taatccaaca     960
ttggatactg ttactacctg gcaacaacag aacatgcccg ataaggtatc tccatgcaat    1020
gacaagcagt tggtccacgg aaaacaattt ggcaaaaaag agtttgatag ccatttgctc    1080
agattgcact ttgatggcca atatacaggc ctagatttga attcagctat tcgtgaatgt    1140
ctagcaatat ccgaagcttt agacgaaaat tccattctca caagttgat ggcatctgcc    1200 atcaagtatt caggtgccac atatgggta attgtcacga agaaaaacca ggagacacct    1260
tttcttagaa caattggctc gcagcacaat attcacacat taaacaacat gccaatttcc    1320
gacgacattt gtcctgctca gttgattcgt catgtattgc atacaggaga aacggtgaac    1380
aaagctcatg atcacatagg atttgctaac aagtttgaga atgaatactt tcaaacaaca    1440
```

-continued

```
gataaaaagt attcagttgt gtgtttgcca ttaaagagtc tgcttggatt atttggtgca   1500
ctttatctag aaggtagtga tggtgatttt ggacatgaag atttgttcaa tgaaaggaaa   1560
tgtgatttgt tacaactttt ttgcacacaa gcagctgtgg ctttgggtaa ggagcgtttg   1620
cttttgcaaa tggaactagc aaaaatggca gcagaagacg ccactgatga aaaagccagt   1680
tttttggcaa acatgtcaca tgaaatacga accccattca attcgttatt gtcatttgct   1740 attttttttgt tagataccaa attggattct actcaaagag aatatgtcga ggcaattcag   1800
agctccgcaa tgataacgtt gaatattatt gatgggatac ttgcgttttc caaaattgag   1860
catggatcct ttacattaga aaatgccccc ttttctttga atgattgtat cgagactgct   1920
attcaagtaa gtggggaaac aattttgaat gaccagattg agttggtgtt ttgtaacaat   1980
tgtccagaga ttgaatttgt ggttggtgat ctaacgaggt tcagacaaat tgtgatcaat   2040
ttggtgggta atgctattaa gtttacaacc aaaggtcatg ttttgatttc ttgtgatagc   2100
cgaaaaatta cggacgacag atttgagatc aatgtgtcag ttgaggattc aggaattgga   2160
atttccaaaa aatctcaaaa taaagtgttt ggagcatttt ctcaagtaga tggttccgca   2220
agacgagaat atggtggctc tggattaggt ttagctatat caaagaaatt gactgaacta   2280
atgggtggca caattagatt tgaaagtgag gaagggattg gcacaacgtt ttatgttagc   2340
gtcattatgg acgcaaaaga atactcatcc ccgccattta gtttaaataa aaaatgtttg   2400
atttacagcc agcattgtct tactgccaag tcaatttcaa atatgcttaa ttattttgga   2460
tcaacagtta aagtcactaa tcagaagtct gagttttcaa cttccgtgca agccaacgac   2520 atcattttttg ttgatcgcgg aatggaacct gatgttagtt gcaaaaccaa aatcattccc   2580
atcgacccaa aacctttcaa aagaaacaaa ctcattagta ttctcaaaga acaaccaagt   2640
ttgcccacca aagtgtttgg aaacaacaaa tctaatttat caaaacaata ccctctaaga   2700
atattattag cagaagacaa tcttttgaac tataaagtat gtttgaagca tttggataaa   2760
ttggggtaca aggcagatca tgccaaagat ggagtagtag ttttggataa atgtaaagaa   2820
ctactagaaa aagacgaaaa atatgatgtc atattgatgg atattcaaat gcctcgtaag   2880
gacggtatta cagctacaag ggatttgaaa acattgtttc acacacaaaa aaaggaaagt   2940
tggttacccg tgatcgtagc attgacagct aatgttgctg gagacgacaa aaagaggtgt   3000
ctagaagagg gaatgtttga ttttataacc aaacccattt taccagatga acttagacgt   3060
attttaacaa aagtagggga aacagtgaat atgtaaaatg tgtatttaat aataagatc   3119
```

<210> SEQ ID NO 2
<211> LENGTH: 971
<212> TYPE: PRT
<213> ORGANISM: Homo sapiens

<400> SEQUENCE: 2

```
Met Glu Lys Val Ser Lys Cys Ser Gln His Phe Lys Cys Lys Ser Tyr
 1               5                  10                  15

Leu Thr Gly Asp Pro Gln Met Pro Glu Met Asp Asn Phe Leu Tyr Asp
            20                  25                  30

Ser Glu Met Leu Leu Ala Gly His Ser Glu Leu Asn Glu Phe Met Arg
        35                  40                  45

Lys Tyr Gln Ser Phe Asn Gln Thr Ser Val Gly Lys Phe Cys Tyr Tyr
    50                  55                  60

Leu Ile Val Leu Leu Val Met Ser Arg Glu His Arg Phe Asp Glu Ala
65                  70                  75                  80
```

-continued

Ala Asp Leu Val Leu Lys Val Leu Glu Asp Leu Leu Glu Lys Leu Pro
                85                  90                  95

Val Ser Phe Leu His His Gln Tyr Tyr Leu Ile Cys Gly Lys Val Phe
            100                 105                 110

Ala Tyr His Gln Thr Lys Thr Pro Glu Ser Glu Gln Val Glu Arg
            115                 120                 125

Ile Leu Ala Arg Gln Phe Glu Arg Tyr Glu Leu Trp Ala Leu Thr Asn
    130                 135                 140

Lys Pro Thr Leu Leu Pro Arg Tyr Leu Leu Ser Thr Tyr Lys Gln
145                 150                 155                 160

Ile Arg Glu Asn His Val Asp Lys Leu Glu Ile Leu Asp Ser Phe Glu
                165                 170                 175

Glu Ala Leu Gln Thr Ala His Lys Phe His Asn Val Tyr Asp Met Cys
            180                 185                 190

Trp Ile Asn Leu Glu Cys Ala Arg Trp Leu Ile Ser Ile Asn Gln Lys
        195                 200                 205

Arg His Arg Ile Ser Arg Met Val Lys Gln Gly Leu Lys Ile Leu Arg
    210                 215                 220

Ser Leu Glu Leu Asn Asn His Leu Arg Leu Ala Glu Phe Glu Phe Asp
225                 230                 235                 240

Glu Tyr Ile Glu Asp Glu Asp His Arg Asn Lys Trp Ala Gly Leu Thr
                245                 250                 255

Asn Asn Pro Thr Leu Asp Thr Val Thr Thr Trp Gln Gln Asn Met
            260                 265                 270

Pro Asp Lys Val Ser Pro Cys Asn Asp Lys Gln Leu Val His Gly Lys
        275                 280                 285

Gln Phe Gly Lys Lys Glu Phe Asp Ser His Leu Leu Arg Leu His Phe
    290                 295                 300

Asp Gly Gln Tyr Thr Gly Leu Asp Leu Asn Ser Ala Ile Arg Glu Cys
305                 310                 315                 320

Leu Ala Ile Ser Glu Ala Leu Asp Glu Asn Ser Ile Leu Thr Lys Leu
                325                 330                 335

Met Ala Ser Ala Ile Lys Tyr Ser Gly Ala Thr Tyr Gly Val Ile Val
            340                 345                 350

Thr Lys Lys Asn Gln Glu Thr Pro Phe Leu Arg Thr Ile Gly Ser Gln
        355                 360                 365

His Asn Ile His Thr Leu Asn Asn Met Pro Ile Ser Asp Asp Ile Cys
    370                 375                 380

Pro Ala Gln Leu Ile Arg His Val Leu His Thr Gly Glu Thr Val Asn
385                 390                 395                 400

Lys Ala His Asp His Ile Gly Phe Ala Asn Lys Phe Glu Asn Glu Tyr
                405                 410                 415

Phe Gln Thr Thr Asp Lys Lys Tyr Ser Val Val Cys Leu Pro Leu Lys
            420                 425                 430

Ser Leu Leu Gly Leu Phe Gly Ala Leu Tyr Leu Glu Gly Ser Asp Gly
        435                 440                 445

Asp Phe Gly His Glu Asp Leu Phe Asn Glu Arg Lys Cys Asp Leu Leu
    450                 455                 460

Gln Leu Phe Cys Thr Gln Ala Ala Val Ala Leu Gly Lys Glu Arg Leu
465                 470                 475                 480

Leu Leu Gln Met Glu Leu Ala Lys Met Ala Ala Glu Asp Ala Thr Asp
                485                 490                 495

-continued

```
Glu Lys Ala Ser Phe Leu Ala Asn Met Ser His Glu Ile Arg Thr Pro
            500                 505                 510
Phe Asn Ser Leu Leu Ser Phe Ala Ile Phe Leu Leu Asp Thr Lys Leu
            515                 520                 525
Asp Ser Thr Gln Arg Glu Tyr Val Glu Ala Ile Gln Ser Ser Ala Met
            530                 535                 540
Ile Thr Leu Asn Ile Ile Asp Gly Ile Leu Ala Phe Ser Lys Ile Glu
545                 550                 555                 560
His Gly Ser Phe Thr Leu Glu Asn Ala Pro Phe Ser Leu Asn Asp Cys
                565                 570                 575
Ile Glu Thr Ala Ile Gln Val Ser Gly Glu Thr Ile Leu Asn Asp Gln
            580                 585                 590
Ile Glu Leu Val Phe Cys Asn Asn Cys Pro Glu Ile Glu Phe Val Val
            595                 600                 605
Gly Asp Leu Thr Arg Phe Arg Gln Ile Val Ile Asn Leu Val Gly Asn
610                 615                 620
Ala Ile Lys Phe Thr Thr Lys Gly His Val Leu Ile Ser Cys Asp Ser
625                 630                 635                 640
Arg Lys Ile Thr Asp Asp Arg Phe Glu Ile Asn Val Ser Val Glu Asp
                645                 650                 655
Ser Gly Ile Gly Ile Ser Lys Lys Ser Gln Asn Lys Val Phe Gly Ala
                660                 665                 670
Phe Ser Gln Val Asp Gly Ser Ala Arg Arg Glu Tyr Gly Gly Ser Gly
            675                 680                 685
Leu Gly Leu Ala Ile Ser Lys Lys Leu Thr Glu Leu Met Gly Gly Thr
            690                 695                 700
Ile Arg Phe Glu Ser Glu Glu Gly Ile Gly Thr Thr Phe Tyr Val Ser
705                 710                 715                 720
Val Ile Met Asp Ala Lys Glu Tyr Ser Ser Pro Pro Phe Ser Leu Asn
                725                 730                 735
Lys Lys Cys Leu Ile Tyr Ser Gln His Cys Leu Thr Ala Lys Ser Ile
                740                 745                 750
Ser Asn Met Leu Asn Tyr Phe Gly Ser Thr Val Lys Val Thr Asn Gln
            755                 760                 765
Lys Ser Glu Phe Ser Thr Ser Val Gln Ala Asn Asp Ile Ile Phe Val
            770                 775                 780
Asp Arg Gly Met Glu Pro Asp Val Ser Cys Lys Thr Lys Ile Ile Pro
785                 790                 795                 800
Ile Asp Pro Lys Pro Phe Lys Arg Asn Lys Leu Ile Ser Ile Leu Lys
                805                 810                 815
Glu Gln Pro Ser Leu Pro Thr Lys Val Phe Gly Asn Asn Lys Ser Asn
                820                 825                 830
Leu Ser Lys Gln Tyr Pro Leu Arg Ile Leu Leu Ala Glu Asp Asn Leu
            835                 840                 845
Leu Asn Tyr Lys Val Cys Leu Lys His Leu Asp Lys Leu Gly Tyr Lys
            850                 855                 860
Ala Asp His Ala Lys Asp Gly Val Val Val Leu Asp Lys Cys Lys Glu
865                 870                 875                 880
Leu Leu Glu Lys Asp Glu Lys Tyr Asp Val Ile Leu Met Asp Ile Gln
                885                 890                 895
Met Pro Arg Lys Asp Gly Ile Thr Ala Thr Arg Asp Leu Lys Thr Leu
            900                 905                 910
Phe His Thr Gln Lys Lys Glu Ser Trp Leu Pro Val Ile Val Ala Leu
```

-continued

```
                915                 920                 925
    Thr Ala Asn Val Ala Gly Asp Asp Lys Lys Arg Cys Leu Glu Glu Gly
                930                 935                 940

Met Phe Asp Phe Ile Thr Lys Pro Ile Leu Pro Asp Glu Leu Arg Arg
    945                 950                 955                 960

Ile Leu Thr Lys Val Gly Glu Thr Val Asn Met
                    965                 970

<210> SEQ ID NO 3
<211> LENGTH: 8561
<212> TYPE: DNA
<213> ORGANISM: Homo sapiens

<400> SEQUENCE: 3
agatctatat tgattatgat agcaaattac agttcctgat aactcgtagg ttttttttaaa      60 agtagtagag tatcgccgag tgaaagttgt caggaaaaat attggacaat gataaccaa      120 tattcagtgt cgtgcatttt tgtcattaac tcagcaatat actaaaaaac tctatatttt      180
ttgcaacttg atcccccctcg aacataagca agaccacgac aatagcataa ttcaaataga    240
aagaagacta gttactggga tatgcaataa atttaagtac taaatagtgg caaaagtaca     300
gaattagaag aaaaatatgt aaagacttag tatttgtaaa cacaattgcg agaaatcact    360
attaatatgt tcagaaatgg cagtatcaaa aaagtgccga cttcaaacaa ccccaagttc    420
aatcatcaat gtgtaactaa catattcgtc ttcttttgaa actgtgttta agaagtcttt    480
gtggtattac taatccaacc aaaacagaga atccagcctc ttagtaatca agccaaaaag    540
caaccaaggc ggcaaaaaaa aaactcgctt tctaaggcgg gccacactaa atagattgct    600
catagattgt ttttttttttt gaccttccca aaattgataa ttagcaccaa atatttagtc    660
acataaatct tgaatgacaa gatatgaaac tgttgcctaa tcgttaagaa catggagaag    720
taaaatattg agaattattc gactatattg aagatgttgt ttggactgaa ttataacttc    780
tagacaattt tttttattaa gggtatcgga aattacccac aaaatgcaaa caccaaaaaa    840
gaacaaaatt aacaatacat acaataaaat gcgtggaaaa taaaaaaacg gttttttgtgt    900 tagaaatagc catcgataaa ccttcatgaa ttatcattag tgaaaagca accgtaaaaa     960 ttaatttaaa actttttttt taaaagaaaa actccaaagc tttcttctt tttctttaa     1020 taggattcga ctaatagcct tttcttactt attttggtgc tacagtatct ctcacctaac    1080
gtacagacct tttacagaat agtttttcag taaatcatgt ctatgaactt ttttaattca    1140
agcgaacctg caagggacca caaaccggac caggaaaagg aaacagtaat gacgacagaa    1200
cattatgaat ttgaacgacc agatgtcaaa gctatacgaa atttcaaatt cttcaggctg    1260
gacgaaacag aaaccaaaaa aggaccaaac cttcatatttt cggatctatc ccctcttgaa    1320
tcacaatctg tgccccttc agccttaagt ttaaatcatt cgataatacc agaccaatat    1380
gaacgacgtc aggatacacc ggatcctata cactcctg aaatttcatt aagtgattat      1440
ttatatgatc agacattgag tccccaaggt tttgacaata gccgtgaaaa tttcaacatc    1500
cacaaaacaa tcgccagttt attcgaagat aactcatctg ttgtatcaca agaatctact    1560
gatgacacca agcaacatt atcactggaa acatgtgata gcttttcatt gaataacgca    1620
tcatatttga ccaacattaa ctttgtgcaa aatcatttac aatacctag tcaaaatgtt    1680 ttgggaaatc gcacttccaa cagcttaccg ccatcatcat catcacagat agactttgat    1740
gcctccaatt tgacacccga ttcgatacca gggtacattc tcaacaagaa acttggctct    1800
```

-continued

```
gttcatcaac tgacagacct ggtatacaac gctatcaaga ttcctcaaaa cgaagaatac    1860
aactgttgca ctaaagcttc tgctagtcaa aatccaacaa atttgaattc taaagtgata    1920
gtgaggctat cacctaatat ttttcaaaac ttgtcacttt cgcgttttct taatgagtgg    1980
tacatattat ctgggaagca cagttcaaaa gagcaccaaa tatggtccaa tgagtctctc    2040
acaaatgaat acgtacaaga caaaacaatt ccgacatttg ataaagaaag tgcacgtttt    2100
agaccaacgt tgcccataaa tataccaggt atcttgtacc cgcaagagat aataaacttt    2160
tgtgtgaaca gccatgatta tccacttgaa cacccatcac agtccactga tcaaaaaaga    2220
tttgccatgg tgtaccaaga caacgattac aagacattca aagaactcag catgttcact    2280
ttgcacgagc tacaaactag acaggggtcg tattcgtcca acgagtcacg acgaaaatcc    2340
agcagtggct ttaatatagg tgtcaatgca accaccactg aagctgggtc tttggaatct    2400
tttagtaatc taatgcagaa tcaccatctt ggtgcaactt caaccaacgg agacccattt    2460
cactcaaaac tagcaaagtt tgagtatgga gtttccaaat cccctatgaa gcttatagag    2520
attttgactg atataatgag agttgtcgag acaataagtg ttattcatga actaggattt    2580
gttcacaatg gcctaactag cagcaattta ttgaagtcag agaaaaatgt cagagatata    2640
aaaataacag gatgggggtt tgcattcagt tttactgaaa attgcagcca gggttacaga    2700
aataaacact tggcacaagt ccaagattta ataccttaca tggcaccaga ggtgttggct    2760
attacaaatt cggttgtgga ttatcggtcg gactttttact cgttaggggt aataatgtat    2820
gagttagttt tgggtatttt gccattcaaa aatagcaacc cccagaaatt gatcagaatg    2880
catacttttg aaaacccaat agctcccagt gctctagcac caggttggat ttcagagaaa    2940
ttgagtggcg ttattatgaa attgttagag aagcacccac ataacagata caccgactgc    3000
cactcattgc tccacgattt aattgaagtt aaaaatatgt acattagcaa attattggat    3060 tcagggggaaa caatccccca tagtaaccta aatttaagtg atcgccagta ctatttgact    3120
aaagaaaatt tacttcatcc cgagaaaatg ggaattactc ctgtacttgg gttgaaagaa    3180
agttttattg gaagaagaga tttcttgcaa aatgttactg aagtttacaa taacagcaaa    3240
aatgggattg atttactttt tatatccggt gaaagcggaa gaggtaaaac gataatatta    3300
caagatcttc gagcagcagc agttttgaaa caagactttt attactcatg gaagtttagt    3360 tttttttggag cagatacaca tgtgtaccgg tttcttgttg aaggtgttca aaagattatt    3420
acccagattc taaattcttc agaagaaatt caaaatacat ggagagatgt gattttgaca    3480
cacattccta tagatctaag catattattt tatttgattc ctgagctaaa agtactattg    3540
gggaaaaaat acacttccat ttacaaacat aaaattggaa tgggggatgct aaagagaagt    3600 ttcaaagaag accaaacact gagactagag attaaattga dacaaatact aaaagaattt    3660
ttcaaacttg tagcgaaaca aggcttgtct attttttttag atgatgtaca gtggtgttca    3720
gaagagtcct ggaggttatt atgtgatgta ttagattttg attcatctgg agaggtgcga    3780
gagagctata acatcaaaat agttgtgtgc tatgctttga atgcagacca tttagagaat    3840
gttaatatcg agcataaaaa gatttctttt tgccgatatg ccaaacaaag ccacttaaat    3900
ttgcgtgagt ttagtatacc tcatatccca cttgaagacg ctattgaatt tttgtgtgaa    3960
ccttacacga gactgcacga tcatgaatgt aacagtaaaa agtctgatgt aattgccaat    4020
ttaaactgca caaatgaata tcctcagaac acttgcaaag tcatcccccag tataatccaa    4080 gagttgtatc aatcatcaga agggaatgtt ttgcttttga tattcctaac aagaatgaca    4140
aagctatctg gcaaagttcc ctttcaacga ttttcggtca aaaattcata tctatatgat    4200
```

```
cacctactga ataqtaacta tggaactaca agaaaagaga ttcttacaaa ttatttgaat    4260
atgggaacta actcagacac aagagccttg cttaaagttg cagcgttaat ctccaatgga    4320
tcgggattct ttttttcaga tttaattgta gccaccgact tgcccatggc tgaagcgttt    4380
cagttgttac aaatatgtat tcattccaga ataattgttc ctactagcac atattataaa    4440
atacctatgg atttaatagc ctctgaccag actccatttg atttaacaga tgataatatt    4500
tggaaactag ccactttatg cagctacaag ttctatcatg attctatttg tactcatata    4560
atcaaagaat taaacgccag tggcgaattc aaagaacttt ctcggttatg tgggttgaga    4620
ttttacaata caattacaaa agaacgttta ttaaatattg gtggctatct tcaaatggct    4680
actcacttta gaaactcata cgaggtggca ggtcccgaag aaaatgaaaa gtatgttgaa    4740
gttttggtcc aggcaggacg atatgccata tcgacatata atatgaagtt gtctcaatgg    4800
tttttcaatg ttgttggcga attggtatat aatcttgatt cgaaaactca gttaaaatcc    4860
gtgttaacaa tagccgagaa tcattttaat tctcgtgaat ttgaacaatg cctaagtgtg    4920
gttgaaaatg cacagaggaa atttggtttt gacaggttga tattttccat tcaaatagtc    4980
cgttgcaaaa ttgaattagg tgattatgac gaagcacatc gaattgcaat tgaatgtctt    5040
aaggaattag gtgttccatt agatgacgat gacgaatata caagtgaaaa cctgcttgag    5100
acgtgtttgg gaaaaattcc gctctctgtt gctgacatta gaggtatttt gaagattaaa    5160
agatgcaaga attcaagaac attgctaatg tatcagttaa tttcagagct aattgtacta    5220
ttcaagcttc aaggtaaaga caaagtgaga aggtttctca cagcttatgc gatgagtcaa    5280
attcatactc aagggtcttc tccttattgt gcagtaattc ttatagactt tgcacaatca    5340
tttgtcaacg aaaccacaac ttcaggaatg cttaaagcaa aagaactcag tattgtcatg    5400
ttgtcattga ttaatagagc accagaaata tctttatcat atgttcagtc tatttatgaa    5460
tattatttca gttgtcatgc tgtattttt gaatcaattg aaaaaatgct ggatcttata    5520
catccaggta acgctagttc ccattgcaca agactgtctt attattcatc ttttcatttg    5580
atagttaatg tttccaagat tttcttttca tgtatgaatg gagaaagttt caaaatgttc    5640
tcaacattca gtgtaaatc ctatttaaca ggggatcccc aaatgcctga aatggacaat    5700 ttttttatacg atagtgaaat gttacttgct ggacattcag aattgaatga atttatgaga    5760
aaatatcagt cattcaacca aacttccgtt ggtaaatttt gctactattt aattgtacta    5820
cttgtaatgt cacgtgaaca cagatttgac gaggctgccg atttggtttt gaaagttttg    5880
gaagacttac tggaaaaatt gcctgtatct tttttgcatc atcaatatta cttaatatgt    5940
ggtaaagtgt ttgcttatca ccagaccaaa accccagaaa gtgaggaaca agtggaacgt    6000
attttggctc gtcaatttga aagatatgaa ttgtgggcac tgacgaataa gccgacccttt   6060 ctaccacggt acttgttgtt gagtacctac aaacagatta gagaaaacca tgttgacaag    6120
ttagaaatac tagattcatt tgaggaggcg ttacagacgg cccataaatt tcataatgta    6180
tatgatatgt gctggatcaa tttggaatgt gcaagatggt taattagcat aaaccaaaaa    6240
aggcacagaa tctcaagaat ggttaaacaa ggtcttaaaa ttttgagaag cttggaatta    6300
aataatcatt taagattagc tgaatttgaa tttgatgaat acattgagga cgaagatcac    6360
agaaataaat gggcagggtt aactaataat ccaacattgg atactgttac tacctggcaa    6420
caacagaaca tgcccgataa ggtatctcca tgcaatgaca agcagttggt ccacggaaaa    6480
caatttggca aaaaagagtt tgatagccat ttgctcagat tgcactttga tggccaatat    6540
```

-continued

```
acaggcctag atttgaattc agctattcgt gaatgtctag caatatccga agctttagac    6600
gaaaattcca ttctcacaaa gttgatggca tctgccatca agtattcagg tgccacatat    6660
ggggtaattg tcacgaagaa aaaccaggag acaccttttc ttagaacaat ggctcgcag     6720 cacaatattc acacattaaa caacatgcca atttccgacg acatttgtcc tgctcagttg    6780
attcgtcatg tattgcatac aggagaaacg gtgaacaaag ctcatgatca cataggattt    6840
gctaacaagt ttgagaatga atactttcaa caacagata aaaagtattc agttgtgtgt     6900
ttgccattaa agagtctgct tggattattt ggtgcacttt atctagaagg tagtgatggt    6960
gattttggac atgaagattt gttcaatgaa aggaaatgtg atttgttaca acttttttgc    7020
acacaagcag ctgtggcttt gggtaaggag cgtttgcttt tgcaaatgga actagcaaaa    7080
atggcagcag aagacgccac tgatgaaaaa gccagttttt tggcaaacat gtcacatgaa    7140
atacgaaccc cattcaattc gttattgtca tttgctattt ttttgttaga taccaaattg    7200
gattctactc aaagagaata tgtcgaggca attcagagct ccgcaatgat aacgttgaat    7260
attattgatg ggatacttgc gttttccaaa attgagcatg gatcctttac attagaaaat    7320 gcccccttt ctttgaatga ttgtatcgag actgctattc aagtaagtgg ggaaacaatt    7380
ttgaatgacc agattgagtt ggtgttttgt aacaattgtc cagagattga atttgtggtt    7440
ggtgatctaa cgaggttcag acaaattgtg atcaatttgg tgggtaatgr aaggctatta    7500
agtttacaac caaggtcat gttttgattt cttgtgatag ccgaaaaatt acggacgaca     7560
gatttgagat caatgtgtca gttgaggatt caggaattgg aatttccaaa aaatctcaaa    7620
ataaagtgtt tggagcattt tctcaagtag atggttccgc aagacgagaa tatggtggct    7680
ctggattagg tttagctata tcaaagaaat tgactgaact aatgggtggc acaattagat    7740
ttgaaagtga ggaagggatt ggcacaacgt tttatgttag cgtcattatg gacgcaaaag    7800
aatactcatc cccgccattt agtttaaata aaaaatgttt gatttacagc cagcattgtc    7860
ttactgccaa gtcaatttca aatatgctta attattttgg atcaacagtt aaagtcacta    7920
atcagaagtc tgagttttca acttccgtgc aagccaacga catcattttt gttgatcgcg    7980
gaatggaacc tgatgttagt tgcaaaacca aaatcattcc catcgaccca aaaccttca     8040 aaagaaacaa actcattagt attctcaaag aacaaccaag tttgcccacc aaagtgtttg    8100
gaaacaacaa atctaattta tcaaaacaat accctctaag aatattatta gcagaagaca    8160
atcttttgaa ctataaagta tgtttgaagc atttggataa attggggtac aaggcagatc    8220
atgccaaaga tggagtagta gttttggata aatgtaaaga actactagaa aaagacgaaa    8280
aatatgatgt catattgatg gatattcaaa tgcctcgtaa ggacggtatt acagctacaa    8340
gggatttgaa acattgtttt cacacacaaa aaaggaaag ttggttaccc gtgatcgtag     8400
cattgacagc taatgttgct ggagacgaca aaaagaggtg tctagaagag ggaatgtttg    8460
attttataac caaacccatt ttaccagatg aacttagacg tatttttaaca aaagtaggg    8520 aaacagtgaa tatgtaaaat gtgtatttaa taataagatc t                        8561
```

<210> SEQ ID NO 4
<211> LENGTH: 2471
<212> TYPE: PRT
<213> ORGANISM: Homo sapiens

<400> SEQUENCE: 4

```
Met Ser Met Asn Phe Phe Asn Ser Ser Glu Pro Ala Arg Asp His Lys
 1               5                  10                  15
```

```
Pro Asp Gln Glu Lys Glu Thr Val Met Thr Thr Glu His Tyr Glu Phe
             20                  25                  30

Glu Arg Pro Asp Val Lys Ala Ile Arg Asn Phe Lys Phe Phe Arg Leu
         35                  40                  45

Asp Glu Thr Glu Thr Lys Lys Gly Pro Asn Leu His Ile Ser Asp Leu
     50                  55                  60

Ser Pro Leu Glu Ser Gln Ser Val Pro Pro Ser Ala Leu Ser Leu Asn
 65                  70                  75                  80

His Ser Ile Ile Pro Asp Gln Tyr Glu Arg Arg Gln Asp Thr Pro Asp
                 85                  90                  95

Pro Ile His Thr Pro Glu Ile Ser Leu Ser Asp Tyr Leu Tyr Asp Gln
            100                 105                 110

Thr Leu Ser Pro Gln Gly Phe Asp Asn Ser Arg Glu Asn Phe Asn Ile
        115                 120                 125

His Lys Thr Ile Ala Ser Leu Phe Glu Asp Asn Ser Ser Val Val Ser
    130                 135                 140

Gln Glu Ser Thr Asp Asp Thr Lys Thr Thr Leu Ser Leu Glu Thr Cys
145                 150                 155                 160

Asp Ser Phe Ser Leu Asn Asn Ala Ser Tyr Leu Thr Asn Ile Asn Phe
                165                 170                 175

Val Gln Asn His Leu Gln Tyr Leu Ser Gln Asn Val Leu Gly Asn Arg
            180                 185                 190

Thr Ser Asn Ser Leu Pro Pro Ser Ser Ser Gln Ile Asp Phe Asp
        195                 200                 205

Ala Ser Asn Leu Thr Pro Asp Ser Ile Pro Gly Tyr Ile Leu Asn Lys
    210                 215                 220

Lys Leu Gly Ser Val His Gln Leu Thr Asp Leu Val Tyr Asn Ala Ile
225                 230                 235                 240

Lys Ile Pro Gln Asn Glu Glu Tyr Asn Cys Cys Thr Lys Ala Ser Ala
                245                 250                 255

Ser Gln Asn Pro Thr Asn Leu Asn Ser Lys Val Ile Val Arg Leu Ser
            260                 265                 270

Pro Asn Ile Phe Gln Asn Leu Ser Leu Ser Arg Phe Leu Asn Glu Trp
        275                 280                 285

Tyr Ile Leu Ser Gly Lys His Ser Ser Lys Glu His Gln Ile Trp Ser
    290                 295                 300

Asn Glu Ser Leu Thr Asn Glu Tyr Val Gln Asp Lys Thr Ile Pro Thr
305                 310                 315                 320

Phe Asp Lys Glu Ser Ala Arg Phe Arg Pro Thr Leu Pro Ile Asn Ile
                325                 330                 335

Pro Gly Ile Leu Tyr Pro Gln Glu Ile Ile Asn Phe Cys Val Asn Ser
            340                 345                 350

His Asp Tyr Pro Leu Glu His Pro Ser Gln Ser Thr Asp Gln Lys Arg
        355                 360                 365

Phe Ala Met Val Tyr Gln Asp Asn Asp Tyr Lys Thr Phe Lys Glu Leu
    370                 375                 380

Ser Met Phe Thr Leu His Glu Leu Gln Thr Arg Gln Gly Ser Tyr Ser
385                 390                 395                 400

Ser Asn Glu Ser Arg Arg Lys Ser Ser Ser Gly Phe Asn Ile Gly Val
                405                 410                 415

Asn Ala Thr Thr Thr Glu Ala Gly Ser Leu Glu Ser Phe Ser Asn Leu
            420                 425                 430

Met Gln Asn His His Leu Gly Ala Thr Ser Thr Asn Gly Asp Pro Phe
```

-continued

```
            435             440             445
His Ser Lys Leu Ala Lys Phe Glu Tyr Gly Val Ser Lys Ser Pro Met
        450             455             460
Lys Leu Ile Glu Ile Leu Thr Asp Ile Met Arg Val Val Glu Thr Ile
465             470             475             480
Ser Val Ile His Glu Leu Gly Phe Val His Asn Gly Leu Thr Ser Ser
            485             490             495
Asn Leu Leu Lys Ser Glu Lys Asn Val Arg Asp Ile Lys Ile Thr Gly
            500             505             510
Trp Gly Phe Ala Phe Ser Phe Thr Glu Asn Cys Ser Gln Gly Tyr Arg
            515             520             525
Asn Lys His Leu Ala Gln Val Gln Asp Leu Ile Pro Tyr Met Ala Pro
            530             535             540
Glu Val Leu Ala Ile Thr Asn Ser Val Val Asp Tyr Arg Ser Asp Phe
545             550             555             560
Tyr Ser Leu Gly Val Ile Met Tyr Glu Leu Val Leu Gly Ile Leu Pro
            565             570             575
Phe Lys Asn Ser Asn Pro Gln Lys Leu Ile Arg Met His Thr Phe Glu
            580             585             590
Asn Pro Ile Ala Pro Ser Ala Leu Ala Pro Gly Trp Ile Ser Glu Lys
            595             600             605
Leu Ser Gly Val Ile Met Lys Leu Leu Glu Lys His Pro His Asn Arg
            610             615             620
Tyr Thr Asp Cys His Ser Leu Leu His Asp Leu Ile Glu Val Lys Asn
625             630             635             640
Met Tyr Ile Ser Lys Leu Leu Asp Ser Gly Glu Thr Ile Pro Asn Ser
            645             650             655
Asn Leu Asn Leu Ser Asp Arg Gln Tyr Tyr Leu Thr Lys Glu Asn Leu
            660             665             670
Leu His Pro Glu Lys Met Gly Ile Thr Pro Val Leu Gly Leu Lys Glu
            675             680             685
Ser Phe Ile Gly Arg Arg Asp Phe Leu Gln Asn Val Thr Glu Val Tyr
            690             695             700
Asn Asn Ser Lys Asn Gly Ile Asp Leu Leu Phe Ile Ser Gly Glu Ser
705             710             715             720
Gly Arg Gly Lys Thr Ile Ile Leu Gln Asp Leu Arg Ala Ala Ala Val
            725             730             735
Leu Lys Gln Asp Phe Tyr Tyr Ser Trp Lys Phe Ser Phe Phe Gly Ala
            740             745             750
Asp Thr His Val Tyr Arg Phe Leu Val Glu Gly Val Gln Lys Ile Ile
            755             760             765
Thr Gln Ile Leu Asn Ser Ser Glu Glu Ile Gln Asn Thr Trp Arg Asp
            770             775             780
Val Ile Leu Thr His Ile Pro Ile Asp Leu Ser Ile Leu Phe Tyr Leu
785             790             795             800
Ile Pro Glu Leu Lys Val Leu Leu Gly Lys Lys Tyr Thr Ser Ile Tyr
            805             810             815
Lys His Lys Ile Gly Met Gly Met Leu Lys Arg Ser Phe Lys Glu Asp
            820             825             830
Gln Thr Leu Arg Leu Glu Ile Lys Leu Arg Gln Ile Leu Lys Glu Phe
            835             840             845
Phe Lys Leu Val Ala Lys Gln Gly Leu Ser Ile Phe Leu Asp Asp Val
850             855             860
```

-continued

```
Gln Trp Cys Ser Glu Ser Trp Arg Leu Leu Cys Asp Val Leu Asp
865                 870                 875                 880

Phe Asp Ser Ser Gly Glu Val Arg Glu Ser Tyr Asn Ile Lys Ile Val
                885                 890                 895

Val Cys Tyr Ala Leu Asn Ala Asp His Leu Glu Asn Val Asn Ile Glu
                900                 905                 910

His Lys Lys Ile Ser Phe Cys Arg Tyr Ala Lys Gln Ser His Leu Asn
                915                 920                 925

Leu Arg Glu Phe Ser Ile Pro His Ile Pro Leu Glu Asp Ala Ile Glu
    930                 935                 940

Phe Leu Cys Glu Pro Tyr Thr Arg Leu His Asp His Glu Cys Asn Ser
945                 950                 955                 960

Lys Lys Ser Asp Val Ile Ala Asn Leu Asn Cys Thr Asn Glu Tyr Pro
                965                 970                 975

Gln Asn Thr Cys Lys Val Ile Pro Ser Ile Ile Gln Glu Leu Tyr Gln
                980                 985                 990

Ser Ser Glu Gly Asn Val Leu Leu Ile Phe Leu Thr Arg Met Thr
                995                 1000                1005

Lys Leu Ser Gly Lys Val Pro Phe Gln Arg Phe Ser Val Lys Asn Ser
    1010                1015                1020

Tyr Leu Tyr Asp His Leu Leu Asn Ser Asn Tyr Gly Thr Thr Arg Lys
1025                1030                1035                1040

Glu Ile Leu Thr Asn Tyr Leu Asn Met Gly Thr Asn Ser Asp Thr Arg
                1045                1050                1055

Ala Leu Leu Lys Val Ala Ala Leu Ile Ser Asn Gly Ser Gly Phe Phe
                1060                1065                1070

Phe Ser Asp Leu Ile Val Ala Thr Asp Leu Pro Met Ala Glu Ala Phe
                1075                1080                1085

Gln Leu Leu Gln Ile Cys Ile His Ser Arg Ile Ile Val Pro Thr Ser
                1090                1095                1100

Thr Tyr Tyr Lys Ile Pro Met Asp Leu Ile Ala Ser Asp Gln Thr Pro
1105                1110                1115                1120

Phe Asp Leu Thr Asp Asp Asn Ile Trp Lys Leu Ala Thr Leu Cys Ser
                1125                1130                1135

Tyr Lys Phe Tyr His Asp Ser Ile Cys Thr His Ile Ile Lys Glu Leu
                1140                1145                1150

Asn Ala Ser Gly Glu Phe Lys Glu Leu Ser Arg Leu Cys Gly Leu Arg
    1155                1160                1165

Phe Tyr Asn Thr Ile Thr Lys Glu Arg Leu Leu Asn Ile Gly Gly Tyr
    1170                1175                1180

Leu Gln Met Ala Thr His Phe Arg Asn Ser Tyr Glu Val Ala Gly Pro
1185                1190                1195                1200

Glu Glu Asn Glu Lys Tyr Val Glu Val Leu Val Gln Ala Gly Arg Tyr
                1205                1210                1215

Ala Ile Ser Thr Tyr Asn Met Lys Leu Ser Gln Trp Phe Phe Asn Val
                1220                1225                1230

Val Gly Glu Leu Val Tyr Asn Leu Asp Ser Lys Thr Gln Leu Lys Ser
    1235                1240                1245

Val Leu Thr Ile Ala Glu Asn His Phe Asn Ser Arg Glu Phe Glu Gln
    1250                1255                1260

Cys Leu Ser Val Val Glu Asn Ala Gln Arg Lys Phe Gly Phe Asp Arg
1265                1270                1275                1280
```

```
Leu Ile Phe Ser Ile Gln Ile Val Arg Cys Lys Ile Glu Leu Gly Asp
            1285                1290                1295

Tyr Asp Glu Ala His Arg Ile Ala Ile Glu Cys Leu Lys Glu Leu Gly
        1300                1305                1310

Val Pro Leu Asp Asp Asp Glu Tyr Thr Ser Glu Asn Leu Leu Glu
    1315                1320                1325

Thr Cys Leu Gly Lys Ile Pro Leu Ser Val Ala Asp Ile Arg Gly Ile
    1330                1335                1340

Leu Lys Ile Lys Arg Cys Lys Asn Ser Arg Thr Leu Leu Met Tyr Gln
1345                1350                1355                1360

Leu Ile Ser Glu Leu Ile Val Leu Phe Lys Leu Gln Gly Lys Asp Lys
            1365                1370                1375

Val Arg Arg Phe Leu Thr Ala Tyr Ala Met Ser Gln Ile His Thr Gln
            1380                1385                1390

Gly Ser Ser Pro Tyr Cys Ala Val Ile Leu Ile Asp Phe Ala Gln Ser
            1395                1400                1405

Phe Val Asn Glu Thr Thr Thr Ser Gly Met Leu Lys Ala Lys Glu Leu
    1410                1415                1420

Ser Ile Val Met Leu Ser Leu Ile Asn Arg Ala Pro Glu Ile Ser Leu
1425                1430                1435                1440

Ser Tyr Val Gln Ser Ile Tyr Glu Tyr Tyr Phe Ser Cys His Ala Val
            1445                1450                1455

Phe Phe Glu Ser Ile Glu Lys Met Leu Asp Leu Ile His Pro Gly Asn
            1460                1465                1470

Ala Ser Ser His Cys Thr Arg Leu Ser Tyr Tyr Ser Ser Phe His Leu
            1475                1480                1485

Ile Val Asn Val Ser Lys Ile Phe Phe Ser Cys Met Asn Gly Glu Ser
    1490                1495                1500

Phe Lys Met Phe Ser Thr Phe Lys Cys Lys Ser Tyr Leu Thr Gly Asp
1505                1510                1515                1520

Pro Gln Met Pro Glu Met Asp Asn Phe Leu Tyr Asp Ser Glu Met Leu
            1525                1530                1535

Leu Ala Gly His Ser Glu Leu Asn Glu Phe Met Arg Lys Tyr Gln Ser
            1540                1545                1550

Phe Asn Gln Thr Ser Val Gly Lys Phe Cys Tyr Tyr Leu Ile Val Leu
            1555                1560                1565

Leu Val Met Ser Arg Glu His Arg Phe Asp Glu Ala Ala Asp Leu Val
            1570                1575                1580

Leu Lys Val Leu Glu Asp Leu Leu Glu Lys Leu Pro Val Ser Phe Leu
1585                1590                1595                1600

His His Gln Tyr Tyr Leu Ile Cys Gly Lys Val Phe Ala Tyr His Gln
            1605                1610                1615

Thr Lys Thr Pro Glu Ser Glu Glu Gln Val Glu Arg Ile Leu Ala Arg
            1620                1625                1630

Gln Phe Glu Arg Tyr Glu Leu Trp Ala Leu Thr Asn Lys Pro Thr Leu
            1635                1640                1645

Leu Pro Arg Tyr Leu Leu Leu Ser Thr Tyr Lys Gln Ile Arg Glu Asn
    1650                1655                1660

His Val Asp Lys Leu Glu Ile Leu Asp Ser Phe Glu Glu Ala Leu Gln
1665                1670                1675                1680

Thr Ala His Lys Phe His Asn Val Tyr Asp Met Cys Trp Ile Asn Leu
            1685                1690                1695

Glu Cys Ala Arg Trp Leu Ile Ser Ile Asn Gln Lys Arg His Arg Ile
```

-continued

```
             1700            1705            1710
Ser Arg Met Val Lys Gln Gly Leu Lys Ile Leu Arg Ser Leu Glu Leu
         1715            1720            1725
Asn Asn His Leu Arg Leu Ala Glu Phe Glu Phe Asp Glu Tyr Ile Glu
     1730            1735            1740
Asp Glu Asp His Arg Asn Lys Trp Ala Gly Leu Thr Asn Asn Pro Thr
 1745            1750            1755            1760
Leu Asp Thr Val Thr Thr Trp Gln Gln Gln Asn Met Pro Asp Lys Val
             1765            1770            1775
Ser Pro Cys Asn Asp Lys Gln Leu Val His Gly Lys Gln Phe Gly Lys
         1780            1785            1790
Lys Glu Phe Asp Ser His Leu Leu Arg Leu His Phe Asp Gly Gln Tyr
         1795            1800            1805
Thr Gly Leu Asp Leu Asn Ser Ala Ile Arg Glu Cys Leu Ala Ile Ser
     1810            1815            1820
Glu Ala Leu Asp Glu Asn Ser Ile Leu Thr Lys Leu Met Ala Ser Ala
 1825            1830            1835            1840
Ile Lys Tyr Ser Gly Ala Thr Tyr Gly Val Ile Val Thr Lys Lys Asn
         1845            1850            1855
Gln Glu Thr Pro Phe Leu Arg Thr Ile Gly Ser Gln His Asn Ile His
     1860            1865            1870
Thr Leu Asn Asn Met Pro Ile Ser Asp Asp Ile Cys Pro Ala Gln Leu
         1875            1880            1885
Ile Arg His Val Leu His Thr Gly Glu Thr Val Asn Lys Ala His Asp
         1890            1895            1900
His Ile Gly Phe Ala Asn Lys Phe Glu Asn Glu Tyr Phe Gln Thr Thr
 1905            1910            1915            1920
Asp Lys Lys Tyr Ser Val Val Cys Leu Pro Leu Lys Ser Leu Leu Gly
             1925            1930            1935
Leu Phe Gly Ala Leu Tyr Leu Glu Gly Ser Asp Gly Asp Phe Gly His
         1940            1945            1950
Glu Asp Leu Phe Asn Glu Arg Lys Cys Asp Leu Leu Gln Leu Phe Cys
         1955            1960            1965
Thr Gln Ala Ala Val Ala Leu Gly Lys Glu Arg Leu Leu Leu Gln Met
     1970            1975            1980
Glu Leu Ala Lys Met Ala Ala Glu Asp Ala Thr Asp Glu Lys Ala Ser
 1985            1990            1995            2000
Phe Leu Ala Asn Met Ser His Glu Ile Arg Thr Pro Phe Asn Ser Leu
             2005            2010            2015
Leu Ser Phe Ala Ile Phe Leu Leu Asp Thr Lys Leu Asp Ser Thr Gln
         2020            2025            2030
Arg Glu Tyr Val Glu Ala Ile Gln Ser Ser Ala Met Ile Thr Leu Asn
         2035            2040            2045
Ile Ile Asp Gly Ile Leu Ala Phe Ser Lys Ile Glu His Gly Ser Phe
     2050            2055            2060
Thr Leu Glu Asn Ala Pro Phe Ser Leu Asn Asp Cys Ile Glu Thr Ala
 2065            2070            2075            2080
Ile Gln Val Ser Gly Glu Thr Ile Leu Asn Asp Gln Ile Glu Leu Val
             2085            2090            2095
Phe Cys Asn Asn Cys Pro Glu Ile Glu Phe Val Val Gly Asp Leu Thr
         2100            2105            2110
Arg Phe Arg Gln Ile Val Ile Asn Leu Val Gly Asn Ala Ile Lys Phe
         2115            2120            2125
```

-continued

```
Thr Thr Lys Gly His Val Leu Ile Ser Cys Asp Ser Arg Lys Ile Thr
    2130                2135                2140

Asp Asp Arg Phe Glu Ile Asn Val Ser Val Glu Asp Ser Gly Ile Gly
2145                2150                2155                2160

Ile Ser Lys Lys Ser Gln Asn Lys Val Phe Gly Ala Phe Ser Gln Val
            2165                2170                2175

Asp Gly Ser Ala Arg Arg Glu Tyr Gly Gly Ser Gly Leu Gly Leu Ala
            2180                2185                2190

Ile Ser Lys Lys Leu Thr Glu Leu Met Gly Gly Thr Ile Arg Phe Glu
            2195                2200                2205

Ser Glu Glu Gly Ile Gly Thr Thr Phe Tyr Val Ser Val Ile Met Asp
    2210                2215                2220

Ala Lys Glu Tyr Ser Ser Pro Pro Phe Ser Leu Asn Lys Lys Cys Leu
2225                2230                2235                2240

Ile Tyr Ser Gln His Cys Leu Thr Ala Lys Ser Ile Ser Asn Met Leu
            2245                2250                2255

Asn Tyr Phe Gly Ser Thr Val Lys Val Thr Asn Gln Lys Ser Glu Phe
            2260                2265                2270

Ser Thr Ser Val Gln Ala Asn Asp Ile Ile Phe Val Asp Arg Gly Met
    2275                2280                2285

Glu Pro Asp Val Ser Cys Lys Thr Lys Ile Ile Pro Ile Asp Pro Lys
    2290                2295                2300

Pro Phe Lys Arg Asn Lys Leu Ile Ser Ile Leu Lys Glu Gln Pro Ser
2305                2310                2315                2320

Leu Pro Thr Lys Val Phe Gly Asn Asn Lys Ser Asn Leu Ser Lys Gln
            2325                2330                2335

Tyr Pro Leu Arg Ile Leu Leu Ala Glu Asp Asn Leu Leu Asn Tyr Lys
            2340                2345                2350

Val Cys Leu Lys His Leu Asp Lys Leu Gly Tyr Lys Ala Asp His Ala
            2355                2360                2365

Lys Asp Gly Val Val Val Leu Asp Lys Cys Lys Glu Leu Leu Glu Lys
    2370                2375                2380

Asp Glu Lys Tyr Asp Val Ile Leu Met Asp Ile Gln Met Pro Arg Lys
2385                2390                2395                2400

Asp Gly Ile Thr Ala Thr Arg Asp Leu Lys Thr Leu Phe His Thr Gln
            2405                2410                2415

Lys Lys Glu Ser Trp Leu Pro Val Ile Val Ala Leu Thr Ala Asn Val
            2420                2425                2430

Ala Gly Asp Asp Lys Lys Arg Cys Leu Glu Glu Gly Met Phe Asp Phe
            2435                2440                2445

Ile Thr Lys Pro Ile Leu Pro Asp Glu Leu Arg Arg Ile Leu Thr Lys
    2450                2455                2460

Val Gly Glu Thr Val Asn Met
2465                2470

<210> SEQ ID NO 5
<211> LENGTH: 20
<212> TYPE: DNA
<213> ORGANISM: Homo sapiens

<400> SEQUENCE: 5
ccactcatta agaaaacgcg                                             20

<210> SEQ ID NO 6
```

-continued

```
<211> LENGTH: 27
<212> TYPE: DNA
<213> ORGANISM: Homo sapiens

<400> SEQUENCE: 6
cagtatctct cacctaacgt acagacc                                              27

<210> SEQ ID NO 7
<211> LENGTH: 23
<212> TYPE: DNA
<213> ORGANISM: Homo sapiens

<400> SEQUENCE: 7
cggtttttgt gttagaaata gcc                                                  23

<210> SEQ ID NO 8
<211> LENGTH: 11
<212> TYPE: DNA
<213> ORGANISM: Homo sapiens

<400> SEQUENCE: 8
aaatcatgtc t                                                               11

<210> SEQ ID NO 9
<211> LENGTH: 11
<212> TYPE: DNA
<213> ORGANISM: Homo sapiens

<400> SEQUENCE: 9
aaayaatgtc t                                                               11
```